United States Patent
Chen et al.

(10) Patent No.: US 6,750,321 B1
(45) Date of Patent: Jun. 15, 2004

(54) INSULIN-LIKE GROWTH FACTOR AGONIST MOLECULES

(75) Inventors: Yvonne Man-yee Chen, San Mateo, CA (US); Ross G. Clark, Auckland (NZ); Andrea G. Cochran, San Francisco, CA (US); Henry B. Lowman, El Granada, CA (US); Iain C. A. F. Robinson, St. Albans (GB); Nicolas J. Skelton, San Mateo, CA (US)

(73) Assignee: Genentech, Inc., South San Francisco, CA (US)

( * ) Notice: Subject to any disclaimer, the term of this patent is extended or adjusted under 35 U.S.C. 154(b) by 86 days.

(21) Appl. No.: 09/723,185

(22) Filed: Nov. 27, 2000

Related U.S. Application Data

(60) Division of application No. 09/337,227, filed on Jun. 22, 1999, now Pat. No. 6,420,518, which is a continuation-in-part of application No. 09/052,888, filed on Mar. 31, 1998, now Pat. No. 6,251,865, which is a continuation-in-part of application No. 08/825,852, filed on Apr. 4, 1997, now Pat. No. 6,121,416.

(51) Int. Cl.$^7$ .................................. C07K 7/50

(52) U.S. Cl. .......................... 530/317; 530/328; 930/270

(58) Field of Search ............................ 530/317, 328; 930/270

(56) References Cited

U.S. PATENT DOCUMENTS

| | | |
|---|---|---|
| 4,411,890 A | 10/1983 | Momany |
| 4,876,242 A | 10/1989 | Applebaum et al. |
| 4,988,675 A | 1/1991 | Froesch et al. |
| 5,068,224 A | 11/1991 | Fryklund et al. |
| 5,077,276 A | 12/1991 | Ballard et al. |
| 5,093,317 A | 3/1992 | Lewis et al. |
| 5,106,832 A | 4/1992 | Froesch et al. |
| 5,126,324 A | 6/1992 | Clark et al. |
| 5,164,370 A | 11/1992 | Ballard et al. |
| 5,187,151 A | 2/1993 | Clark et al. |
| 5,202,119 A | 4/1993 | Clark et al. |
| 5,206,235 A | 4/1993 | Fisher et al. |
| 5,210,017 A | 5/1993 | Carlsson et al. |
| 5,223,409 A | 6/1993 | Ladner et al. |
| 5,273,961 A | 12/1993 | Clark |
| 5,374,620 A | 12/1994 | Clark et al. |
| 5,466,670 A | 11/1995 | Dunger et al. |
| 5,470,828 A | 11/1995 | Ballard et al. |
| 5,534,617 A | 7/1996 | Cunningham et al. |
| 5,569,648 A | 10/1996 | Lewis et al. |
| 5,593,844 A | 1/1997 | Carlsson et al. |
| 5,597,797 A | 1/1997 | Clark |
| 5,622,932 A | 4/1997 | DiMarchi et al. |
| 5,652,214 A | 7/1997 | Lewis et al. |
| 5,703,045 A | 12/1997 | Lewis et al. |
| 5,714,460 A | 2/1998 | Gluckman et al. |
| 5,776,897 A | 7/1998 | Lewis et al. |

FOREIGN PATENT DOCUMENTS

| | | |
|---|---|---|
| EP | 128733 | 12/1984 |
| EP | 135094 | 3/1985 |
| EP | 230869 | 8/1987 |
| EP | 288451 | 10/1988 |
| EP | 294021 | 12/1988 |
| EP | 369943 | 5/1990 |
| EP | 375438 | 6/1990 |
| EP | 379338 | 7/1990 |
| EP | 681842 | 11/1995 |
| EP | 742228 | 11/1996 |
| EP | 965596 | 12/1999 |
| WO | WO 89/05822 | 6/1989 |
| WO | WO 89/08667 | 9/1989 |
| WO | WO 89/09268 | 10/1989 |
| WO | WO 89/09792 | 10/1989 |
| WO | WO 91/03253 | 3/1991 |
| WO | WO 92/11865 | 7/1992 |
| WO | WO 92/15679 | 9/1992 |
| WO | WO 93/08826 | 5/1993 |
| WO | WO 93/20836 | 10/1993 |
| WO | WO 93/23071 | 11/1993 |
| WO | WO 93/25219 | 12/1993 |
| WO | WO 94/04569 | 3/1994 |
| WO | WO 94/16722 | 8/1994 |
| WO | WO 94/16723 | 8/1994 |
| WO | WO 95/07697 | 3/1995 |
| WO | WO 95/17422 | 6/1995 |
| WO | WO 95/17423 | 6/1995 |
| WO | WO 96/01124 | 1/1996 |
| WO | WO 96/15148 | 5/1996 |
| WO | WO 96/33216 | 10/1996 |
| WO | WO 96/37514 | 11/1996 |
| WO | WO 96/40189 | 12/1996 |
| WO | WO 96/40750 | 12/1996 |
| WO | WO 97/37010 | 10/1997 |
| WO | WO 97/39032 | 10/1997 |
| WO | WO 98/20036 | 5/1998 |
| WO | WO 98/45427 | 10/1998 |
| WO | WO 00/23469 | 4/2000 |
| WO | WO 01/72771 | 10/2001 |

OTHER PUBLICATIONS

Ngo et al., in The Protein Folding Problem and Tertiary Structure Prediction, Merz and Le Grand (Eds), Aug. 1994, Springer Verlag, pp. 433 and 492–495.*

Arttamangkul et al. Synthesis and opioid activity of conformationally constrained dynorphin A analogues. 2. Conformational constraint in the "address" sequence. Journal of Medicinal Chemistry, (Apr. 11, 1997) 40(8) 1211–8.*

Alberts et al. *Molecular Biology of the Cell*, 3RD edition, New York: Garland Publishing, Inc. pp. 119 (1994).

(List continued on next page.)

Primary Examiner—David Romeo
(74) Attorney, Agent, or Firm—Janet E. Hasak; Heller Ehrman White & McAuliffe, LLP

(57) ABSTRACT

Peptides are provided that inhibit the interaction of an IGF with any one of its binding proteins and not to a human IGF receptor. These IGF agonist peptides are useful to increase serum and tissue levels of active IGFs in a mammal.

7 Claims, 44 Drawing Sheets

OTHER PUBLICATIONS

Bach and Rechler, "Insulin–like Growth Factor Binding Proteins" *Diabetes Reviews* 3:38–61 (1995).

Ballard et al., "Does IGF–Ever Act Through the Insulin Receptor?" *The Insulin–like Growth Factors and Their Regulatory Proteins*, Baxter, eds., Amsterdam: Elsevier pps. 131–138 (1994).

Bar et al., "Tissue localization of perfused endothelial cell IGF binding protein is markedly altered by association with IGF–I" *Endocrinology* 127(6):3243–3245 (1990).

Bass et al., "Hormone Phage: An Enrichment Method for Variant Proteins with Altered Binding Properties" *Proteins: Structure, Function, and Genetics* 8(4):309–314 (1990).

Baxter & Martin, "Binding Proteins for Insulin–Like Growth Factors in Adult Rat Serum. Comparison With Other Human and Rat Binding Proteins" *Biochem. & Biophys. Res. Comm.* 147(1):408–415 (1987).

Baxter et al., "Structural determinants for binary and ternary complex formation between insulin–like growth factor–I (IGF–I) and IGF binding protein–3" *Journal of Biological Chemistry* 267(1):60–65 (Jan. 5, 1992).

Baxter, "Physiological Roles of IGF Binding Proteins" *Modern Concepts of Insulin–like Growth Factors,* Spencer, eds., Elsevier, New York pp. 371–380 (1991).

Baxter, "The somatomedins: insulin–like growth factors" *Advances in Clinical Chemistry* 25:49–115 (1986).

Baxter, R., "The Insulin–Like Growth Factors and Their Binding Proteins" *Comp. Biochem. Physiol.* 91B(2):229–235 (1988).

Bayne et al., "Structural analogs of human insulin–like growth factor I with reduced affinity for serum binding proteins and the type 2 insulin–like growth factor receptor" *Journal of Biological Chemistry* 263:6233–6239 (1988).

Bayne et al., "The C region of human insulin–like growth factor (IGF) I is required for high affinity binding to the type 1 IGF receptor" *Journal of Biological Chemistry* 264(19):11004–11008 (Jul. 5, 1989).

Bayne et al., "The roles of tyrosines 24, 31, and 60 in the high affinity binding of insulin–like growth factor–I to the type I insulin–like growth factor receptor" *Journal of Biological Chemistry* 265(26):15648–15652 (Sep. 15, 1990).

Binkert et al., "Cloning, sequence analysis and expression of a cDNA encoding a novel insulin–like growth factor binding protein (IGFBP–2)" *EMBO Journal* 8:2497–2502 (1989).

Binoux, M., "Donnees recentes sur les somatomedines (Insulin–like growth factors)" *Annales d'Endocrinologie* 41:157–192 (1980).

Bondy, C., "Clinical uses of insulin–like growth factor I" *Annals of Internal Medicine* 120:593–601 (1994).

Bowers, C. Y., "GH Releasing Peptides—Structure and Kinetics" *J. Pediatr. Endocrinology* 6(1):21–31 (1993).

Bowie et al., "Deciphering the Message in Protein Sequences: Tolerance to Amino Acid Substitutions" *Science* 247:1306–1310 (1990).

Brandt et al., "Role of natriuretic peptide clearance receptor in in vivo control of C–type natriuretic peptide" *American Journal of Physiology* 269 (1 Pt 2): H326–H331 (Jul. 1995).

Brewer et al., "Cloning, Characterization, and Expression of a Human Insulin–Like Growth Factor Binding Protein" *Biochem. & Biophys. Res. Comm.* 152(3):1289–1297 (1988).

Brinkman et al., "Isolation and characterization of a cDNA encoding the low molecular weight insulin–like growth factor binding protein (IBP–1)" *The EMBO J.* 7:2417–2423 (1988).

Carlsson et al., "Growth Hormone and Growth in Diabetic Rats: Effects of Insulin and Insulin–Like Growth Factor–I Infusions" *J. Endocrinol.* 122:661–670 (1989).

Cascieri et al., "Analysis of the interaction of IGF–I analogs with the IGF–I receptor and IGF binding proteins" *Advances in Experimental Medicine & Biology* 343:33–40 (1993).

Cascieri et al., "Mutants of human insulin–like growth factor I with reduced affinity for the type 1 insulin–like growth factor receptor" *Biochemistry* 27(9):3229–3233 (May 3, 1988).

Cascieri et al., "Structural analogs of human insulin–like growth factor (IGF) I with altered affinity for type 2 IGF receptors" *Journal of Biological Chemistry* 264:2199–2202 (1989).

Charlton et al., "Growth hormone–deficient dwarfism in the rat: a new mutation" *J. of Endocrinology* 119:51–58 (1988).

Cheetham et al., "The Effects of Recombinant Human Insulin–like Growth Factor I on Growth Hormone Secretion in Adolescents With Insulin Dependent Diabetes Mellitus" *Clin. Endocrinol.* 40:515–522 (1994).

Cheetham et al., "The Effects of Recombinant Insulin–like Growth Factor I Adminstration on Growth Hormone Levels and Insulin Requirements in Adolescents With Type 1 (Insulin–dependent) Diabetes Mellitus" *Diabetologia* 36:678–681 (1993).

Chen et al., "Recombinant human IGF–I infusion results in transient improvement in nitrogen balance: evidence for IGF–I autoregulation" *US Endocrine Meeting* (Abstract 1596) pp. 449 (1993).

Clark et al., "Growth–Responses to Patterned GH Delivery" *Endocrine* 3:717–723 (1995).

Clark et al., "Insulin–Like Growth Factor–1 and Growth Hormone (GH) Have Distinct and Overlapping anabolic Effects in GH–Deficient Rats" *Endocrine* 3:297–304 (1995).

Clemmons and Van Wyk, "Somatomedin: physiological control and effects on cell proliferation" *Handbook Exp. Pharmacol.* 57:161–208 (1981).

Clemmons et al., "Competition for binding to insulin–like growth factor (IGF) binding protein–2, 3, 4, and 5 by the IGFs and IGF analogs" *Endocrinology* 131(2):890–895 (Aug. 1992).

Clemmons et al., "Discrete Alterations of the Insulin–like Growth Factor I Molecular Which Alter Its Affinity for Insulin–like Growth Factor–binding Proteins Result in Changes in Bioactivity" *Journal of Biological Chemistry* 265(21):12210–12216 (1990).

Cwirla et al., "Peptides on phage: a vast library of peptides for identifying ligands" *Proc. Natl. Acad. Sci. USA* 87(16):6378–6382 (1990).

Devlin et al., "Random peptide libraries: a source of specific protein binding molecules" *Science* 249:404–406 (1990).

Duerr et al., "Insulin–like growth factor–1 enhances ventricular hypertrophy and function during the onset of experimental cardiac failure" *J. Clin. Invest.* 95:619–627 (1995).

Elahi et al., "Hemodynamic and metabolic responses to human Insulin–like growth factor I (IGF–I) in men" *Modern Concepts of Insulin–Like Growth Factors,* Spencer, EM, ed., New York: Elsevier Science Publ. Co. pp. 219–224 (1991).

Fielder et al., "Differential long–term effects of insulin–like growth factor–I (IGF–I) growth hormone (GH), and IGF–I plus GH on body growth and IGF binding proteins in hypophysectomized rats" *Endocrinology* 137:1913–1920 (1996).

Franklin et al., "Insulin–Like Growth Factor I Preserves Renal Function Postoperatively" *Am. J. Physiol.* 272:F257–F259 (1997).

Froesch et al., "Metabolic and Therapeutic Effects of Insulin–Like Growth Factor I" *Horm. Res.* 42:66–71 (1994).

Furnsinn et al., "Insulin–Like Growth Factor–I Inhibits Insulin and Amylin Secretion in Conscious Rats" *Endocrinology* 135(5):2144–2149 (1994).

Geysen et al., "A priori delineation of a peptide which mimics a discontinuous antigenic determinant" *Molecular Immunology* 23(7):709–715 (1986).

Ghazzi et al., "Cardiac and glycemic benefits of troglitazone treatment in NIDDM" *Diabetes* 46:433–439 (1997).

Giebel et al., "Screening of cyclic peptide phage libraries identifies ligands that bind streptavidin with high affinities" *Biochemistry* 34:15430–15435 (1995).

Guler et al., "Effects of Insulin–like Growth Factor I in Man" *Acta Paediatr. Scand.* 367:52–54 (Suppl. 1990).

Guler et al., "Effects of recombinant insulin–like growth factor I on insulin secretion and renal function in normal human subjects" *Proc. Natl. Acad. Sci. USA* 86:2868–2872 (Apr. 1989).

Guler et al., "Insulin–like growth factor I increases glomerular filtration rate and renal plasma flow in man" *Acta Endocrinologica* 121:101–106 (1989).

Guler et al., "Recombinant human insulin–like growth factor 1 stimulates growth and has distinct effects on organ size in hypophysectomized rats" *Proc. Natl. Acad. Sci. USA* 85:4889–4893 (1988).

Guler et al., "Short–term metabolic effects of recombinant human insulin–like growth factor I in healthy adults" *New England J. of Medicine* 317(3):137–140 (1987).

Hammerman and Miller, "The growth hormone insulin–like factor axis in kidney revisited" *Am. J. Physiol.* 265:F1–F14 (1993).

Hammerman and Miller, "Therapeutic use of growth factors in renal failure" *J. Am. Soc. Nephrol.* 5:1–11 (1994).

Hampton et al., "Purification and Characterization of an Insulin–like Growth Factor II Variant from Human Plasma" *Journal of Biological Chemistry* 264(32):19155–19160 (Nov. 15, 1989).

Hartman et al., "A low dose euglycemic infusion of recombinant human insulin–like growth factor I rapidly suppresses fasting–enhanced pulsatile growth hormone secretion in humans" *J. Clin. Invest.* 91:2453–2462 (1993).

Hasegawa et al., "The free form of insulin–like growth factor I increases in circulation during normal human pregnancy" *J. Clin. Endocrinol. Metabol.* 80:3284–3286 (1995).

Heding et al., "Biosensor measurement of the binding of insulin–like growth factors I and II and their analogues to the insulin–like growth factor–binding protein–3" *Journal of Biological Chemistry* 271(24):13948–13952 (Jun. 14, 1996).

Hirschberg et al., "Effects of insulin–like growth factor I on renal function in normal men" *Kidney International* 43:387–397 (1993).

Hizuka et al., "Measurement of free form of insulin–like growth factor I in human plasma" *Growth Regulation* 1:51–55 (1991).

Humbel, "Insulin–like growth factors I and II" *European Journal of Biochemistry* 190:445–462 (1990).

Jabri et al., "Adverse effects of recombinant human insulin–like growth factor I in obese insulin–resistant type II diabetic patients" *Diabetes* 43:369–374 (1994).

Johnson et al., "Underexpression of β cell high $K_m$ glucose transporters in noninsulin–dependent diabetes" *Science* 250:546–549 (1990).

Jones et al., "Insulin–Like Growth Factors and Their Binding Proteins: Biological Actions" *Endocrine Reviews* 16(1):3–34 (1995).

Juul et al., "Serum concentrations of free and total insulin–like growth factor–I, IGF binding proteins –1 and –3 and IGFBP–3 protease activity in boys with normal or precocious puberty" *Clin. Endocrinology* 44:515–523 (1996).

Kay et al., "An M13 phage library displaying random 38–amino–acid peptides as a source of novel sequences with affinity to selected targets" *Gene* 128:59–65 (1993).

Kerr et al., "Effect of Insulin–like Growth Factor 1 on the Responses to and Recognition of Hypoglycemia" *Diabetes: American Diabetes Association (ADA), San Antonio, Texas, Jun. 20–23, 1992* (abstract #225), 52nd Annual Meeting edition 41(supp 1):60A (Jun. 1992).

Kerr et al., "Effect of Insulin–like Growth Factor–1 on the Responses to and Recognition of Hypoglycemia in Humans" *J. Clin. Invest.* 91:141–147 (1993).

Kletzien et al., "Enhancement of adipocyte differentiation by an insulin–sensitizing agent" *Molecular Pharmacology* 41(2):393–398 (Feb. 1992).

Kupfer et al., "Enhancement of the anabolic effects of growth hormone and insulin–like growth factor I by use of both agents simultaneously" *J. Clin Invest.* 91:391–396 (1993).

Kuzuya et al., "Trial of insulinlike growth factor I therapy for patients with extreme insulin resistance syndromes" *Diabetes* 42:696–705 (1993).

Lassalle et al., "ESM–1 is a novel human endothelial cell–specific molecule expressed in lung and regulated by cytokines" *Journal of Biological Chemistry* 271:20458–20464 (1996).

Leahy et al., "Insulin–Like Growth Factor–I at Physiological Concentrations is a Potent Inhibitor of Insulin Secretion" *Endocrinology* 126(3):1593–1598 (1990).

Lee et al., "Insulin–Like Growth Factor (IGF) Binding Protein Complementary Deoxyribonucleic Acid from Human HEP G2 Hepatoma Cells: Predicted Protein Sequence Suggests an IGF Binding Domain Different from Those of the IGF–I and IGF–II Receptors" *Mol. Endocrinol.* 2(5):404–411 (1988).

Lee et al., "Regulation and function of insulin–like growth factor–binding protein–1" *Proc. Soc. Exp. Biol. & Med.* 204:4–29 (1993).

Leung et al., "Growth hormone receptor and serum binding protein: purification, cloning and expression" *Nature* 330:537–543 (1987).

Lewitt and Baxter, "Insulin–like growth factor–binding protein–1: a role in glucose counterregulation?" *Mol. Cell. Endocrinology* 79(1–3):C147–C152 (1991).

Lewitt et al., "Bioavailability of insulin–like growth factors (IGFs) in rats determined by the molecular distribution of human IGF–binding protein–3" *Endocrinology* 133:1797–1802 (1993).

Lewitt et al., "Insulin–like Growth Factor–binding Protein–1 Modulates Blood Glucose Levels" *Endocrinology* 129(4):2254–2256 (1991).

Lieberman et al., "Anabolic effects of recombinant insulin–like growth factor I in AIDS–associated cachexia" *US Endocrine Meeting* (Abstract 1664) pp. 466 (1993).

Lieberman et al., "Anabolic effects of recombinant insulin–like growth factor I in cachectic patients with the acquired immunodeficiency syndrome" *J. Clin. Endocrinol. and Metab.* 78(2):404–410 (1994).

Lieberman et al., "Effects of recombinant human insulin–like growth factor–I (rhIGF–I) on total and free IGF–I concentrations, IGF–binding proteins, and glycemic response in humans" *J. Clin. Endocrinol. and Metabl.* 75(1):30–36 (1992).

Livnah et al., "Functional mimicry of a protein hormone by a peptide agonist: the EPO receptor complex at 2.8 A" *Science* 273(5274):464–471 (Jul. 26, 1996).

Loddick et al., "Displacement of insulin–like growth factors from their binding proteins as a potential treatment for stroke" *Proc. Natl. Acad. Sci. USA* 95(4):1894–1898 (Feb. 17, 1998).

Lowman et al., "Molecular mimics of insulin–like growth factor 1 (IGF–I) for inhibiting IGF–I: IGF–binding protein interactions" *Biochemistry* 37(25):8870–8878 (1998).

Lowman et al., "Peptide that displace IGFs from their BPS as potential novel treament modalities of growth orders–basic aspects" (Abstract presented at the Intl. Pediatric Nephrology Assn.'s 6th Symposium on Growth and Development in Children with Chronic Renal Failure held in NY on Mar. 11–13, 1999).

Lowman, H., "Bacteriophage display and discovery of peptide leads for drug development" *Annual Review of Biophysics and Biomolecular Structure* 26:401–424 (1997).

Lowman, H., "Phage display of peptide libraries on protein scaffolds" *Methods in Molecular Biology*, Chapter 24, 87:249–264 (1998).

Maack et al., "Physiological Role of Silent Receptors of Atrial Natriuretic Factor" *Science* 238:675–678 (Oct. 30, 1987).

Martin & Baxter, "Insulin–like Growth Factor–binding Protein from Human Plasma. Purification and Characterization" *Journal of Biological Chemistry* 261(19):8754–8760 (1986).

McLafferty et al., "M13 bacteriophage displaying disulfide–constrained microproteins" *Gene* 128:29–36 (1993).

Miller et al., "Effects of IGF–I on renal function in end–stage chronic renal failure" *Kidney International* 46:201–207 (1994).

Morrow et al., "Recombinant Human (rh) IGF–I Reverses Hyperglycemia and Improves Insulin Sensitivity in Severe Insulin Resistance" *Diabetes–53rd Annual Meeting, Jun. 12–15, 1993* (abstract No. 269) 42:83A (Suppl. 1 1993).

O'Neil et al., "Identification of novel peptide antagonists for GPIIb/IIIa from a conformationally constrained phage peptide library" *Proteins: Structure, Function, and Genetics* 14:509–515 (1992).

O'Shea and Layish, "Growth hormone and the kidney: a case presentation and review of the literature" *J. Am. Soc. Nephrol.* 3:157–161 (1992).

O'Shea et al., "Effects of IGF–I on renal function in patients with chronic renal failure" *Am. J. Physiol.* 264:F917–F922 (1993).

Oh et al., "Characterization of the affinities of insulin–like growth factor (IGF)–binding proteins 1–4 for IGF–I, IGF–II IGF–I/insulin hybrid, and IGF–I analogs" *Endocrinology* 132:1337–1344 (1993).

Oh et al., "Synthesis and characterization of insulin–like growth factor–binding protein (IGFBP)–7. Recombinant human mac25 protein specifically binds IGF–I and –II" *Journal of Biological Chemistry* 271:30322–30325 (1996).

Oldenburg et al., "Peptide ligands for a sugar–binding protein isolated from a random peptide library" *Proc. Natl. Acad. Sci.* 89:5393–5397 (1992).

Peterkofsky et al., "Elevated Activity of Low Molecular Weight Insulin–Like Growth Factor–Binding Proteins in Sera of Vitamin C–Deficient and Fasted Guinea Pigs" *Endocrinology* 128(4):1769–1779 (1991).

Phelan et al., "A General Method for Constraining Short Peptides to an α–Helical Conformation" *J. Am. Chem. Soc.* 119(3):455–460 (Jan. 22, 1997).

Quin et al., "Acute Response to Recombinant Insulin–like Growth Factor I in a Patient with Mendenhall's Syndrome" *New England J. of Medicine* 323:1425–1426 (1990).

Rinderknecht and Humbel, "Polypeptides with nonsuppressible insulin–like and cell–growth promoting activities in human serum: isolation, chemical characterization, and some biological properties of form I and II" *Proc. Natl. Acad. Sci USA* 73(7):2365–2369 (1976).

Rinderknecht and Humbel, "The amino acid sequence of human insulin–like growth factor I and its structural homology with proinsulin" *Journal of Biological Chemistry* 253(8):2769–2776 (1978).

Ross et al., "The Role of Insulin, Growth Hormone and IGF–I as Anabolic Agents in the Critically Ill" *Intensive Care Med.* 19(2):S54–S57 (Suppl. 1993).

Rudinger, J., "Characteristics of the Amino Acids as Components of a Peptide Hormone Sequence" *Peptide Hormones*, J. A. Parsons, Baltimore:University Park Press pp. 1–7 (1976).

Saad et al., "Low–doses of Insulin–like Growth Factor–I Improve Insulin Sensitivity" *Diabetologia* (Abstract 152) 37:A40 (Supp. 1 1994).

Schlach et al., "Short–Term Effects of Recombinant Human Insulin–Like Growth Factor I on Metabolic Control of Patients with Type II Diabetes Mellitus" *J. of Clinical Endocrinology & Metabolism* 77(6):1563–1568 (1993).

Schalch et al., "Short–Term metabolic effects of recombinant human insulin–like growth factor I (rhIGF–I) in type II diabetes mellitus" *Modern Concepts of Insulin–Like Growth Factors*, Spencer, ed., New York:Elsevier Science Publ. Co. pp. 705–713 (1991).

Schoen et al., "Growth Hormone Secretagogues" *Annual Reports in Medicinal Chemistry: Section IV–Immunology, Endocrinology & Metabolic Diseases*, William K. Hagmann, Chapter 19, vol. 28:177–186 (1993).

Schoenle et al., "Recombinant human insulin–like growth factor I(rhIGF I) reduces hyperglycaemia in patients with extreme insulin resistance" *Diabetologia* 34:675–679 (1991).

Scott and Smith, "Searching for peptide ligands with an epitope library" *Science* 249:386–390 (1990).

Sherwin et al., "Metabolic Effects of Insulin–like Growth Factor I in Normal Humans" *Horm. Res.* 41:97–101 (Suppl. 2 1994).

Skottner et al., "Growth responses in a mutant dwarf rat to human growth hormone and recombinant human insulin–like growth factor I" *Endocrinology* 124(5):2519–2526 (1989).

Smith, "Filamentous fusion phage: novel expression vectors that display cloned antigens on the virion surface" *Science* 228 (4705):1315–1317 (1985).

Stern et al., "Insulin Resistance and pancreatic insulin release in the genetically obese Zucker rat" *Proc. Soc. Exp. Biol. Med.* 139:66–69 (1972).

Suikkari et al., "Insulin regulates the serum levels of low molecular weight insulin–like growth factor–binding protein" *J. Clin. Endocrinology Metabol.* 66:266–272 (1988).

Swisshelm et al., "Enhanced expression of an insulin growth factor–like binding protein (mac25) in senescent human mammary epithelial cells and induced expression with retinoic acid" *Proc. Natl. Acad. Sci.* 92:4472–4476 (1995).

Takano et al., "Effects of sc Administration of Recombinant Human Insulin–like Growth Factor I (IGF–I) on Normal Human Subjects" *Endocrinol. Japan* 37(2):309–317 (1990).

Tanner et al., "Comparative rapidity of response of height, limb muscle and limb fat to treatment with human growth hormone in patients with and without growth hormone deficiency" *Acta Endocrinologica* 84:681–696 (1977).

Underwood et al., "Regulation of somatomedin–c/insulin–like growth factor I by nutrients" *Hormone Res.* 24:166–176 (1986).

Usala et al., "Brief report: treatment of insulin–resistant diabetic ketoacidosis with insulin–like growth factor I in an adolescent with insulin–dependent diabetes" *New England J. of Medicine* 327(12):853–857 (1992).

Uthne et al., "Effects of human somatomedin preparations on membrane transport and protein synthesis in the isolated rat diaphragm" *J. Clin. Endocrinol. Metab.* 39(3):548–554 (1974).

Van Wyk et al., "The somatomedins: a family of insulinlike hormones under growth hormone control" *Recent Prog. Horm. Res.* 30:259–318 (1974).

Valchopapadopoulou et al., "Metabolic and Clinical Response to Recombinant Human Insulin–like Growth Factor I in Myotonic Dystrophy—A Clinical Research Center Study" *J. Clin. Endo. Metabl.* 80(12):3715–3723 (1995).

Wells and Lowman, "Rapid Evolution of Peptide and Protein Binding Properties in Vitro" *Curr. Opin. Struct. Biol.* 2:597–604 (1992).

Wilton et al., "Treatment with recombinant human insulin–like growth factor I of children with growth hormone receptor deficiency (Laron syndrome)" *Acta Paediatr Suppl.* 383:137–142 (1992).

Wood et al., "Cloning and expression of the growth hormone–dependent insulin–like growth factor–binding protein" *Molecular Endocrinology* 2:1176–1185 (1988).

Wood et al., "Crystal structure analysis of deamino–oxytocin: conformational flexibility and receptor binding" *Science* 232:633–636 (1986).

Wrighton et al., "Small peptides as potent mimetics of the protein hormone erythropoietin" *Science* 273:458–463 (1996).

Yamauchi et al., "Purification and molecular cloning of prostacyclin–stimulating factor from serum–free conditioned medium of human diploid fibroblast cells" *Biochemical Journal* 303 (Part 2): 591–598 (1994).

Zenobi et al., "Effects of insulin–like growth factor–I on glucose tolerance, insulin levels, and insulin secretion" *J. Clin. Invest.* 89:1908–1913 (1992).

Zenobi et al., "Insulin–like growth factor–I improves glucose and lipid metabolism in type 2 diabetes mellitus" *J. Clin. Invest.* 90:2234–2241 (1992).

* cited by examiner

```
TCACGTAAAA AGGGTATCTA GAATTATGAT GATTACTCTG CGCAAACTTC CTCTGGCGGT TGCCGTCGCA GCGGGCGTAA TGTCTGCTCA GGCCATGGCC
AGTGCATTTT TCCCATAGAT CTTAATACTA CTAATGAGAC GCGTTTGAAG GAGACCCGCA ACGGACCGGT CGCCCGCCATT ACAGACGAGT CCGGTACCGG
                    MetMe tIleThrLeu ArgLysLeuP roLeuAlaVa lAlaValAla AlaGlyValM etSerAlaGl nAlaMetAla
                    ^Start of lamB signal sequence GGTCCCGAAA CTCTGTGCGG TGCTGAACTG GTTGACGCGTC TGCAGTTCGT ATGTGGTGAT CGAGGCTTCC TGTTCAACAA ACCGACTGGG GCTGATCCT
CCAGGGCTTT GAGACACGCC ACGACTTGAC CAACTGCGAG AGTCAAGCA TACACCACTA GCTCCGAAGG ACAAGTTGTT TGGCTGACCC CGACCTAGGA
GlyProGluT hrLeuCysGl yAlaGluLeu ValAspAlaL euGlnPheVa lCysGlyAsp ArgGlyPheL euPheAsnLy sProThrGly AlaGlySerSer
^Start of IGF-I (Y24L,Y31A)

CCTCTCGTCG TGCTCCCCAG ACTGGTATTG CTGCTTTCGT TCTTGGACCC TGCCGTCGTCT GGAAATGTAT TGCGCTCCCC TGAAACCCGC
GGAGAGCAGC ACGAGGGGTC TGACCATAAC AACTGCTTAC GACGAAAGCA AGAACCTGG ACGCAGCAGA CCTTTACATA ACGCAGGGG ACTTTGGGCG
SerArgAr gAlaProGln ThrGlyIleV alAspGluCy sCysPheArg SerCysAspL euArgArgLe uGluMetTyr CysAlaProL euLysProAla

TAAATCTGCT TAGAAGCTCC TAACGCTCGG TTGCCCGCCGG GCGTTTTTTA TTGTTAACTC ATGTTTGACA GCTTATCATC GATAAGCTTT AATGCGGTAG
ATTTAGACGA ATCTTCGAGG ATTGCGAGCC AACGGGCGGCC CGCAAAAAAT AACAATTGAG TACAAACTGT CGAATAGTAG CTATTCGAAA TTACGCCATC
LysSerAla Am*
```

Nucleotide and Amino Acid Sequence of the LamB Signal Sequence and IGF-I (Y24L,Y31A)

FIG. 1 plasmid IGFMI
length: 5115 (circular)

```
   1 GAATTCAACT TCTCCATACT TTGGATAAGG AAATACAGAC ATGAAAAATC TCATTGCTGA GTTGTTATTT AAGCTTGCCC AAAAAGAAGA AGAGTCGAAT
     CTTAAGTTGA AGAGGTATGA AACCTATTCC TTTATGTCTG TACTTTTTAG AGTAACGACT CAACAATAAA TTCGAACGGG TTTTTCTTCT TCTCAGCTTA

101 GAACTGTGTG CGCAGGTAGA AGCTTTGGAG ATTATCGTCA CTGCAATGCT TCGCAAATAT GCGCAAAATG ACCAACAGCG GTTGATTGAT CAGGTAGAGG
     CTTGACACAC GCGTCCATCT TCGAAACCTC TAATAGCAGT GACGTTACGA AGCGTTTATA CGCGTTTTAC TGGTTGTCGC CAACTAACTA GTCCATCTCC

201 GGGCGCTGTA CGAGTGAAAG CCCGATGCCA GCATTCCTGA CGACGATACG GAGCTGCTGC GCGATTACGT AAAGAAGTTA TTGAAGCATC CTCGTCAGTA
     CCCGCGACAT GCTCCATTTC GGGCTACGGT CGTAAGGACT GCTGCTATGC CTCGACGACG CGCTAATGCA TTTCTTCAAT AACTTCGTAG GAGCAGTCAT

301 AAAAGTTAAT CTTTTCAACA GTCTGTCACG GCCGAGACTT ATAGTCGCTT TGTTTTTATT TTTTGTAACTA GTACGCAAGT
     TTTTCAATTA GAAAAGTTGT CGACAGTATT TCAACAGTGC CGGCTCTGAA TATCAGCGAA ACAAAAATAA AAAATTACAT CATGCGTTCA

401 TCACGTAAAA AGGGTATCTA GAATTATGAT CTCTGGGCGT CGCAAACTTC TGCCGTCGCA GCGGGCGTAA TGTCTGCTCA GGCCATGGCC
     AGTGCATTTT TCCCATAGAT CTTAATACTA GAGACCCGCA GCGTTTGAAG ACGGCAGCGT CGCCCGCATT ACAGACGAGT CCGGTACCGG
                      MetMe tIleThrLeu ArgLysLeuP roLeuAlaVa lAlaValAla AlaGlyValM etAlaMetAl

501 GGTCCCGAAA CTCTGTGCGG CTCTGAACTG GTTGACGCTC TGCAGTTCGT ATGTGGTGAT CGAGGCTTCC TGTTCAACAA ACCGACTGGG GCTGATCCT
     CCAGGGCTTT GAGACACGCC GAGACTTGAC CAACTGCGAG ACGTCAAGCA TACACCACTA GCTCCGAAGG ACAAGTTGTT TGGCTGACCC CGACTAGGA
  26 GlyProGluT hrLeuCysGl yAlaGluLeu ValAspAlaL euGlnPheVa lCysGlyAsp ArgGlyPheL euPheAsnLy sProThrGly AlaGlySerSer

601 CCTCTCGTCG TGCTCCCCAG ACTGGTATTG TTGACGAATG CTGCTTTCGT TCTTGCGACC TGCGTCGTCT GGAAATGTAT TGCCCTCCCC TGAAACCCGC
     GGAGAGCAGC ACGAGGGGTC TGACCATAAC AACTGCTTAC GACGAAAGCA AGAACGCTGG ACGCAGCAGA CCTTTACATA ACGGGAGGGG ACTTTGGGCG
  60 SerArgAr gAlaProGln ThrGlyIleV alAspGluCy sCysPheArg SerCysAspL euArgArgLe euGluMetTyr CysAlaProL euLysProAla

701 TAAAATCTGCT TAGAAGCTCC TAACGCTCGG TTGCCGCCGG TTGTTAACTC ATGTTTGACA GCTTATCATC GATAAGCTTT AATGCGGTAG
     ATTTTAGACGA ATCTTCGAGG ATTGCGAGCC AACGGCGGCC AACAATTGAG TACAAACTGT CGAATAGTAG CTATTCGAAA TTACGCCATC
  93 LysSerAla Am*

801 TTTATCACAG TTAAATTGCT ATGAAATCTA ACAATGCGCT CTCGGCACCG TCACCCTGA TGCTGTAGGC
     AATATGTGTC AATTTAACGA TACTTTAGAT TGTTACGCGA GAGCCGTGGC AGTGGGACCT ACGACATCCG

901 ATAGGCTTGG TTATGCCGGT ACTGCTGGGC ATATCGTCCA TTCCGACAGC ATCGCCAGTG ACTATGGCGT GCTGCTAGCG CTATATCGT
     TATCCGAACC AATACGGCCA TGACGACCCG TATAGCAGGT AAGGCTGTCG TAGCGGTCAC TGATACCGCA CGACGATCGC GATATACGCA

1001 TGATGCAATT TCTATGCGCA CCCGTTCTCG GAGCACTGTC CGACCGCTTT GGCCGCCGCC CAGTGCTGCT CGCTTCGCTA CTTGGAGCCA CTATCGACTA
     ACTACGTTAA AGATACGCGT GGGCAAGAGC CTCGTGACAG GCTGGCGAAA CCGGCGGCGG GTCAGGACGA GCGAAGCGAT GAACCTCGGT GATAGCTGAT
```

FIG. 3A

```
1101  CGCGATCATG  GCGACCACAC  CCGTCCTGTG  GATCCTCTAC  GCCGGACGCA  TCGTGGCCGG  CATCACCGGC  GCCACAGGTG  CGGTTGCTGG  CGCCTATATC
      GCGCTAGTAC  CGCTGGTGTG  GGCAGGACAC  CTAGGAGATG  CGGCCTGCGT  AGCACCGGCC  GTAGTGGCCG  CGGTGTCCAC  GCCAACGACC  GCGGATATAG

1201  GCCGACATCA  CCGATGGGAA  AGATCGGGCT  CGCCACTTCG  GGCTCATGAG  CGCTGTTTC   GGCGTGGGTA  TGGTGGCAGG  CCCCGTGGCC  GGGGACTGT
      CGGCTGTAGT  GGCTACCCCT  TCTAGCCCGA  GCGGTGAAGC  CCGAGTACTC  GCGAACAAAG  CCGCACCCAT  ACCACCGTCC  GGGGCACCGG  CCCCTGACA

1301  TGGGCGCCAT  CTCCTTGCAT  GCACCATTCC  TTGCGGCGGC  GGTGCTCAAC  GGCCTCAACC  CTGCTTCCTA  ATGCAGGAGT  CGCATAAGGG
      ACCCGCGGTA  GAGGAACGTA  CGTGGTAAGG  AACGCCGCCG  CCACGAGTTG  CCGGAGTTGG  GACGAAGAT   TACGTCCTCA  GCGTATTCCC

1401  AGAGCGTCGA  CCGATGCCCT  TGAGAGCCTT  CAACCCAGTC  AGCTCCTTCC  GGTGGGCGCG  GGGCATGACT  ATCGTCGCCG  CACTTATGAC  TGTCTTCTTT
      TCTCCGCAGCT GGCTACGGGA  ACTCTCGGAA  GTTGGGTCAG  TCGAGGAAGG  CCACCCGCGC  CCCGTACTGA  TAGCAGGGGC  GTGAATACTG  ACAGAAGAAA

1501  ATCATGCAAC  TCGTAGGACA  GGTGCCGGCA  GCGCTCTGGG  TCATTTTCGG  CGAGGACCGC  TTTCGCTGGA  GCGCGACGAT  GATCGGCCTG  TCGCTTGCGG
      TAGTACGTTG  AGCATCCTGT  CCACGGCCGT  CGCGAGACCC  AGTAAAAGCC  GCTCCTGGCG  AAAGCGACCT  CGCGCTGCTA  CTAGCCGGAC  AGCGAACGCC

1601  TATTCGGAAT  CTTGCACGCC  CCTTCGTCAC  TGGTCCCGCC  ACCAAACGTT  TCGGCGAGAA  GCAGGCCATT  ATCGCCGGCA  TGGCGCCCGA
      ATAAGCCTTA  GAACGTGCGG  GGAAGCAGTG  ACCAGGCGG   TGGTTTGCAA  AGCCGCTCTT  CGTCCGGTAA  TAGCGGCCGT  ACCGCCGGCT

1701  CGCGCTGGGC  TACGTCTTGC  TGGCGTTCGC  GACGCGAGGC  TGGATGGCCT  TCCCCATTAT  GATTCTCTC   GCTTCCGGCG  GCATCGGGAT  GCCGCGTTG
      GCGCGACCCG  ATGCAGAACG  ACCGCAAGCG  CTGCGCTCCG  ACCTACCGGA  AGGGTAATA   CTAAGAAGAG  CGAAGGCCGC  CGTAGCCCTA  CGGGCGCAAC

1801  CAGGCCATGC  TGTCCAGGCA  GGTAGATGAC  GACAGCTTCA  AGATCGCTC   CCAGCCTAAC  GCGGCTCTTA  TTCGATCACT  GGACCGCTGA
      GTCCGGTACG  ACAGTTCCGT  CCATCTACTG  CTGTCGAAGT  TCCTAGCGAG  GGTCGGATTG  CGCCGAGAAT  AAGCTAGTGA  CCTGGCACT

1901  TCGTCACGGC  GATTTATGCC  GCCTCGGCGA  GCACATGGAA  CGGGTTGGCA  TGGATTGTAG  GCGCGCCCT   ATACCTTGTC  TGCCTCCCCG  CGTTGCGTCG
      AGCAGTGCCG  CTAAATACGG  CGGAGCCGCT  CGTGTACCTT  GCCCAACCGT  ACCTAACATC  CGCGCGGGA   TATGGAACAG  ACGGAGGGGC  GCAACGCAGC

2001  CGGTGCATGG  AGCCGGGCCA  CCTCGACCTG  AATGGAAGCC  GGCGGCACCT  TTCACCACTC  CAAGAATTGG  AGCCAATCAA  TTCTTGCGGA
      TCGGCCGTAC  TCGGCCCGGT  GGAGCTGGAC  TTACCTTCGG  CCGCCGTGGA  AAGTGGTGAG  GTTCTTAACC  TCGGTTAGTT  AAGAACGCCT

2101  GAACTGTGAA  TGCGCAAACC  AGAACATATC  GTTGAGGACC  GCCATCTCCA  GCAGCCCGCAC GGGCGCATC   TCGGGCAGCG  TTGGGTCCTG
      CTTGACACTT  ACGCGTTTGG  TCTTGTATAG  CAACTCCGA   CGGTAGAGGT  CGTCGGGCGTG CGCCGCGTAG  AGCCCGTCGC  AACCCAGGAC

2201  GCCACGGGTG  CGCATGATCG  TGCTCCTGTC  CGGCTAGGACC CCTTACTGGT  TAGCAGAATG  AATCACCGAT  ACGCGAGCGA
      CGGTGCCCAC  GCTACTAGC   ACGAGGACAG  GCCGATCCGA  GGAATGACCA  ATCGTCTTAC  TTAGTGCCTA  TGCGCTTCGCT

2301  ACGTGAAGCG  ACTGCTGCTG  CAAAACGTCT  GCGACCTGAG  CAACAACATG  GGTTTCCGTG  TTTCGTAAAG  TCTGGAAACG  CGGAAGTCAG
      TGCACTTCGC  TGACGACGAC  GTTTTGCAGA  CGCTGGACTC  GTTGTTGTAC  CCAAAGGCAC  AAAGCATTTC  AGACCTTTGC  GCCTTCAGTC

2401  CGCCTGAAGC  CATTATGTTC  CGGATCTGCA  TCGCAGGATG  CTGCTGGCTA  CCCTGTGAA   CACCTTACATC TGTATTAACG  AAGGCGTGGC  ATTGACCCTG
      GCGGGACGTG  GTAATACAAG  GCCTAGACGT  AGCGTCCTAC  GACGACCGAT  GGGACACTT   GTGGATGTAG  ACATAATTGC  TTCCGACCG   TAACTGGGAC
```

FIG. 3B

```
2501 AGTGATTTTT CTCTGGTCCC GCCGCATCCA TACCGCCAGT TGTTTACCCT CACAACGTTC CAGTAACCGG GCATGTTCAT CATCAGTAAC CCGTATCGTG
     TCACTAAAAA GAGACCAGGG CGGCGTAGGT ATGGCGGTCA ACAAATGGGA ACAAATGGGA GTGTTGCAAG GTCATTGGCC GTACAAGTA GGCATAGCAC

2601 AGCATCCTCT CTCGTTTCAT CGGTATCATT ACCCCCATGA ACAGAAATTC CCCCTTACAC GGAGGCATCA AGTGACCAAA CAGGAAAAA CCGCCCTTAA
     TCGTAGGAGA GAGCAAAGTA GCCATAGTAA TGGGGGTACT TGTCTTTAAG GGGGAATGTG CCTCCGTAGT TCACTGGTTT GTCCTTTTTT GGCGGGAATT

2701 CATGGCCCGC TTTATCAGAA GCCAGACATT AACGCTTCTG GAGAAACTCA ACGAGCTGGA CGCGAGATGAA CAGGCAGACA TCTGTGAATC GCTTCACGAC
     GTACCGGGCG AAATAGTCTT CGGTCTGTAA TTGCGAAGAC CTCTTTGAGT TGCTCGACCT GCGCTACTT GTCCGTCGT AGACACTTAG CGAAGTGCTG

2801 CACGCTGATG AGCTTTACCG GCGCGTTTCG GTGATGACGG TGAAACCCTC TGACACATGC AGCTCCCGA GACGGTCACA GCTGTCTGT
     GTGCGACTAC TCGAAATGGC CGCGCAAAGC CACTACTGCC ACTTTTGGAG ACTGTGTACG TCGAGGGCCT CTGCCAGTGT CGAACAGACA

2901 AAGCGGATGC CGGGAGCAGA CAAGCCCGTC AGCGGCGTGT GGGGCGCAGC CATGACCCAG GGGCGGTGTC AGCTTGGGAC TCACGTAGCG ATAGCGGAGT
     TTCGCCTACG GCCCTCGTCT GTTCGGGCAG TCGCCGCACA CCCCGCACG CCCCGCGTCG GTACTGGGTC CCGCCACAA AGTGCATCGC TATCGCCTCA

3001 GTATACTGGC TTAACTATGC GGCATCAGAG CAGATTGTAC TGAGAGTGCA CCATATGCGG TGTGAAATAC CGTAAGGAGA AAATACCGCA
     CATATGACCG AATTGATACG CCGTAGTCTC GTCTAACATG ACTCTCACGT GGTATACGCC ACACTTTATG GCATTCCTCT TTTATGCGT

3101 TCAGGCCTC TTCCGCTTCC ACTCGCTGCG CTCGGTCGTT AAGGCCCAGC AAAGGCCAGC GAGCCGTATC AAGGCGGTAA TACGGTTATC
     AGTCCGGAG AAGGCGAAGG AGCGAGTGAC GAGCCAGCAA TTCCGGTCG GAGCGATGAG AGCGAT TCGAGTGAGT TTCCGCCATT ATGCCAATAG

3201 CACAGAATCA GGGGATAACG CAGGAAAGAA CATGTGAGCA AAAGGCCAGC AAAAGGCCAGC AAAAGGCCAGC AAAGGCCTAAA TGCTGGCGTT TTTCCATAGG
     GTGTCTTAGT CCCCTATTGC GTCCTTTCTT GTACACTCGT TTTCCGGTCG TTTCCGGTCG TTTCCGGTCG TTTCCGCATT ACGACCGCAA AAGGTATCC

3301 CTCCGCCCCC CTGACGAGCA TCACAAAAAT CGACGCTCAA GTCAGAGGTG GCGAAACCCG ACAGGACTAT AAAGATACCA GGCGTTTCCC CCTGGAAGCT
     GAGGCGGGGG GACTGCTCGT AGTGTTTTTA GCTGCGAGTT CAGTCTCCAC CGCTTTGGGC TGTCCTGATA TTTCTATGGT CCGCAAAGGG GGACCTTCGA

3401 CCCTCGTGCG CTCTCCTGTT CCGACCCTGC CGCTTACCGG ATACCTGTCC GCCTTTCTCC CTTCGGGAAG CGTGGCGCTT TCTCATAGCT CACGCTGTAG
     GGGAGCACGC GAGAGGACAA GGCTGGGACG GCGAATGGCC TATGGACAGG GGAAAGAGGG GAAGCCCTTC GCACCGCGAA AGAGTATCGA GTGCGACATC

3501 GTATCTCAGT TCGGTGTAGG TCGTTCGCTC CAAGCTGGGC TGTGTGCACG AACCCCCCGT TCAGCCCGAC TCAGCCCGAC TATCCGGTAA CTATCGTCTT
     CATAGAGTCA AGCCACATCC AGCAAGCGAG GTTCGACCCG ACACACGTGC TTGGGGGGCA AGTCGGGCTG GCGCGGA ATAGGCCATT GATAGCAGAA

3601 GAGTCCAACC CGGTAAGACA CGACTTATCG CCACTGGCAG CAGCCACTGG TAACAGGATT AGCAGAGCGA GGTATGTAGG CGGTGCTACA GAGTTCTTGA
     CTCAGGTTGG GCCATTCTGT GCTGAATAGC GGTGACCGTC GTCGGTGACC ATTGTCCTAA TCGTCTCGCT CCATACATCC GCCACGATGT CTCAAGAACT

3701 AGTGGTGGCC TAACTACGGC TACACTAGAA GGACAGTATT TGGTATCTGC GCTCTGCTGA AGCCAGTTAC CTTCGGAAAA AGAGTTGGTA GCTCTTGATC
     TCACCACCGG ATTGATGCCG ATGTGATCTT CCTGTCATAA ACCATAGACG CGAGACGACT TCGGTCAATG GAAGCCTTTT TCTCAACCAT CGAGAACTAG
```

FIG. 3C

```
3801  CGGCAAACAA ACCACCGCTG GTAGCGGTGG TTTTTTGTT TGCAAGCAGC AGATTACGCG CAGAAAAAAA GGATCTTCAAG AAGATCCTTT GATCTTTTCT
      GCCGTTTGTT TGGTGGCGAC CATCGCCACC AAAAAAACAA ACGTTCGTCG TCTAATGCGC GTCTTTTTTT CCTAGAGTTC TTCTAGGAAA CTAGAAAAGA

3901  ACGGGGTCTG ACGCTCAGTG GAACGAAAAC CTTGCTTTTG TCACGTTAAG AGTGCAATTC GGATTTTGGT CATGAGATTA TCAAAAAGGA TCTTCACCTA GATCCTTTTA AATAAAAAT
      TGCCCCAGAC TGCGAGTCAC CTTGCTTTTG GAACGAAAAC AGTGCAATTC TCACGTTAAG CCTAAAACCA GTACTCTAAT AGTTTTCCT AGAAGTGGAT CTAGGAAAAT TTAATTTTTA

4001  GAAGTTTTAA ATCAATCTAA AGTATATATG AGTAAACTTG GTCTGACAGT TACCAATGCT TAATCAGTGA GGCACCTATC TCAGCGATCT GTCTATTTCG
      CTTCAAAATT TAGTTAGATT TCATATATAC TCATTTGAAC CAGACTGTCA ATGGTTACGA ATTAGTCACT CCGTGGATAG AGTCGCTAGA CAGATAAAGC

4101  TTCATCCATA GTTGCCTGAC TCCCCGTCGT GTAGATAACT ACGATACGGG AGGGCTTACC ATCTGGCCCC AGTGCTGCAA TGATACCGCG AGACCCACGC
      AAGTAGGTAT CAACGGACTG AGGGGCAGCA CATCTATTGA TGCTATGCCC TCCCGAATGG TAGACCGGGG TCACGACGTT ACTATGGCGC TCTGGGTGCG

4201  TCACCGGCTC CAGATTTATC AGCAATAAAC CAGCCAGCCG GAAGGGCCGA GCGCAGAAGT GGTCCTGCAA CTTTATCCGC CTCCATCCAG TCTATTAATT
      AGTGGCCGAG GTCTAAATAG TCGTTATTTG GTCGGTCGGC CTTCCCGGCT CGCGTCTTCA CCAGGACGTT GAAATAGGCG GAGGTAGGTC AGATAATTAA

4301  GTTGCCGGGA AGTAGAGTA AGTAGTTCGC CAGTTAATAG TTTGCGCAAC GTTGTTGCCA TTGCTGCAGG CATCGTGGTG TCACGCTCGT CGTTTGGTAT
      CAACGGCCCT TCATCTCAT TCATCAAGCG GTCAATTATC AAACGCGTTG CAACAACGGT AACGACGTCC GTAGCACCAC AGTGCGAGCA GCAAACCATA

4401  GGCTTCATTC AGCTCCGGTT CCCAACGATC AAGGCGAGTT CCATGTGTG CCATGTGTG TAATTCTCTT ACTGTCATGC GTTAGCTCCT TCGGTCCTCC GATCGTTGTC
      CCGAGTAAG TCGAGGCCAA GGGTTGCTAG TTCCGCTCAA TGTACTAGGG GGTACAACAC GTTTTTCGC TGACAGTACG CAATCGAGGA AGCCAGGAGG CTAGCAACAG

4501  AGAAGTAAGT TGGCCGCAGT GTTATCACTC ATGGTTATGG CAGCACTGCA TAATTAAGAA CATCCGTAAG CATCCGTAAG ATGCTTTTCT GTGACTGGTG
      TCTTCATTCA ACCGGCGTCA CAATAGTGAG TACCAATACC GTCGTGACGT ATTAAGAGAA TGACAGTACG GTAGGCATTC TACGAAAAGA CACTGACCAC

4601  AGTACTCAAC CAAGTCATTC TGAGAATAGT GTATGCGGCG ACCGAGTTGC TCTTGCCCGG CGTCAACACG GGATAATACC GCGCCACATA GCAGAACTTT
      TCATGAGTTG GTTCAGTAAG ACTCTATCA CATACGCCGC TGGCTCAACG AGAACGGGCC GCAGTTGTGC CCTATTATGG CGCGGTGTAT CGTCTTGAAA

4701  AAAAGTGCTC ATCATTGGAA AACGTTCTTC GGGGCGAAAA CTCTCAAGGA TCTTACCGCT GTTGAGATCC AGTTCGATGT AACCCACTCG TGCACCCAAC
      TTTTCACGAG TAGTAACCTT TTGCAAGAAG CCCCGCTTTT GAGAGTTCCT AGAATGGCGA CAACTCTAGG TCAAGCTACA TTGGGTGAGC ACGTGGGTTG

4801  TGATCTTCAG CATCTTTTAC TTTCACCAGC GTTTCTGGGT GAGCAAAAAC AAGAAGGCAA AATGCCGCAA AAAAGGGAAT AAGGGCGACA CGGAAATGTT
      ACTAGAAGTC GTAGAAAATG AAAGTGGTCG CAAAGACCCA CTCGTTTTTG TTCTTCCGTT TTACGGCGTT TTTTCCCTTA TTCCCGCTGT GCCTTTACAA

4901  GAATACTCAT ACTCTTCCTT TTTCAATATT ATTGAAGCAT TATCAGGGT TATTGTCTCA CATATTTGAA TGTATTTAGA AAATAAACA
      CTTATGAGTA TGAGAAGGAA AAAGTTATAA TAACTTCGTA ATAACAGAGT ACTCGCCTAT GTATAAACTT ACATAAATCT TTTTATTTGT

5001  AATAGGGGTT CCGCGCACAT TTCCCCGAAA AGTGCCACCT GACGTCTAAG AAACCATTAT TATCATGACA TTAACCTATA AAAATAGGCG TATCACGAGG
      TTATCCCCAA GGCGCGTGTA AAGGGGCTTT TCACGGTGGA CTGCAGATTC TTTGGTAATA ATAGTACTGT AATTGGATAT TTTTATCCGC ATAGTGCTCC

5101  CCCTTTCGTC TTCAA
      GGGAAAGCAG AAGTT
```

FIG. 3D

—□— Control     —●— IGF-Mutant

— ● — IGF-1 (150 μg, tid)
— □ — IGF Mutant (150 μg, tid)
— ○ — IGF Mutant (50 μg, tid)
— ▲ — Excipient Control

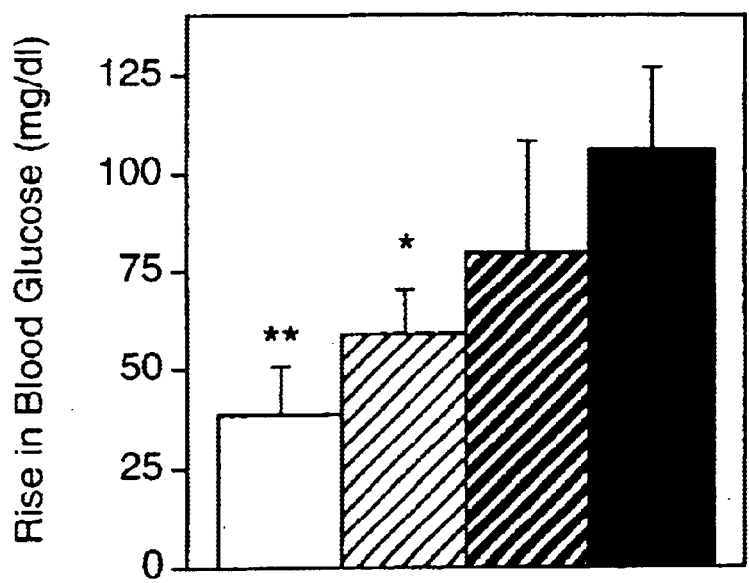
FIG. 23A
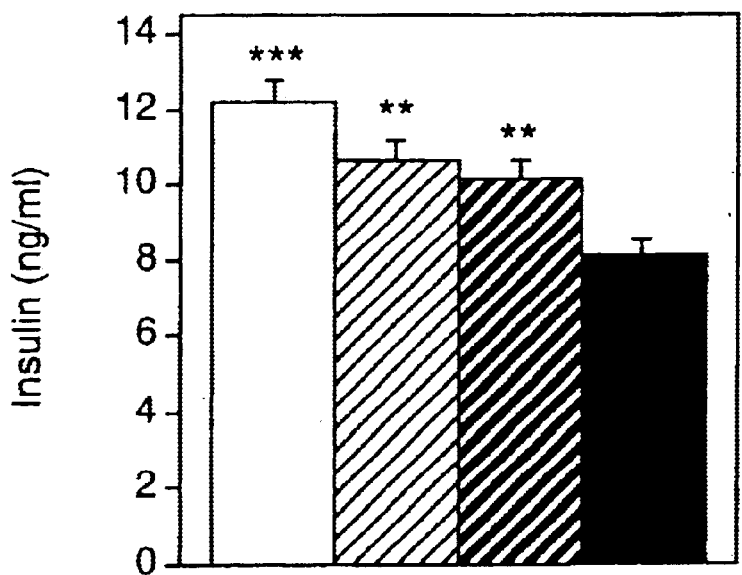
FIG. 23B   ☐ IGF-1 (150 µg, tid)   ▨ IGF-Mutant (150 µg, tid)
▨ IGF-Mutant (50 µg, tid)   ■ Control

```
plasmid t4.g8
length: 5140 (circular)

1 GAATTCAACT TCTCCATACT TTGGATAAGG AAATACAGAC ATGAAAAATC TCATTGCTGA GTTGTTATTT AAGCTTGCCC AAAAAGAAGA AGAGTCGAAT
     CTTAAGTTGA AGAGGTATGA AACCTATTCC TTTATGTCTG TACTTTTTAG AGTAACGACT CAACAATAAA TTCGAACGGG TTTTTCTTCT TCTCAGCTTA

101 GAACTGTGTG CGCAGGTAGA AGCTTTGGAG ATTATCGTCA CTGCAATGCT TCGCAAATAT GCGCAAAATG ACCAACAGCG GTTGATTGAT CAGGTAGAGG
     CTTGACACAC GCGTCCATCT TCGAAACCTC TAATAGCAGT GACGTTACGA AGCGTTATAC CGCGTTTTAC TGGTTGTCGC CAACTAACTA GTCCATCTCC

201 GGGCGCTGTA CGAGGTAAAG CCCGATGCCA GCATTCCTGA CGACGATACG GAGCTGCTGC GCGATTACGT AAAGAAGTTA TTTGAAGCATC CTCGTCAGTA
     CCCGCGACAT GCTCCATTTC GGGCTACGGT CGTAAGGACT GCTGCTATGC CTCGACGACG CGCTAATGCA TTTCTTCAAT AACTTCGTAG GAGCAGTCAT

301 AAAAGTTAAT CTTTTCAACA GCTGTCATAA AGTTGTCACG GCCGAGACTT ATAGTCGCTT TGTTTTTATT TTTTAATGTA TTTGTAACTA GTACGCAAGT
     TTTTCAATTA GAAAAGTTGT CGACAGTATT TCAACAGTGC CGGCTCTGAA TATCAGCGAA ACAAAAATAA AAAATTACAT CATGCGTTCA

401 TCACGTAAAA AGGGTATCTA GAGGTTGAGG TGATTTTATG AAAAAGAATA TCGCATTTCT TCTTGCATCT ATGTTCGTTT TTTCTATTGC TACAAATGCC
     AGTGCATTTT TCCCATAGAT CTCCAACTCC ACTAAAATAC TTTTTCTTAT AGCGTAAAGA AGAACGTAGA TACAAGCAAA AAAGATAACG ATGTTTACGG

501 TATGCATCTG GTACCGCCAT GGCTGATCCG AACCGTTTCC GCGGTAAAGA TCTGGCAGGT GAGGATCCGG AGGAGGCGCC GAGGGTGACG
     ATACGTAGAC CATGGCGGTA CCGACTAGGC TTGGCAAAGG CGCCATTTCT AGACCGTCCA CTCCTAGGCC TCCTCCGCGG CTCCCACTGC
   1    SerG         lyThrAlaMe tAlaAspPro AsnArgPheA rgGlyLysAs pLeuAlaGly SerProGlyG lyGlyGlyAla GluGlyAspAsp

601 ATCCCGCAAA AGCGGCCTTT AACTCCCTGC AAGCCTCAGC GACCGAATAT ATCGGTTATG CGTGGGCGAT GGTTGTTGTC AATGTCGGCG CAACTATCGG
     TAGGGCGTTT TCGCCGGAAA TTGAGGGACG TTCGGAGTCG CTGGCTTATA TAGCCAATAC GCACCCGCTA CCAACACAG TTAACAGGCC GTTGATAGCC
  33    ProAlaLy sAlaAlaPhe AsnSerLeuG lnAlaSerAl aThrGluTyr IleGlyTyrA laTrpAlaMe tValValVal lleThrIleGly 701 TATCAAGCTG TTTAAGAAAT TCACCTCGAA AGCAAGCTGA TAAACCGATA CAATTAAAGG CTCCTTTTGG AGCCTTTTTT TTTGGAGATT TTCAACGTGA
     ATAGTTCGAC AAATTCTTTA AGTGGAGCTT TCGTTCGACT ATTTGGCTAT GTTAATTTCC GAGGAAAACC TCGGAAAAAA AAACCTCTAA AAGTTGCACT
  66    IleLysLeu PheLysLysP heThrSerLy sAlaSer 801 AAAAATTATT ATTCGCAATT CCTTTAGTTG TTCCTTTCTA TTCTCACTCC GCTGAAACTG TTGAAAGTTG TTTAGCAAAA CCCATACAG AAAATTCATT
     TTTTTAATAA TAAGCGTTAA GGAAATCAAC AAGGAAAGAT AAGAGTGAGG CGACTTTGAC AACTTTCAAC AAATCGTTTT GGGGTATGTC TTTTAAGTAA 901 TACTAACGTC TGGAAAGACG ACAAAACTTT AGATCGTTAC GCTAACTATG AGGGTTGTCT GTGGAATGCT GTCCCAAC ACAGGCGGTTG TAGTTTGTAC TGGTGACGAA
     ATGATTGCAG ACCTTTCTGC TGTTTTGAAA TCTAGCAATG CGATTGATAC TCCCAACAGA CACCCGGTTG CAGGGCCAAC ATCAAACATG ACCACTGCTT 1001 ACTCAGTGTC TAGCTAGAGT GGCGGGTGGCT CTGGTTCCGG TATGAAAAGA TGGCAAACGC TAATAAGGGG GCTATGACCG AAAATGCCGA
     TGAGTCACAG ATCGATCTCA CCGCCCACCGA GACCAAGGCC GACCTTTTCT ACCGTTTGCG ATTATTCCCC CGATACTGGC TTTTACGGCT
```

FIG. 24A

```
1101 TGAAACGCG CTACAGTCTG AGCTAAAGG CAAACTTGAT TCTGTCGCTA CTGATTACGG TGCTGCTATC GATGGTTTCA TTGGTGACGT TTCCGGCCTT
     ACTTTGCGC GATGTCAGAC TCGATTTCC GTTGAACTA AGACAGCGAT GACTAATGCC ACGACGATAG CTACCAAAGT AACCACTGCA AAGGCCGGAA

1201 GCTAATGGTA ATGGTGCTAC TGGTGATTTT GCTGGCTCTA ATTCCCAAAT GGCTCAAGTC GGTGACGGTG ATAATTCACC TTTAATGAAT AATTTCCGTC
     CGATTACCAT TACCACGATG ACCACTAAAA CGACCGAGAT TAAGGGTTTA CCGAGTTCAG CCACTGCCAC TATTAAGTGG AAATTACTTA TTAAAGGCAG

1301 AATATTACC TTCCCTCCCT CAATCGGTTG AATGTCGCCC TTTTGTCTTT AGCGCTGGTA AACCATGATGA ATTTTCTATT GATTGTGACA AAATAAACTT
     TTATAAATGG AAGGGAGGGA GTTAGCCAAC TTACAGCCGG AAAACAGAAA TCGCGACCAT TTGGTATACT TAAAAGATAA CTAACACTGT TTTATTTGAA

1401 ATTCCGTGGT GTCTTTGCGT TTCTTTTATA TGTTGCCACC GTTTGCTAAC TATTTTCTAC ATACTGCGTA ATAAGGAGTC TTAATCATGC
     TAAGGCACCA CAGAAACGCA AAGAAAATAT ACAACGGTGG CAAACGATTG ATAAAAGATG TATGACGCAT TATTCCTCAG AATTAGTACG

3201 ACTCAAAGGC GGTAATACGG TTATCCACAG AATCAGGGGA TAACGCAGGA AAGAACATGT GAGCAAAAGG CCAGCAAAAG GCCAGGAACC GTAAAAAGGC
     TGAGTTTCCG CCATTATGCC AATAGGTGTC TTAGTCCCT ATTGCGTCCT TTCTTGTACA CTCGTTTTCC GGTCGTTTTC CGGTCCTTGG CATTTTTCCG

3301 CGCGTTGCTG GCGTTTTTCC ATAGGCTCCG CCCCCCTGAC GAGCATCACA AAAATCGACG CTCAAGTCAG AGGTGGCGAA ACCCGACAGG ACTATAAAGA
     GCGCAACGAC CGCAAAAAGG TATCCGAGGC GGGGGGACTG CTCGTAGTGT TTTTAGCTGC GAGTTCAGTC TCCACCGCTT TGGGCTGTCC TGATATTTCT

3401 TACCAGGCGT TTCCCCCTGG AAGCTCCCTC GTGCGCTCTC CTGTTCCGAC CCTGCCGCTT ACCGGATACC TGTCCGCCCT TCTCCCTTCG GGAAGCGTGG
     ATGGTCCGCA AGGGGGACC TTCGAGGGAG CACGCGAGAG GACAAGGCTG GGACGGCGAA TGGCCTATGG ACAGGCGGAA AGAGGGAAGC CCTTCGCACC

3501 CGCTTTCTCA TAGCTCACGC TGTAGGTATC TCAGTTCGGT GTAGGTCGTT CGCTCCAAGC TGGGCTGTGT GCACGAACCC CCCGTTCAGC CCGACCGCTG
     GCGAAAGAGT ATCGAGTGCG ACATCCATAG AGTCAAGCCA CATCCAGCAA GCGAGGTTCG ACCCGACACA CGTGCTTGGG GGGCAAGTCG GGCTGGCGAC

3601 CGCCTTATCC GGTAACTATC GTCTTGAGTC CAACCCGGTA TATCGCCACT AGACACGACT TATCGCCAGC GGCAGCAGCC ACTGGTAACA GGATTAGCAG
     GCGGAATAGG CCATTGATAG CAGAACTCAG GTTGGGCCAT TCTGTGCTGA ATAGCCGGTGA CCGTCGTCGG TGACCATTGT CCTAATCGTC TCGCTCCATA

3701 GTAGGCGGTG CTACAGAGTT CTTGAAGTGG TGGCCTAACT ACGGCTACAC TAGAAGGACA GTATTTGGTA TCTGCGCTCT GCTGAAGCCA GTTACCTTCG
     CATCCGCCAC GATGTCTCAA GAACTTCACC ACCGGATTGA TGCCCGATGTG ATCTTCCTGT CATAAACCAT AGACGCGAGA CGACTTCGGT CAATGGAAGC

3801 GAAAAAGAGT TGGTAGCTCT TGATCCGGCA AACAAACCAC CGCTGGTAGC CGGTGGTTTT TTGTTTGCAA GCAGCAGATT ACGCGCAGAA AAAAAGGATC
     CTTTTTCTCA ACCATCGAGA ACTAGGCCGT TTGTTTGGTG GCGACCATCG GCCACCAAAA AACAAACGTT CGTCGTCTAA TGCGCGTCTT TTTTTCCTAG

3901 TCAAGAAGAT CCTTTGATCT TTTCTACGGG GTCTGACGCT CAGTGGAACG AAAACTCACG TTAAGGGATT TTGGTCATGA GATTATCAAA AAGGATCTTC
     AGTTCTTCTA GGAAACTAGA AAAGATGCCC CAGACTGCGA GTCACCTTGC TTTTGAGTGC AATTCCCTAA AACCAGTACT CTAATAGTTT TTCCTAGAAG

4001 ACCTAGATCC TTTTAAATTA AAAATGAAGT TTTAAATCAA TCTAAAGTAT ATATGAGTAA ACTTGGTCTG ACAGTTACCA ATGCTTAATC AGTGAGGCAC
     TGGATCTAGG AAAATTTAAT TTTTACTTCA AAATTTAGTT AGATTTCATA TATACTCATT TGAACCAGAC TGTCAATGGT TACGAATTAG TCACTCCGTG
```

FIG. 24B

```
4101 CTATCTCAGC GATCTGTCTA TTTCGTTCAT CCATAGTTGC CTGACTCCCC GTCGTGTAGA TAACTACGAT ACGGGAGGGC TTACCATCTG GCCCCAGTGC
     GATAGAGTCG CTAGACAGAT AAAGCAAGTA GGTATCAACG GACTGAGGGG CAGCACATCT ATTGATGCTA TGCCCTCCCG AATGGTAGAC CGGGGTCACG

4201 TGCAATGATA CCCGGAGACC CACGCTCACC GGCTCCAGAT TTATCAGCAA TAAACCAGCC AGCCGGAAGG GCCGAGCGCA TTACCATCTG TGCAACTTTA
     ACGTTACTAT GGCGCTCTGG GTGCGAGTGG CCGAGGTCTA AATAGTCGTT ATTGGTCGG TCGGCCTTCC CGGCTCGCGT CTTCACCAGG ACGTTGAAAT

4301 TCCGCCTCCA TCCAGTCTAT TAATTGTTGC CGGGAAGCTA GAGTAAGTAG TTCGCCAGTT AATAGTTTGC GCAACGTTGT TGCCATTGCT GCAGGCATCG
     AGGCGGAGGT AGTTCAGATA ATTAACAACG GCCCTTCGAT CTCATTCATC AAGCGGTCAA TTATCAAACG CGTTGCAACA ACGGTAACGA CGTCCGTAGC

4401 TGGTGTCACG CTCGTCGTTT GGTATGGCTT CATTCAGCTC CGGTTCCCAA CGATCAAGGC GAGTACATG ATCCCCCATG TTGTGCAAAA AAGCGGTTAG
     ACCACAGTGC GAGCAGCAAA CCATACCGAA GTAAGTCGAG GCCAAGGGTT GCTAGTTCCG CTCAATGTAC TAGGGGTAC AACACGTTTT TTCGCCAATC

4501 CTCCTTCGGT CCTCCGATCG TTGTCAGAAG TAAGTTGGCC TCAACCAAGT GCAGTGTATT CACTCATGGT TATGGCAGCA CTGCATAATT CTCTTACTGT CATGCCATCC
     GAGGAAGCCA GGAGGCTAGC AACAGTCTTC ATTCAACCGG AGTTGGTTCA CGTCACAATA ATACCGTCGT GCTAGTTCCG CTCAATGTAC GACGTATTAA GTACGGTAGG

4601 GTAAGATGCT TTTCTGTGAC TGGTGAGTAC TCAACCAAGT TGCTCATCAT CATTCTGAGA ATAGTGTATG CGGCGACCGA GTTGCTCTTG CCCGGCGTCA ACACGGGATA
     CATTCTACGA AAAGACACTG ACCACTCATG AGTTGGTTCA ACGAGTAGTA GTAAGACTCT TATCACATAC GCCGCTGGCT CAACGAGAAC GGGCCGCAGT TGTGCCCTAT

4701 ATACCGCGCC ACATAGCAGA ACTTTAAAAG TGCTCATCAT ACTTGTTGCA CATTCTGAGA TGGAAAACGT TCTTCGGGGC GAAAACTCTC AAGGATCTTA CCGCTGTTGA GATCCAGTTC
     TATGGCGCGG TGTATCGTCT TGAAATTTTC ACGAGTAGTA TGAACAACGT GTAAGACTCT ACCTTTTGCA AGAAGCCCCG CTTTTGAGAG TTCCTAGAAT GGCGACAACT CTAGTCAAG

4801 GATGTAACCC ACTCGTGCAC CCAACTGATC TTCAGCATCT CTCATACTCT TTTACTTCA CCAGCGTTTC TGGGTGAGCA AAAACAGGAA GGCAAAATGC CGCAAAAAAG
     CTACATTGGG TGAGCACGTG GGTTGACTAG AAGTCGTAGA GAGTATGAGA AAATGAAAGT GGTCGCAAAG ACCCACTCGT TTTTGTCCTT CCGTTTTACG GCGTTTTTTC

4901 GGAATAAGGG CGACACGGAA ATGTTGAATA CTCATAGTCT ATATTATTGA AGCATTATC AGGGTTATTG TCTCATGAGC GGATACATAT
     CCTTATTCCC GCTGTGCCTT TACAACTTAT GAGTATCAGA TATAATAACT TCGTAATAAG TCCCAATAAC AGAGTACTCG CCTATGTATA

5001 TTGAATGTAT TTAGAAAAAT AAACAAATAG GGGTTCCGCG CACATTTCCC CGAAAAGTGC CACCTGACGT CTAAGAAACC ATTATTATCA TGACATTAAC
     AACTTACATA AATCTTTTTA TTTGTTTATC CCCAAGGCGC GTGTAAAGG GCTTTTCACG GTGGACTGCA GATTCTTTGG TAATAATAGT ACTGTAATTG

5101 CTATAAAAAT AGGCGTATCA CGAGGCCCTT TCGTCTTCAA
     GATATTTTA TCCGCATAGT GCTCCGGGAA AGCAGAAGTT
```

FIG. 24C

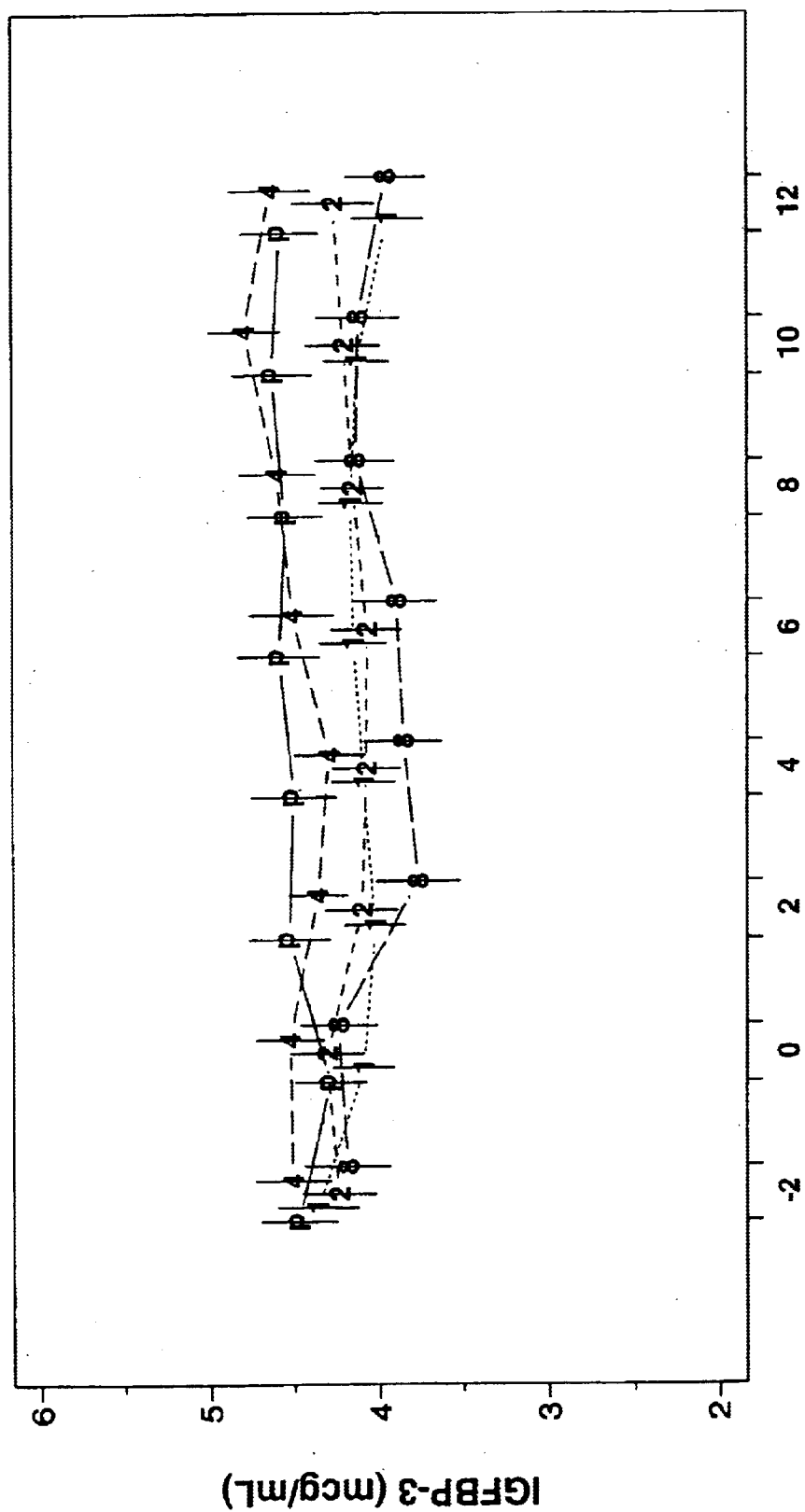

US 6,750,321 B1

INSULIN-LIKE GROWTH FACTOR AGONIST MOLECULES

This is a division of application U.S. Ser. No. 09/337,227 filed Jun. 22, 1999, now U.S. Pat. No. 6,420,518 which is a continuation-in-part of U.S. Ser. No. 09/052,888 filed Mar. 31, 1998, now U.S. Pat. No. 6,251,865, which is a continuation-in-part application of U.S. Ser. No. 08/825,852 filed Apr. 4, 1997, issued as U.S. Pat. No. 6,121,416, which applications are incorporated herein by reference and to which applications priority is claimed under 35 USC §120.

BACKGROUND OF THE INVENTION

1. Field of Invention

This invention relates to molecules useful as agonists of the insulin-like growth factors (IGFs). More particularly, these molecules inhibit the interaction of an IGF with one or more of its IGF binding proteins. Such molecules can be used, for example, in any methods where the IGFs are used, for example, in treating hyperglycemic, obesity-related, neurological, cardiac, renal, immunologic, and anabolic disorders.

2. Description of Background and Related Art

There is a large body of literature on the actions and activities of IGFs (IGF-I, IGF-II, and IGF variants). Human IGF-I is a 7649-dalton polypeptide with a pI of 8.4 (Rinderknecht and Humbel, *Proc. Natl. Acad. Sci. USA*, 73: 2365 (1976); Rinderknecht and Humbel, *J. Biol. Chem.*, 253: 2769 (1978)) belonging to a family of somatomedins with insulin-like and mitogenic biological activities that modulate the action of growth hormone (GH) (Van Wyk et al., *Recent Prog. Horm. Res.*, 30: 259 (1974); Binoux, *Ann. Endocrinol.*, 41: 157 (1980); Clemmons and Van Wyk, *Handbook Exp. Pharmacol.*, 57: 161 (1981); Baxter, *Adv. Clin. Chem.*, 25: 49 (1986); U.S. Pat. No. 4,988,675; WO 91/03253; WO 93/23071).

Like GH, IGF-I is a potent anabolic protein. See Tanner et al., *Acta Endocrinol.* 84: 681–696 (1977); Uthne et al., *J. Clin. Endocrinol. Metab.*, 3: 548–554 (1974). See also Ross et al., *Intensive Care Med.*, 19 Suppl. 2: S54–57 (1993), which is a review of the role of insulin, GH, and IGF-I as anabolic agents in the critically ill. IGF-I has hypoglycemic effects similar to those of insulin, but also promotes positive nitrogen balance (Underwood et al., *Hormone Res.*, 24: 166 (1986); Guler et al., *N. Engl. J. Med.*, 317: 137 (1987)). Due to this range of activities, IGF-I is being tested in humans for such widely disparate uses as wound healing, treatment of diabetes, reversal of whole body catabolic states, treatment of heart conditions such as congestive heart failure, and treatment of neurological disorders (Guler et al., *Proc. Nati. Acad. Sci. USA* 85: 4889–4893 (1988); Duerr et al., *J. Clin. Invest.*, 95: 619–627 (1995); and Barinaga, *Science*, 264: 772–774 (1994)).

U.S. Pat. Nos. 5,273,961; 5,466,670; 5,126,324; 5,187,151; 5,202,119; 5,374,620; 5,106,832; 4,988,675; 5,106,832; 5,068,224; 5,093,317; 5,569,648; and 4,876,242; WO 92/11865; WO 96/01124; WO 91/03253; WO 93/25219; WO 93/08826; and WO 94/16722 disclose various methods of treating mammals, especially human patients, using IGF-I. In addition, clinical uses of IGF-I are described, for example, in Bondy, *Ann Intern. Med.*, 120: 593–601 (1994).

As one specific use, IGF-I has been found to exert a variety of actions in the kidney (Hammerman and Miller, *Am. J. Physiol.*, 265: F1–F14 (1993)). It has been recognized for decades that the increase in kidney size observed in patients with acromegaly is accompanied by a significant enhancement of glomerular filtration rate (O'Shea and Layish, *J. Am. Soc. Nephrol.*, 3: 157–161 (1992)). U.S. Pat. No. 5,273,961 discloses a method for prophylactic treatment of mammals at risk for acute renal failure. In humans IGF-I has been shown to preserve renal function post-operatively (Franklin et al., *Am. J. Physiol.*, 272: F257–F259 (1997)). Infusion of the peptide in humans with normal renal function increases glomerular filtration rate and renal plasma flow (Guler et al., *Acta Endocrinol.*, 121: 101–106 (1989); Guler et al., *Proc. Natl. Acad. Sci. USA*, 86: 2868–2872 (1989); Hirschberg et al., *Kidney Int.*, 43: 387–397 (1993); U.S. Pat. No. 5,106,832). Further, humans with moderately reduced renal function respond to ru short-term (four days) IGF-I administration by increasing their rates of glomerular filtration and renal plasma flow. Hence, IGF-I is a potential therapeutic agent in the setting of chronic renal failure (O'Shea et al., *Am. J. Physiol.*, 264: F917–F922 (1993)). Despite the fact that IGF-I can enhance renal function for those experiencing end-stage chronic renal failure, the enhancements of the glomerular filtration rate and renal plasma flow induced by IGF-I short-term do not persist during long-term administration and incidence of side-effects is high (Miller et al., *Kidney International*, 46: 201–207 (1994)).

For complete reviews of the effect of IGF-I on the kidney, see, e.g., Hammerman and Miller, *Am. J. Physiol.*, 265: F1–F14 (1993) and Hammerman and Miller, *J. Am. Soc. Nephrol.*, 5: 1–11 (1994).

As to anabolic indications for IGF-I, in HIV-infected patients treated consecutively with IGF-I, the IGF-I promoted anabolism, but tachyphylaxis developed rapidly in the patients (Lieberman et al., *U.S. Endocrine Meeting*, June 1993 (Abst. 1664); Lieberman et al., *J. Clin. Endo. Metab.*, 78: 404–410 (1994)). In patients with severe head injuries, a condition associated with profound hypercatabolism and nitrogen loss, infusion of IGF-I produced only a transient positive nitrogen balance. In the first week the patients experienced a positive nitrogen balance, but during the second week, a negative nitrogen balance developed (Chen et al., *U.S. Endocrine Meeting*, June 1993 (Abst. 1596)).

IGF-I has hypoglycemic effects in humans similar to those of insulin when administered by intravenous bolus injection (Underwood et al., *Hormone Research*, 24: 166 (1986)). IGF-I is known to exert glucose-lowering effects in both normal (Guler et al., *N. Engl. J. Med.*, supra) and diabetic individuals (Schoenle et al., *Diabetologia*, 34: 675–679 (1991); Zenobi et al., *J. Clin. Invest.*, 90: 2234–2241 (1992); Sherwin et al., Hormone Research, 41 (Suppl. 2): 97–101 (1994); Takano et al., *Endocrinol. Japan*, 37: 309–317 (1990); Guler et al., *Acta Paediatr. Scand.* (*Suppl.*), 367: 52–54 (1990)), with a time course described as resembling regular insulin. See also Kerr et al., "Effect of Insulin-like Growth Factor 1 on the responses to and recognition of hypoglycemia," American Diabetes Association (ADA), 52nd Annual Meeting, San Antonio, Tex., Jun. 20–23, 1992, which reported an increased hypoglycemia awareness following recombinant human IGF-I (rhIGF-I) administration. In addition, single administration of rhIGF-I reduces overnight GH levels and insulin requirements in adolescents with IDDM (Cheetham et al., *Clin. Endocrinol.*, 40: 515–555 (1994); Cheetham et al., *Diabetolopia*, 36: 678–681 (1993)).

The administration of rhIGF-I to Type II diabetics, as reported by Schalch el al., *J. Clin. Endo. Metab.*, 77: 1563–1568 (1993), demonstrated a fall in both serum insulin as well as a paralleled decrease in C peptide levels. This indicated a reduction in pancreatic insulin secretion after five days of IGF-I treatment. This effect has been independently confirmed by Froesch el al., *Horm. Res.*, 42: 66–71 (1994). In vivo studies in normal rats also illustrate that IGF-I infusion inhibits pancreatic insulin release (Fumsinn et at., *Endocrinology*, 135: 2144–2149 (1994)). In addition, in pancreas perfusion preparations, IGF-I also suppressed insulin secretion (Leahy et al., *Endocrinology*, 126: 1593–1598 (1990)). Despite these clear in vivo inhibitory effects of IGF-I on insulin secretion in humans and animals, in vitro studies have not yielded such uniform results.

RhIGF-I has the ability to improve insulin sensitivity. For example, rhIGF-I (70 µg/kg bid) improved insulin sensitivity in non-diabetic, insulin-resistant patients with myotonic dystrophy (Vlachopapadopoulou et al., *J. Clin. Endo. Metab.*, 80: 3715–3723 (1995)). Saad et al., *Diabetologia*, 37: Abstract 40 (1994) reported dose-dependent improvements in insulin sensitivity in adults with obesity and impaired glucose tolerance following 15 days of rhIGF-I treatment (25 µg and 100 µg/kg bid). RhIGF-I also improved insulin sensitivity and glycemic control in some patients with severe type A insulin resistance (Schoenle el al., *Diabetologia*, 34: 675–679 (1991); Morrow el al., *Diabetes*, 42 (Suppl.): 269 (1993) (abstract); Kuzuya et al., *Diabetes*, 42: 696–705 (1993)) and in other patients with non-insulin dependent diabetes mellitus (Schalch et al., "Short-term metabolic effects of recombinant human insulin-like growth factor I (rhIGF-I) in type II diabetes mellitus", in: Spencer E M, ed., *Modern Concepts of Insulin-like Growth Factors* (New York: Elsevier 1991) pp. 705–713, Zenobi et al., *J. Clin. Invest.*, 90: 2234–2241 (1992)).

A general scheme for the etiology of some clinical phenotypes that give rise to insulin reseistance and the possible effects of administration of IGF-I on selected representative subjects is given in several references. See, e.g., Elahi et as., "Hemodynamic and metabolic responses to human insulin-like growth factor-I (IGF-I) in men," in: *Modern Concepts of Insulin-Like Growth Factors*, (Spencer, E M, ed.), Elsevier, N.Y., pp. 219–224 (1991); Quin et a., *New Engl. J. Med.*, 323: 1425–1426 (1990); Schalch et al., "Short-term metabolic effects of recombinant human insulin-like growth factor 1 (rhIGF-I) in type II diabetes mellitus," in: *Modern Concepts of Insulin-Like Growth Factors*, (Spencer, E M, ed.), Elsevier, N.Y., pp. 705–713 (1991); Schoenle et al., *Diabetologia*, 34: 675–679 (1991); Usala et al., *N. Eng. J. Med.*, 327: 853–857 (1992); Lieberman et al., *J. Clin. Endo. Metab.*, 75: 30–36(1992); Zenobi et al., *J. Clin. Invest.*, 90: 2234–2241 (1992); Zenobi et al., *J. Clin. Invest.*, 89: 1908–1913 (1992); Kerr et al., *J. Clin. Invest.*, 91: 141–147 (1993): When IGF-I was used to treat Type II diabetic patients in the clinic at a dose of 120–160 µg/kg twice daily, the side effects outweighed the benefit of the treatment (Jabri et al., *Diabetes*, 43: 369–374 (1994)). See also Wilton, *Acta Paediatr.*, 383: 137–141 (1992) regarding side effects observed upon treatment of patients with IGF-I.

The IGF binding proteins (IGFBPs) are a family of at least six proteins (Jones and Clemmons, *Endocr. Rev.*, 16: 3–34 (1995); Bach and Rechler, *Diabetes Reviews*, 3: 38–61 (1995)), with other related proteins also possibly binding the IGFs. The IGFBPs bind IGF-I and IGF-II with varying affinities and specificities (Jones and Clemmons, supra; Bach and Rechler, supra). For example, IGFBP-3 binds IGF-I and IGF-II with a similar affinity, whereas IGFBP-2 and IGFBP-6 bind IGF-II with a much higher affinity than athey bind IGF-I (Bach and Rechler, supra; Oh et al., *Endocrinology*, 132, 1337–1344 (1993)).

Unlike most other growth factors, the IGFs are present in high concentrations in the circulation, but only a small fraction of the IGFs is not protein bound. For example, it is generally known that in humans or rodents, less than 1% of the IGFs in blood is in a "free" or unbound form (Juul et al., *Clin. Endocrinol.*, 44: 515–523 (1996); Hizuka et al., *Growth Regulation*, 1: 51–55 (1991); Hasegawa et al., *J. Clin. Endocrinol. Metab.*, 80: 3284–3286 (1995)). The overwhelming majority of the IGFs in blood circulate as part of a non-covalently associated ternary complex composed of IGF-I or IGF-II, IGFBP-3, and a large protein termed the acid-labile subunit (ALS) This complex is composed of equimolar amounts of each of the three components. The ternary complex of an IGF, IGFBP-3, and ALS has a molecular weight of approximately 150,000 daltons, and it has been suggested that the function of this complex in the circulation may be to serve as a reservoir and buffer for IGF-I and IGF-II, preventing rapid changes in free IGF-I or I GF-II.

IGF-I naturally occurs in human body fluids, for example, blood and human cerebral spinal fluid. Although IGF-I is produced in many tissues, most circulating IGF-I is believed to be synthesized in the liver. The IGFBPs are believed to modulate the biological activity of IGF-I (Jones and Clemmons, supra), with IGFBP-1 (Lee et al., *Proc. Soc. Exp. Biol. & Med.*, 204: 4–29 (1993)) being implicated as the primary binding protein involved in glucose metabolism (Baxter, "Physiological roles of IGF binding cl proteins", in: Spencer (Ed.), *Modern Concepts of Insulin-like Growth Factors* (Elsevier, N.Y., 1991), pp. 371–380). IGFBP-1 production by the liver is regulated by nutritional status, with insulin directly suppressing its production (Suikkari et al., *J. Clin. Endocrinol. Metab.*, 66: 266–272 (1988)).

The function of IGFBP-1 in vivo is poorly understood. The administration of purified human IGFBP-1 to rats has been shown to cause an acute, but small, increase in blood glucose (Lewitt et al., *Endocrinology*, 129: 2254–2256 (1991)). The regulation of IGFBP-1 is somewhat better understood. It has been proposed (Lewitt and Baxter, *Mol. Cell Endocrinology*, 79: 147–152 (1991)) that when blood glucose rises and insulin is secreted, IGFBP-1 is suppressed, allowing a slow increase in "free" IGF-I levels that might assist insulin action on glucose transport. Such a scenario places the function of IGFBP-1 as a direct regulator of blood glucose.

The IGF system is also composed of membrane-bound receptors for IGF-I, IGF-II, and insulin. The Type 1 IGF receptor is closely related to the insulin receptor in structure and shares some of its signaling pathways (Jones and Clemmons, supra). The IGF-II receptor is a clearance receptor that appears not to transmit an intracellular signal (Jones and Clemmons, supra). Since IGF-I and IGF-II bind to the Type 1 IGF-I receptor with a much higher affinity than to the insulin receptor, it is most likely that most of the effects of IGF-I and IGF-II are mediated by the Type 1 IGF receptor (Ballard et al., "Does IGF-I ever act through the insulin receptor?", in Baxter et al. (Eds.), *The Insulin-Like Growth Factors and Their Regulatory Proteins*, (Amsterdam: Elsevier, 1994), pp. 131–138).

There has been much work identifying the domains on IGF-I and IGF-II that bind to the IGFBPs (Bayne et al., *J. Biol. Chem.*, 265: 15648–15652 (1990); Dubaquie and Lowman, *Biochemistry*, 38: 6386–6396 (1999); U.S. Pat. Nos. 5,077,276; 5,164,370; 5,470,828). For example, it has been discovered that the N-terminal region of IGF-I and IGF-II is critical for binding to the IGFBPs (U.S. Pat. Nos. 5,077,276; 5,164,370; 5,470,828). Thus, the natural IGF-I variant, designated des(1–3)IGF-I, binds poorly to IGFBPs.

A similar amount of research has been devoted to identifying the domains on IGF-I and IGF-II that bind to the Type 1 IGF receptor (Bayne et al., supra; Oh et al., supra). It was found that the tyrosine residues in IGF-I at positions 24, 31, and 60 are crucial to the binding of IGF-I to the Type 1 IGF receptor (Bayne et al., supra). Mutant IGF-I molecules where one or more of these tyrosine residues are substituted showed progressively reduced binding to Type 1 IGF receptors. Bayne et al., supra, also investigated whether such mutants of IGF-I could bind to the Type 1 IGF receptor and to the IGFBPs. They found that quite different residues on IGF-I and IGF-II are used to bind to the IGFBPs from those used to bind to the Type 1 IGF receptor. It is therefore possible to produce IGF variants that show reduced binding to the IGFBPs, but, because they bind well to the Type 1 IGF receptor, show maintained activity in in vitro activity assays.

Also reported was an IGF variant that binds to IGFBPs but not to IGF receptors and therefore shows reduced activity in in vitro activity assays (Bar et al., *Endocrinology*, 127: 3243–3245 (1990)). In this variant, designated (1–27, gly$^4$,38–70)-hIGF-I, residues 28–37 of the C region of human IGF-I are replaced by a four-residue glycine bridge. Bar et al. studied the transport of the mutant IGF-I when it was perfused as a complex with IGFBP through the heart in terms of the localization of IGFBPs bound to the mutant IGF or to IGF itself. There were no data supplied by Bar et al. on the localization of the IGF mutant given alone, only data on the localization of the complex of the IGF mutant and IGFBP. Further, Bar et al. provided no data on any biological or efficacy response to the administration of the IGF mutant.

Other truncated IGF-I variants are disclosed. For example, in the patent literature, WO 96/33216 describes a truncated variant having residues 1–69 of authentic IGF-I. EP 742,228 discloses two-chain IGF-I superagonists which are derivatives of the naturally occurring single-chain IGF-I having an abbreviated C domain. The IGF-I analogs are of the formula: BC$^n$,A wherein B is the B domain of IGF-I or a functional analog thereof, C is the C domain of IGF-I or a functional analog thereof, n is the number of amino acids in the C domain and is from about 6 to about 12, and A is the A domain of IGF-I or a functional analog thereof.

Additionally, Cascieri et al., *Biochemistry*, 27: 3229–3233 (1988) discloses four mutants of IGF-I, three of which have reduced affinity to the Type 1 IGF receptor. These mutants are: (Phe$^{23}$,Phe$^{24}$,Tyr$^{25}$)IGF-I (which is equipotent to human IGF-I in its affinity to the Types 1 and 2 IGF and insulin receptors), (Leu$^{24}$) IGF-I and (Ser$^{24}$) IGF-I (which have a lower affinity than IGF-I to the human placental Type 1 IGF receptor, the placental insulin receptor, and the Type 1 IGF receptor of rat and mouse cells), and desoctapeptide (Leu$^{24}$)IGF-I (in which the loss of aromaticity at position 24 is combined with the deletion of the carboxyl-terminal D region of hIGF-I, which has lower affinity than (Leu$^{24}$)IGF-I for the Type 1 receptor and higher affinity for the insulin receptor). These four mutants have normal affinities for human serum binding proteins.

Bayne et al., *J. Biol. Chem.*, 263: 6233–6239 (1988) discloses four structural analogs of human IGF-I: a B-chain mutant in which the first 16 amino acids of IGF-I were replaced with the first 17 amino acids of the B-chain of insulin, (Gln$^3$,Ala$^4$) IGF-I, (Tyr$^{15}$,Leu$^{16}$)IGF-I, and (Gln$^3$Ala$^4$,Tyr$^{15}$,Leu$^{16}$) IGF-I. These studies identify some of the domains of IGF-I that are responsible for maintaining high-affinity binding with the serum binding protein and the Type 2 IGF receptor.

Bayne et al., *J. Biol. Chem.*, 264: 11004–11008 (1988) discloses three structural analogs of IGF-I: (1–62)IGF-I, which lacks the carboxyl-terminal 8-amino-acid D region of IGF-I; (1–27,Gly$^4$,38–70)IGF-I, in which residues 28–37 of the C region of IGF-I are replaced by a four-residue glycine bridge; and (1–27,Gly$^4$,38–62)IGF-I, with a C region glycine replacement and a D region deletion. Peterkofsky et al., *Endocrinology*, 128: 1769–1779 (1991) discloses data using the Gly$^4$ mutant of Bayne et al., supra (Vol. 264). U.S. Pat No. 5,714,460 refers to using IGF-I or a compound that increases the active concentration of IGF-I to treat neural damage.

Cascieri et al., *J. Biol. Chem.*, 264: 2199–2202 (1989) discloses three IGF-I analogs in which specific residues in the A region of IGF-I are replaced with the corresponding residues in the A chain of insulin. The analogs are: (Ile$^{41}$, Glu$^{45}$,Gln$^{46}$,Thr$^{49}$,Ser$^{50}$,Ile$^{50}$,Ser$^{53}$,Tyr$^{55}$,Gln$^{56}$)IGF-I, an A chain mutant in which residue 41 is changed from threonine to isoleucine and residues 42–56 of the A region are replaced; (Thr$^{49}$,Ser$^{50}$,Ile$^{51}$)IGF-I; and (Tyr$^{55}$,Gln$^{56}$)IGF-I.

Clemmons et al., *J. Biol. Chem.*, 265: 12210–12216 (1990) discloses use of IGF-I analogs that have reduced binding affinity for either the Type 1 IGF receptor or binding proteins to study the ligand specificity of IGFBP-1 and the role of IGFBP-1 in modulating the biological activity of IGF-I.

WO 94/04569 discloses a specific binding molecule, other than a natural IGFBP, that is capable of binding to IGF-I and can enhance the biological activity of IGF-I.

U.S. Pat. Nos. 5,593,844 and 5,210,017 disclose a ligand-mediated immunofunctional binding protein assay method that can be used to quantitate the amount of GH binding protein or IGFBP in a liquid sample by the use of antibodies, where complex formation takes place between one of these binding proteins and the hormone ligand that binds to it.

The direction of research into IGF variants has mostly been is to make IGF variants that do not bind to the IGFBPs but show maintained binding to the IGF receptor. The idea behind the study of such molecules is that the major actions of the IGFBPs are proposed to be an inhibition of the activity of the IGFs. Chief among these variants is the natural molecule, des(1–3)IGF-I, which shows selectively reduced affinity for some of the IGF binding proteins, yet a maintained affinity for the IGF receptor (U.S. Pat. Nos. 5,077, 276; 5,164,370; 5,470,828, supra).

Peptides which bind to IGFBP-1, block IGF-I binding to this binding protein, and thereby release "free-IGF" activity from mixtures of IGF-I and IGFBP-1 have been recently described (Lowman et al., *Biochemistry*, 37: 8870–8878 (1998); WO 98/45427 published Oct. 15, 1998; Lowman et al., International Pediatric Nephrology Association, Fifth Symposium on Growth and Development in Children with Chronic Renal Failure (New York, Mar. 13, 1999)). These include bp1-02, a cyclic (disulfide-containing) peptide discovered from phage-displayed peptide libraries, as well as truncated forms of this peptide: bp1-01 and bp1-16 (WO 98/45427, supra). Peptide inhibition assays showed that bp1-01 and bp1-02 inhibited IGFBP-1 binding to IGF-I with IC$_{50}$ values of 180 nM and 50 nM, respectively; and cell-based assays showed release of "free-IGF" activity with EC$_{50}$ values of 400 nM and 190 nM, respectively (Lowman et al., supra, 1998).

There is a need in the art for a molecule that acts as an IGF agonist, and also for a molecule that binds to IGF binding proteins with high affinity and specificity for therapeutic or diagnostic purposes.

SUMMARY OF THE INVENTION

Additional structure-function studies and affinity maturation beyond that disclosed in Lowman et al., supra, 1998 and WO 98/45427, supra, have been performed using further natural and non-natural amino acid substitutions as well as multiple (combined) substitutions in peptide variants of the bp1-01 family. Unless otherwise specified, all peptides described here are cyclic, containing disulfides between bp1-01 residues Cys-1 and Cys-10.

Accordingly, the present invention relates, in a first embodiment, to a peptide comprising the following sequence:

$Xaa_{(1-4)}CysXaa_{(6)}Xaa_{(7)}GlyXaa_{(9)}Xaa_{(10)}Xaa_{(11)}Xaa_{(12)}Xaa_{(13)}CysXaa_{(15)}Xaa_{(16)}Xaa_{(17)}$ $Xaa_{(18)}$ (SEQ ID NO:1), wherein $Xaa_{(1-4)}$ is absent or is between 1 and 4 amino acids of any kind, $Xaa_{(6)}$, $Xaa_{(7)}$, $Xaa_{(9)}$, $Xaa_{(11)}$, $Xaa_{(15)}$, and $Xaa_{(16)}$ are independently any amino acid, $Xaa_{(10)}$ and $Xaa_{(11)}$ are independently Leu or Nle, and $Xaa_{(12)}$, $Xaa_{(17)}$, and $Xaa_{(18)}$ are independently Nal(1), His, Phe, Trp, Tyr, Pro, Gln, or Met.

In one preferred embodiment, this peptide comprises the following sequence:

GluAlaArgValCysArgAlaGlyPro-LeuGlnTrpLeuCysGluLysTyrPhe (SEQ ID NO:2).

In another preferred embodiment, this peptide comprises the following sequence:

$CysXaa_{(6)}Xaa_{(7)}GlyXaa_{(9)}Xaa_{(10)}Xaa_{(11)}TrpXaa_{(13)}$ $CysXaa_{(15)}Xaa_{(16)}Xaa_{(17)}Xaa_{(18)}$ (SEQ ID NO:3).

More preferably, such peptide comprises one of the following sequences:

CysArgAlaGlyAlaLeuGlnTrpLeuCysGluLysTyrPhe (SEQ ID NO:4);

CysArgAlaGlyArgLeuGlnTrpLeuCysGluLysTyrPhe (SEQ ID NO:5);

CysArgAlaGlyAsnLeuGlnTrpLeuCysGluLysTyrPhe (SEQ ID NO:6);

CysArgAlaGlyProNleGlnTrpLeuCysGluLysTyrPhe (SEQ ID NO:7);

CysArgAlaGlyProLeuGlnTrpNleCysGluLysTyrPhe (SEQ ID NO:8);

CysArgAlaGlyProLeuGlnArgLeuCysGluLysTyrPhe (SEQ ID NO:9);

CysArgAlaGlyProLeuGlnNal(1)LeuCysGluLysTyrPhe (SEQ ID NO:10); or

CysArgAlaGlyProLeuGlnHisLeuCysGluLysTyrPhe (SEQ ID NO:11).

In another preferred embodiment of SEQ ID NO:1, C-terminal to the C-terminal $Xaa_{(18)}$(IL) is the sequence $Xaa_{(19)}ThrTyr$, wherein $Xaal_{(19)}$ is any amino acid. More preferred such peptides comprise the following sequence: $Xaa_{(1-4)}CysArgAlaGlyProLeuGlnTrpLeuCysGluXaa_{(16)}$ $TyrPheXaa_{(19)}ThrTyr$ (SEQ ID NO:12), wherein $Xaa_{(16)}$ is Lys or His and $Xaa_{(19)}$ is Ala, Ser, Gln, Asp, Glu, or Lys. More preferably, such peptides comprise one of the following sequences:

SerGluValGlyCysArgAlaGlyProLeuGlnTrpLeuCysGlu LysTyrPheSerThrTyr (SEQ ID NO:13);

SerGluValGlyCysArgAlaGlyProLeuGlnTrpLeuCysGlu LysTyrPheAlaThrTyr (SEQ ID NO:14);

SerGluValGlyCysArgAlaGlyProLeuGlnTrpLeuCysGlu LysTyrPheGlnThrTyr (SEQ ID NO:15);

SerGluValGlyCysArgAlaGlyProLeuGlnTrpLeuCysGlu LysTyrPheGlnThrThr (SEQ ID NO:16);

SerGluValGlyCysArgAlaGlyProLeuGlnTrpLeuCysGlu LysTyrPheAspThrTyr (SEQ ID NO:17);

SerGluValGlyCysArgAlaGlyProLeuGlnTrpLeuCysGlu LysTyrPheGluThrTyr (SEQ ID NO:18);

SerGluValGlyCysArgAlaGlyProLeuGlnTrpLeuCysGlu LysTyrPheLysThrTyr (SEQ ID NO:19);

GluAlaArgValCysArgAlaGlyProLeuGlnTrpLeuCysGlu LysTyrPheSerThrTyr (SEQ ID NO:20);

GlyGlnGlnSerCysArgAlaGlyProLeuGlnTrpLeuCysGlu LysTyrPheSerThrTyr (SEQ ID NO:21);

AlaSerSerMetCysArgAlaGlyProLeuGlnTrpLeuCysGlu LysTyrPheSerThrTyr (SEQ ID NO:22);

GlnGlyProAspCysArgAlaGlyProLeuGlnTrpLeuCysGlu LysTyrPheSerThrTyr (SEQ ID NO:23);

GlnAlaSerGluCysArgAlaGlyProLeuGlnTrpLeuCysGlu LysTyrPheSerThrTyr (SEQ ID NO:24);

AlaGluThrLeuCysArgAlaGlyProLeuGlnTrpLeuCysGlu LysTyrPheSerThrTyr (SEQ ID NO:25);

AsnSerLeuLeuCysArgAlaGlyProLeuGlnTrpLeuCysGlu LysTyrPheSerThrTyr (SEQ ID NO:26);

AlaGlnTrpValCysArgAlaGlyProLeuGlnTrpLeuCysGlu LysTyrPheSerThrTyr (SEQ ID NO:27);

GlyGlnGlnSerCysAlaAlaGlyProLeuGlnTrpLeuCysGlu HisTyrPheSerThrTyr (SEQ ID NO:28); or

GlyGlnGlnSerCysAlaAlaGlyProLeuGlnTrpLeuCysGlu HisTyrPheSerThrTyrGlyArg (SEQ ID NO:29).

In another specific embodiment, the invention relates to a peptide comprising SEQ ID NO:4; SEQ ID NO:5; SEQ ID NO:6; SEQ ID NO:7;

SEQ ID NO:8; SEQ ID NO:9; SEQ ID NO:10; SEQ ID NO:11; SEQ ID NO: 14;

SEQ ID NO:15; SEQ ID NO:16; SEQ ID NO:17; SEQ ID NO:18; SEQ ID NO:19;

SEQ ID NO:20; SEQ ID NO:21; SEQ ID NO:22; SEQ ID NO:23; SEQ ID NO:24; SEQ ID NO:25; SEQ ID NO:26; SEQ ID NO:27; SEQ ID NO:28; or SEQ ID NO:29.

In another aspect of the invention, the above peptide having SEQ ID NO:1 or SEQ ID NO:3 has a C-terminal fusion comprising the following sequence:

GlyGlyGlySerGlyGlyAlaGlnHisAspGluAlaVal AspAsnLysPheAsnLysGluGlnGlnAsnAlaPheTyrGlu IleLeuHisLeuProAsnLeuAsnGluGluGlnArgAsn AlaPheIleGlnSerLeuLysAspAspProSerGlnSerAlaAsn LeuLeuAlaGluAlaLysLysLeuAsnAspAlaGlnAlaPro AsnValAspMetAsn (SEQ ID NO:30).

In another embodiment, this invention relates to a constrained helical peptide comprising a sequence of nine amino acid residues having a first terminal residue and a second terminal residue, wherein said residues flank an internal sequence of seven amino acids and have side-chains covalently bonded to each other to form a locking moiety and thereby constrain the peptide. Preferably, the internal sequence is $Xaa_{(7)}LeuAlaXaa_{(10)}Xaa_{(11)}Xaa_{(12)}Xaa_{(13)}$ (SEQ ID NO:31), wherein $Xaa_{(7)}$, $Xaa_{(11)}$, $Xaa_{(12)}$, and $Xaa_{(13)}$ are independently Nal(1), His, Phe, Trp, Tyr, Pro, Gln, or Met, and $Xaa_{(10)}$ is any amino acid.

In yet another embodiment, the invention relates to a peptide comprising the following sequence:

$Xaa_{(1-4)}Xaa_{(5)}$, $Xaa_{(6-7)}ProLeuGluXaa_{(11)}LeuAlaXaa_{(14)}$ $Xaa_{(15)}Xaa_{(16)}Xaa_{(17)}GluXaa_{(19)}$ (SEQ ID NO:32), wherein $Xaa_{(1-4)}$ is absent or is between 1 and 4 amino acids of any kind; $Xaa_{(5)}$ is any amino acid, $Xaa_{(6-7)}$ is absent or is between 1 and 2 amino acids, $Xaa_{(14)}$ and $Xaa_{(15)}$ are independently any amino acid, $Xaa_{(11)}$ and $Xaa_{(16)}$ are independently Nal(1), His, Phe, Trp, Tyr, Pro, Gln, or Met, $Xaa_{(17)}$ is absent or is Nal(1), His, Phe, Trp, Tyr, Pro, Gln, or Met, and $Xaa_{(19)}$ is absent or is Gly.

In a preferred peptide of this type, C-terminal to the C-terminal $Xaa_{(19)}$ is the sequence $Xaa_{(20)}ThrTyr$, wherein $Xaa_{(20)}$ is any amino acid.

More specifically, the peptide comprises the following sequence:

$Xaa_{(5)}Xaa_{(6-7)}ProLeuGluXaa_{(11)}LeuAlaXaa_{(14)}Xaa_{(15)}$
$Xaa_{(16)}Xaa_{(17)}GluGly$ (SEQ ID NO:33), wherein $Xaa_{(6-7)}$ is two amino acids. Other preferred peptides of this type comprise one of the following sequences:

ArgAlaGlyProLeuGluTrpLeuAlaGluLysTyrGluGly (SEQ ID NO:34);

ArgProLeuGluTrpLeuAlaGluLysTyrPheGlu (SEQ ID NO:35); or

ArgAlaGlyProLeuGluTrpLeuAlaGluLysTyrPheGlu (SEQ ID NO:36).

Any of the above peptides preferably contains 10–60 amino acids, more preferably 12–25 amino acids.

Also provided herein is a composition comprising one of the peptides described above in a carrier. Preferably, this composition is sterile and the carrier is a pharmaceutically acceptable carrier.

Uses of these peptides include all uses that liberate or enhance at least one biological activity of exogenous or endogenous IGFs. They can be used in treating, inhibiting, or preventing conditions in which an IGF such as IGF-I is useful, as described below.

The invention also provides a method of constructing a constrained helical peptide, comprising the steps of:

(a) synthesizing a peptide comprising a sequence of nine amino acid residues having a first terminal residue and a second terminal residue that flank an internal sequence of seven amino acid residues and have side-chains containing an amide bond-forming substituent;

(b) providing a difunctional linker having a first functional group capable of forming an amide linkage with the side-chain amide bond-forming substituent of the first terminal residue and having a second functional group capable of forming an amide linkage with the side-chain amide bond-forming substituent of the second terminal residue; and (c) cyclizing the peptide by reacting the side-chain amide bond-forming substituent of the first terminal residue with the first functional group of the difunctional linker to form an amide linkage and reacting the side-chain amide bond-forming substituent of the second terminal residue with the second functional group of the difunctional linker to form an amide linkage, yielding a constrained helical peptide.

In a preferred embodiment, in step (a) the side-chain amide bond-forming substituent of the first terminal residue is protected with a first protecting group and the side-chain amide bond-forming substituent of the second terminal residue is protected with a second protecting group, wherein the first protecting group and the second protecting group are differentially removable, and wherein in step (c) the first protecting group is removed such that the side-chain amide bond-forming substituent of the first terminal residue is deprotected and the side-chain amide bond-forming substituent of the second terminal residue is not deprotected before the peptide is reacted with the difunctional linker, and thereafter the peptide is reacted with the difunctional linker to form an amide linkage between the side-chain amide bond-forming substituent of the first terminal residue and the first functional group of the difunctional linker, and thereafter the second protecting group is removed from the side-chain amide bond-forming substituent of the second terminal residue and the peptide is cyclized by intramolecularly reacting the side-chain amide bond-forming substituent of the second terminal residue with the second functional group of the difunctional linker to form an amide linkage.

In another aspect, the invention provides a method of constructing a constrained helical peptide, comprising the steps of:

(a) synthesizing a peptide comprising a sequence of nine amino acid residues having a first terminal residue and a second terminal residue that flank an internal sequence of seven amino acid residues and have a side-chain containing an amide bond-forming substituent, wherein the first terminal residue is coupled to a difunctional linker having a first functional group and a second functional group, wherein the first functional group is in an amide linkage with the side-chain amide bond-forming substituent of the first terminal residue, and wherein the second functional group of the difunctional linker is capable of forming an amide linkage with the side-chain amide bond-forming substituent of the second terminal residue; and (b) cyclizing the peptide by intramolecularly reacting the side-chain amide bond-forming substituent of the second terminal residue with the second functional group of the difunctional linker to form an amide linkage and thereby yield a constrained helical peptide.

In another embodiment, the invention provides a constrained helical peptide made according to one of the above methods.

Additionally provided herein is a method for increasing serum and tissue levels of biologically-active IGF in a mammal comprising administering to the mammal an effective amount of any of the above peptides. The mammal is preferably human. Also preferred is where administering the peptide, preferably in an amount effective to produce body weight gain, causes an increase in anabolism in the mammal. Additionally preferred is that glycemic control is effected in the mammal after the peptide is administered.

Any of the peptides herein can be administered alone or rn together with another agent such as GH, a GH releasing peptide (GHRP), a GH releasing factor (GHRF), a GH releasing hormone (GHRH), a GH secretagogue, an IGF, an IGF in combination with an IGFBP, an IGFBP, GH in combination with a GH binding protein (GHBP), insulin, or a hypoglycemic agent (which includes in the definition below an insulin-sensitizing agent such as thiazolidinedione).

In another embodiment, a method is provided for determining appropriate dosing of one of the above peptides comprising:

(a) measuring the level of an IGF in a body fluid;

(b) contacting the fluid with a peptide herein using single or multiple doses; and (c) re-measuring the level of an IGF in the fluid, wherein if the fluid IGF level has fallen by an amount sufficient to produce the desired efficacy for which the peptide is to be administered, then the dose of the peptide is adjustable or adjusted to produce maximal efficacy.

In yet another embodiment, a method is provided for determining the amount of a particular IGFBP or the amount of one of the above peptides bound to a particular IGFBP in a biological fluid so that dosing of the peptide can be adjusted appropriately. This method involves:

(a) contacting the fluid with 1) one of the above-identified peptides and 2) a first antibody attached to a solid-phase carrier, wherein the first antibody is specific for epitopes on the IGFBP such that in the presence of antibody the IGF binding sites remain available on the IGFBP for binding to the peptide, thereby forming a complex between the first antibody and the IGFBP, for a period of time sufficient to saturate all available IGF binding sites on the IGFBP, thereby forming a saturated complex;

(b) contacting the saturated complex with a detectably labeled second antibody which is specific for epitopes on the peptide which are available for binding when the peptide is bound to the IGFBP; and (c) quantitatively analyzing the amount of the labeled second antibody bound as a measure of the IGFBP in the biological fluid, and therefore as a measure of the amount of the peptide bound.

Also contemplated herein is a kit comprising a container containing a pharmaceutical composition containing one of the above peptides and instructions directing the user to utilize the composition. This kit may optionally further comprise a container containing a GH, a GHRP, a GHRF, a GHRH, a GH secretagogue, an IGF, an IGF complexed to an IGFBP, an IGFBP, a GH complexed with a GHBP, insulin, or a hypoglycemic agent.

In another embodiment herein, a method for directing endogenous IGF either away from, or towards, a particular site in a mammal comprising administering to the mammal an effective amount of one of the above peptides herein that is specific for an IGFBP that is either prevalent at, or absent from, the site.

A further embodiment is a method for detecting endogenous or exogenous IGF bound to an IGF binding protein or the amount of any peptide herein or detecting the level of unbound IGF in a biological fluid comprising:

(a) contacting the fluid with 1) a means for detecting the peptide attached to a solid-phase carrier, wherein the means is specific for the peptide such that in the presence of the peptide the IGF binding sites remain available on the peptide for binding to the IGF binding protein, thereby forming a complex between the means and the IGF binding protein; and 2) the peptide for a period of time sufficient to saturate all available IGF binding sites on the IGF binding protein, thereby forming a saturated complex;

(b) contacting the saturated complex with a detectably labeled second means which is specific for the IGF binding protein which are available for binding when the peptide is bound to the IGF binding protein; and (c) quantitatively analyzing the amount of the labeled means bound as a measure of the IGFBP in the biological fluid, and therefore as a measure of the amount of bound peptide and IGF binding protein, bound IGF and IGF binding protein, or active IGF present in the fluid.

The present invention further provides various dosage forms of any of the peptides of the present invention, including but not limited to, those suitable for parenteral, oral, rectal and pulmonary administration of a peptide. In preferred aspects herein a therapeutic dosage form is provided suitable for inhalation and the invention provides for the therapeutic treatment of diseases or disorders involving an IGF-mediated or associated process or event via pulmonary administration of a peptide of the invention. More particularly, the invention is directed to pulmonary administration of the peptides herein by inhalation. Thus, the present invention provides an aerosol formulation comprising an amount of a peptide of the invention, effective to block or prevent an IGF-mediated or associated process or event and a dispersant. In one embodiment, any one of the above peptides can be provided in a liquid aerosol formulation. Alternatively, the peptide can be provided as a dry powder aerosol formulation. Therefore, according to the present invention, formulations are provided that provide an effective non-invasive alternative to other parenteral routes of administration of the peptides herein for the treatment of IGF-mediated or associated events.

Isolated nucleic acid encoding one of the above peptides herein is also provided, and may be used for in vivo or ex vivo gene therapy.

The peptides herein are superior to IGF mutants such as des(1–3)IGF-I, since the latter have short half-lives and effects, whereas the peptides herein have longer half lives and effects, and this binding avoids normal renal filtration which would otherwise eliminate short peptides and other small molecules rapidly. Further, administering any one of the peptides herein together with exogenous GH or GH secretagogues would have the advantage of minimizing diabetogenic effects of such GH and secretagogues. Yet another advantage of the peptides herein is that there is a ceiling of the effects of the IGF agonist peptide herein. That is, it cannot exert more effects than the maximum capacity of IGFBPs to carry IGFS, unlike IGF-I, which can have unwanted side effects if used in large concentrations over its maximum efficacy.

BRIEF DESCRIPTION OF THE DRAWINGS

FIG. 1 shows a BIAcore™ inhibition assay of IGF-I activity using seven different peptides (bp1-16: filled circles, (i+7)A: open circles, (i+7)B: open diamonds, (i+7)C: open triangles, (i+7)D: open squares, (i+8)B: filled squares, (i+8) C: filled triangles).

FIG. 3 shows an analytical HPLC run of the trypsin-cleaved bp1-625-Z fusion. The major peaks were identified by mass spectrometry as (A) Z-domain fragment and (B) bp1-625 peptide.

DESCRIPTION OF THE PREFERRED EMBODIMENTS

A. Definitions

Figure 2:
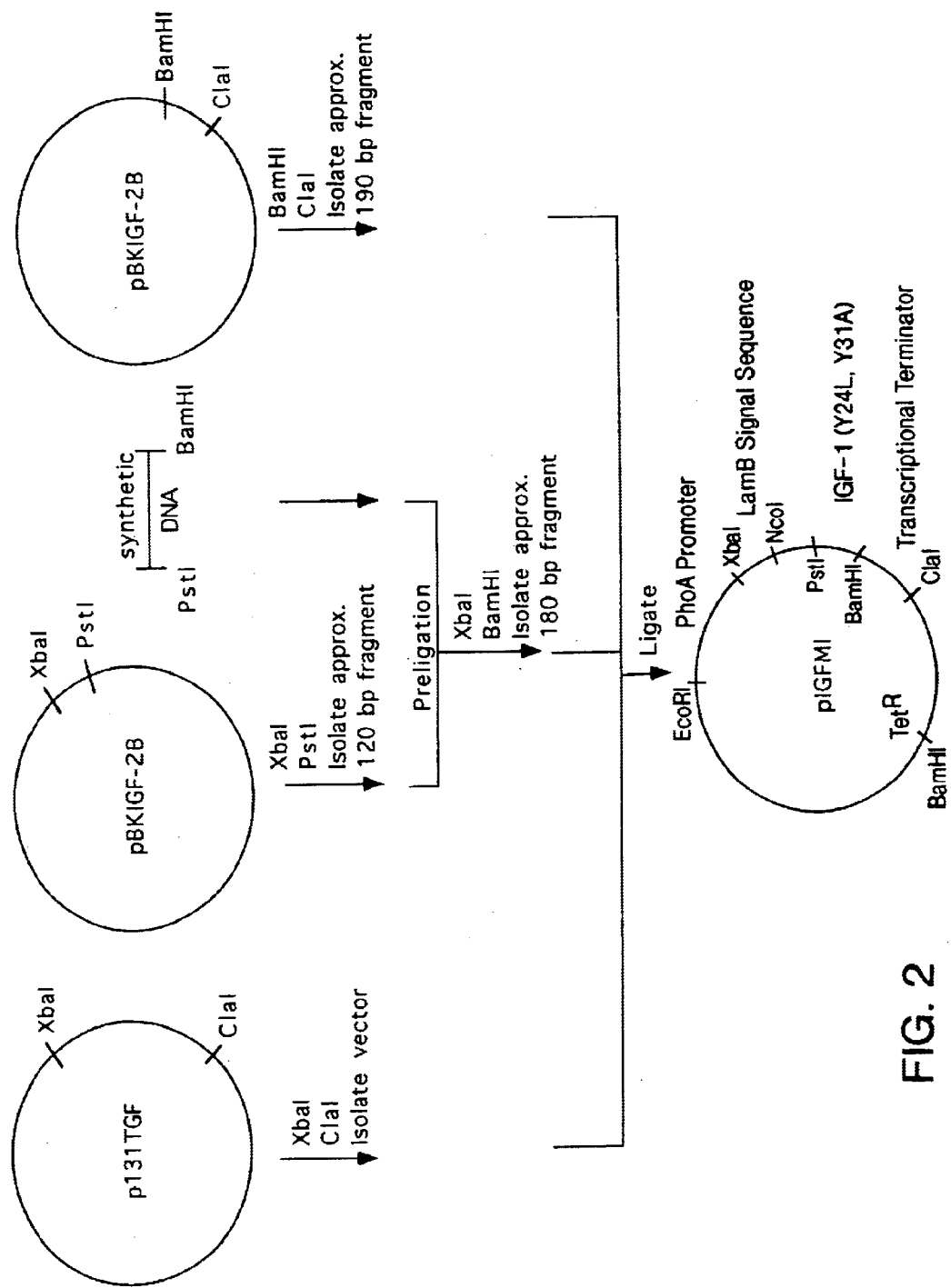
FIG. 2 shows a KIRA assay of peptide activity using four different peptides (bp1-16: circles, bp1-02: squares, bp1-25: triangles, and bp1-40: diamonds).

As used herein, "mammal" for purposes of treatment refers to any animal classified as a mammal, including humans, domestic, and farm animals, and zoo, sports, or pet animals, such as dogs, horses, cats, sheep, pigs, cows, etc. The preferred mammal herein is a human. The term "non-adult" refers to mammals that are from perinatal age (such as low-birth-weight infants) up to the age of puberty, the latter being those that have not yet reached full growth potential.

As used herein, "IGF" refers to native insulin-like growth factor-I and native insulin-like growth factor-II as well as natural variants thereof such as brain IGF, otherwise known as des(1–3)IGF-I.

As used herein, "IGF-I" refers to insulin-like growth factor-I from any species, including bovine, ovine, porcine, equine, and human, preferably human, and, if referring to exogenous administration, from any source, whether natural, synthetic, or recombinant. Human native-sequence, mature IGF-I, more preferably without a N-terminal methionine is prepared, e.g., by the process described in EP 230,869 published Aug. 5, 1987; EP 128,733 published Dec. 19, 1984; or EP 288,451 published Oct. 26, 1988. More preferably, this native-sequence IGF-I is recombinantly produced and is available from Genentech, Inc., South San Francisco, Calif. for clinical investigations.

As used herein, "IGF-II" refers to insulin-like growth factor-II from any species, including bovine, ovine, porcine, equine, and human, preferably human, and, if referring to exogenous administration, from any source, whether natural, synthetic, or recombinant. It may be prepared by the method described in, e.g., EP 128,733, supra.

An "IGFBP" or an "IGF binding protein" refers to a protein or polypeptide normally associated with or bound or complexed to IGF-I or IGF-II, whether or not it is circulatory (i.e., in serum or tissue). Such binding proteins do not include receptors. This definition includes IGFBP-1, IGFBP-2, IGFBP-3, IGFBP-4, IGFBP-5, IGFBP-6, Mac 25 (IGFBP-7), or prostacyclin-stimulating factor (PSF) or endothelial cell-specific molecule (ESM-1), as well as other proteins with high homology to IGFBPs. Mac 25 is described, for example, in Swisshelm et al., *Proc. Natl. Acad. Sci. USA*, 92: 4472–4476 (1995) and Oh et al., *J. Biol. Chem.*, 271: 30322–30325 (1996). PSF is described in Yamauchi et al., *Biochemical Journal*, 303: 591–598 (1994). ESM-1 is described in Lassalle et al., *J. Biol. Chem.*, 271: 20458–20464 (1996). For other identified IGFBPs, see, e.g., EP 375,438 published 27 Jun. 1990; EP 369,943 published 23 May 1990; WO 89/09268 published 5 Oct. 1989; Wood et al., *Molecular Endocrinology*, 2: 1176–1185 (1988); Brinkman et al., The *EMBO J.*, 7: 2417–2423 (1988); Lee et al., *Mol. Endocrinol.*, 2: 404–411 (1988); Brewer et al., *BBRC*, 152: 1289–1297 (1988); EP 294,021 published 7 Dec. 1988; Baxter et al., *BBRC*, 147: 408–415 (1987); Leung et al., *Nature*, 330: 537–543 (1987); Martin et al., *J. Biol. Chem.*, 261: 8754–8760 (1986); Baxter et al., *Comp. Biochem. Physiol.*, 91B: 229–235 (1988); WO 89/08667 published 21 Sep. 1989; WO 89/09792 published 19 Oct. 1989; and Binkert et al., *EMBO J.*, 8: 2497–2502 (1989).

The term "body fluid" refers to a biological sample of liquid from a mammal, preferably from a human. Such fluids include aqueous fluids such as serum, plasma, lymph fluid, synovial fluid, follicular fluid, seminal fluid, amniotic fluid, milk, whole blood, urine, cerebrospinal fluid, saliva, sputum, tears, perspiration, mucus, tissue culture medium, tissue extracts, and cellular extracts.

As used herein, "human IGF receptor" refers to any receptor for an IGF found in humans and includes the Type 1 and Type 2 IGF receptors in humans to which both human IGF-I and IGF-II bind, such as the placental Type 1 IGF-I receptor, etc.

A "disorder" is any condition that would benefit from treatment with an IGF, including but not limited to, for example, lung diseases, hyperglycemic disorders as set forth below, renal disorders, such as acute and chronic renal insufficiency, end-stage chronic renal failure, glomerulonephritis, interstitial nephritis, pyelonephritis, glomerulosclerosis, e.g., Kimmelstiel-Wilson in diabetic patients and kidney failure after kidney transplantation, obesity, GH-insufficiency, Turner's syndrome, Laron's syndrome, short stature, undesirable symptoms associated with aging such as obesity and increased fat mass-to-lean ratios, immunological disorders such as immunodeficiencies including decreased CD4 counts and decreased immune tolerance or chemotherapy-induced tissue damage, bone marrow transplantation, diseases or insufficiencies of cardiac structure or function such as heart dysfunctions and congestive heart failure, neuronal, neurological, or neuromuscular disorders, e.g., peripheral neuropathy, multiple sclerosis, muscular dystrophy, or myotonic dystrophy, and catabolic states, associated with wasting caused by any condition, including, e.g., trauma or wounding or infection such as with a bacterium or human virus such as HIV, wounds, skin disorders, gut structure and function that need restoration, and so forth. The disorder being treated may be a combination of two or more of the above disorders. The preferred disorders targeted for treatment herein are diabetes and obesity, heart dysfunctions, kidney disorders, neurological disorders, whole body growth disorders, and immunological disorders.

As used herein, the term "hyperglycemic disorders" refers to all forms of diabetes and disorders resulting from insulin resistance, such as Type I and Type II diabetes, as well as severe insulin resistance, hyperinsulinemia, and hyperlipidemia, e.g., obese subjects, and insulin-resistant diabetes, such as Mendenhall's Syndrome, Werner Syndrome, leprechaunism, lipoatrophic diabetes, and other lipoatrophies. The preferred hyperglycemic disorder is diabetes, especially Type 1 and Type II diabetes. "Diabetes" itself refers to a progressive disease of carbohydrate metabolism involving inadequate production or utilization of insulin and is characterized by hyperglycemia and glycosuria.

As used herein, the term "treating" refers to both therapeutic treatment and prophylactic or preventative measures. Those in need of treatment include those already with the disorder as well as those prone to having the disorder or diagnosed with the disorder or those in which the disorder is to be prevented. Consecutive treatment or administration refers to treatment on at least a daily basis without interruption in treatment by one or more days. Intermittent treatment or administration, or treatment or administration in an intermittent fashion, refers to treatment that is not consecutive, but rather cyclic in nature. The treatment regime herein can be either consecutive or intermittent.

As used herein, the term "hypoglycemic agent" refers to compounds that are useful for regulating glucose metabolism, preferably oral agents. More preferred herein for human use are insulin and the sulfonylurea class of oral hypoglycemic agents, which cause the secretion of insulin by the pancreas. Examples include glyburide, glipizide, and gliclazide. In addition, agents that enhance insulin sensitivity or are insulin sensitizing, such as biguanides (including metformin and phenformin) and thiazolidenediones such as REZULIN™ (troglitazone) brand insulin-sensitizing agent, and other compounds that bind to the PPARy nuclear receptor, are within this definition, and also are preferred.

As used herein, "insulin" refers to any form of insulin from any species, and whether natively, synthetically, or recombinantly derived. Preferably it is NPH insulin.

As used herein, "active" or "biologically-active" IGF in the context of changing serum and tissue levels of endogenous IGF refers to IGF that binds to its receptor or otherwise causes a biological activity to occur, such as those biological activities of endogenous or exogenous IGF referred to above.

The term "amino acid" within the scope of the present invention is used in its broadest sense and is meant to include the naturally-occurring L α-amino acids or residues. The Li commonly used one- and three-letter abbreviations for naturally-occurring amino acids are used herein (Lehninger, *Biochemistry*, 2d ed., pp. 71–92, (Worth Publishers: New York, 1975). The term includes D-amino acids as well as chemically-modified amino acids such as amino acid analogs, naturally-occurring amino acids that are not usually incorporated into proteins such as norleucine, and chemically-synthesized compounds having properties known in the art to be characteristic of an amino acid. For example, analogs or mimetics of phenylalanine or proline, which allow the same conformational restriction of the peptide compounds as natural Phe or Pro, are included within the definition of amino acid. Such analogs and mimetics are referred to herein as "functional equivalents" of an amino acid. Other examples of amino acids are listed by Roberts and Vellaccio, *The Peptides: Analysis, Synthesis, Biology*, Eds. Gross and Meiehofer, Vol. 5, p. 341 (Academic Press, Inc.: N.Y. 1983).

The term "conservative" amino acid substitution as used herein to refer to amino acid substitutions that substitute functionally-equivalent amino acids. Conservative amino acid changes result in silent changes in the amino acid sequence of the resulting peptide. For example, one or more amino acids of a similar polarity act as functional equivalents and result in a silent alteration within the amino acid sequence of the peptide. The largest sets of conservative amino acid substitutions include:

(1) hydrophobic: His, Trp, Tyr, Phe, Met, Leu, Ile, Val, Ala;

(2) neutral hydrophilic: Cys, Ser, Thr;

(3) polar: Ser, Thr, Asn, Gln;

(4) acidic/negatively charged: Asp, Glu;

(5) charged: Asp, Glu, Arg, Lys, His;

(6) basic/positively charged: Arg, Lys, His;

(7) basic: Asn, Gln, His, Lys, Arg;

(8) residues that influence chain orientation: Gly, Pro; and (9) aromatic: Trp, Tyr, Phe, His.

In addition, "structurally-similar" amino acids can substitute conservatively for some of the specific amino acids. Groups of structurally-similar amino acids include: (Ile, Leu, and Val); (Phe and Tyr); (Lys and Arg); (Gln and Asn); (Asp and Glu); and (Gly and Ala). In this regard, it is understood that amino acids are substituted on the basis of side-chain bulk, charge, and/or hydrophobicity. Amino acid residues are classified into four major groups:

Acidic: The residue has a negative charge due to loss of an H ion at physiological pH and the residue is attracted by aqueous solution so as to seek the surface positions in the conformation of a peptide in which it is contained when the peptide is in aqueous solution.

Basic: The residue has a positive charge due to association with an H ion at physiological pH and the residue is attracted by aqueous solution so as to seek the surface positions in the conformation of a peptide in which it is contained when the peptide is in aqueous medium at physiological pH.

Neutral/non-polar: The residues are not charged at physiological pH and the residue is repelled by aqueous solution so as to seek the inner positions in the conformation of a peptide in which it is contained when the peptide is in aqueous medium. These residues are also designated "hydrophobic residues."

Neutral/polar: The residues are not charged at physiological pH, but the residue is attracted by aqueous solution so as to seek the outer positions in the conformation of a peptide in which it is contained when the peptide is in aqueous medium.

"Amino acid" residues can be further classified as cyclic or non-cyclic, and aromatic or non-aromatic with respect to their side-chain groups, these designations being commonplace to the skilled artisan. The table below shows the types of conservative substitutions that can be made.

| Original Residue | Exemplary Conservative Substitution | Preferred Conservative Substitution |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn | Asn |
| Glu | Asp | Asp |
| Gly | Pro | Pro |
| His | Asn, Gln, Lys, Arg | Arg |
| Ile | Leu, Val, Met, Ala, Phe | Leu |
| Leu | Ile, Val, Met, Ala, Phe | Ile |
| Lys | Arg, Gln, Asn | Arg |
| Met | Leu, Phe, Ile | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala | Leu |

Peptides synthesized by the standard solid-phase synthesis techniques described herein, for example, are not limited to amino acids encoded by genes for substitutions involving the amino acids. Commonly-encountered amino acids that are not encoded by the genetic code include, for example, those described in WO 90/01940 and in the table below, as well as, for example, 2-amino adipic acid (Aad) for Glu and Asp; 2-aminopimelic acid.(Apm) for Glu and Asp; 2-aminobutyric (Abu) acid for Met, Leu, and other aliphatic amino acids; 2-aminoheptanoic acid (Ahe) for Met, Leu, and other aliphatic amino acids; 2-aminoisobutyric acid (Aib) for Gly; cyclohexylalanine (Cha) for Val, Leu and Ile; homoarginine (Har) for Arg and Lys; 2,3-diaminopropionic acid (Dpr) for Lys, Arg, and His; N-ethylglycine (EtGly) for Gly, Pro, and Ala; N-ethylglycine (EtGly) for Gly, Pro, and Ala; N-ethylasparigine (EtAsn) for Asn, and Gln; hydroxyllysine (Hyl) for Lys; allohydroxyllysine (AHyl) for Lys; 3-(and 4-)hydroxyproline (3Hyp, 4Hyp) for Pro, Ser, and Thr; allo-isoleucine (AIle) for Ile, Leu, and Val; ρ-amidinophenylalanine for Ala; N-methylglycine (MeGly, sarcosine) for Gly, Pro, and Ala; N-methylisoleucine (MeIle) for Ile; norvaline (Nva) for Met and other aliphatic amino acids; w norleucine (Nle) for Met and other aliphatic amino acids; ornithine (Orn) for Lys, Arg and His; citrulline (Cit) and methionine sulfoxide (MSO) for Thr, Asn, and Gln; and N-methylphenylalanine (MePhe), trimethylphenylalanine, halo-(F-, Cl-, Br-, or I-)phenylalanine, or trifluorylphenylalanine for Phe.

| Abbreviations used in the Specification | |
|---|---|
| Compound | Abbreviation |
| Acetyl | Ac |
| Alanine | Ala |
| 3-(2-Thiazolyl)-L-alanine | Tza |
| Arginine | Arg |
| Asparagine | Asn |
| Aspartic acid | Asp |
| t-Butyloxycarbonyl | Boc |

-continued

Abbreviations used in the Specification

| Compound | Abbreviation |
| --- | --- |
| Benzotriazol-1-yloxy-tris-(dimethyl-amino)phosphonium-hexafluorophosphate | Bop |
| β-Alanine | βAla |
| β-Valine | βVal |
| β-(2-Pyridyl)-alanine | Pal(2) |
| β-(3-Pyridyl)-alanine | Pal(3) |
| β-(4-Pyridyl)-alanine | Pal(4) |
| β-(3-N-Methylpyridinium)-alanine | PalMe(3) |
| t-Butyl | tBu, But |
| t-Butyloxycarbonyl | Boc |
| Caffeic acid | Caff |
| Cysteine | Cys |
| Cyclohexylalanine | Cha |
| Cyclohexylglycine | Chg |
| 3,5-Dinitrotyrosine | $Tyr(3,5-No_2)$ |
| 3,5-Diiodotyrosine | Tyr(3,5-I) |
| 3,5-Dibromotyrosine | Tyr(3,5-Br) |
| 9-Fluorenylmethyloxy-carbonyl | Fmoc |
| Glutamine | Gln |
| Glutamic acid | Glu |
| γ-Carboxyglutamic acid | Gla |
| Glycine | Gly |
| Histidine | His |
| Homoarginine | hArg |
| 3-Hydroxyproline | Hyp |
| Isoleucine | Ile |
| Leucine | Leu |
| tert-Leucine | Tle |
| Lysine | Lys |
| Mercapto-β, β-cyclopentamethylene-propionic acid | Mpp |
| Mercaptoacetic acid | Mpa |
| Mercaptopropionic acid | Mpr |
| Methionine | Met |
| 1-Naphthylalanine | Nal(1) |
| 2-Naphthylalanine | Nal(2) |
| Nicotinic acid | Nic |
| Nipecotic acid | Npa |
| N-methyl nicotinic acid | NicMe |
| Norarginine | nArg |
| Norleucine | Nle |
| Norvaline | Nva |
| Ornithine | Orn |
| Ornithine-derived dimethylamidinium | Orn ($N^6$—$C_3H_7N$) |
| Phenylalanine | Phe |
| p-Guanidinophenylalanine | Phe(Gua) |
| p-Aminophenylalanine | Phe($NH_2$) |
| p-Chlorophenylalanine | Phe(Cl) |
| p-Flurophenylalanine | Phe(F) |
| p-Nitrophenylalanine | Phe($NO_2$) |
| p-Hydroxyphenylglycine | Pgl(OH) |
| p-Toluenesulfonyl | Tos |
| m-Amidinophenylalanine | mAph |
| p-Amidinophenylalanine | pAph |
| Phenylglycine | Pgl |
| Phenylmalonic acid | Pma |
| Proline | Pro |
| 4-Quinolinecarboxy | 4-Qca |
| Sarcosine | Sar |
| Serine | Ser |
| Threonine | Thr |
| Tryptophan | Trp |
| Tyrosine | Tyr |
| 3-iodotyrosine | Tyr(3-I) |
| O-Methyl tyrosine | Tyr(Me) |
| Valine | Val |

*Amino acids of D configuration are denoted by D-prefix using three-letter code (e.g., D-Ala, D-Cys, D-Asp, D-Trp).

"Peptides" include molecules having at least two amino acids and include polypeptides having at least about 60 amino acids. Preferably, the peptides have about 10 to about 60 amino acids, more preferably about 10–25, and most preferably about 12–25 amino acids. The definition includes linear and cyclic peptides, peptide derivatives, their salts, or optical isomers.

"Growth hormone releasing peptides or factors" ("GHRP" or "GHRF") are described below, as are secretagogues. A "growth hormone releasing hormone" ("GHRH") can be any hormone that releases GH from the cells' or tissue. "Growth hormone in combination with a growth hormone binding protein" ("GH" plus "GHBP") means a GH complexed with or otherwise associated with one of its binding proteins. Similarly, "IGF in combination with an IGF binding protein" ("IGF" plus "IGFBP") refers to an IGF complexed with or otherwise associated with one of its IGFBPs.

As used herein, an "amide bond-forming substituent contained in an amino acid side-chain", a "side-chain amide bond-forming substituent", and their grammatical variants, are defined to include (1) any carboxy substituent contained in the side-chain ("R" group) of an amino acid wherein the carboxy substituent is capable of forming an amide linkage with an amino group contained in another molecule, i.e., the carboxy substituent reacts with an amino group contained in another molecule to form an amide linkage; and (2) any amino substituent contained in the side-chain ("R" group) of an amino acid wherein the amino substituent is capable of forming an amide linkage with a carboxy group contained in another molecule, i.e., the amino substituent reacts with a carboxy group contained in another molecule to form an amide linkage.

As used herein, "differentially-removable" protecting or protective groups are defined as any pair of protective groups capable of protecting a first amide bond-forming substituent and a second amide bond-forming substituent, wherein it is possible to deprotect the first amide bond-forming substituent protected with one member of the pair under conditions which do not deprotect the second amide bond-forming substituent protected with the other member of the pair. Differentially-removable protecting groups are also referred to herein as "orthogonal" protecting groups, and the differentially-removable protection conferred by such protective groups is referred to herein as "orthogonal" protection.

As used herein, the term "pulmonary administration" refers to administration of a formulation of the invention through the lungs by inhalation. As used herein, the term "inhalation" refers to intake of air to the alveoli. In specific examples, intake can occur by self-administration of a formulation of the invention while inhaling through a nebulizer or other aerosol-delivery device, or by administration via a respirator, e.g., to a patient on a respirator. The term "inhalation" used with respect to a formulation of the invention is synonymous with "pulmonary administration."

As used herein, the term "iparenteral" refers to introduction of a peptide of the invention into the body by other than the intestines, and in particular, intravenous (i.v.), intraarterial (i.a.), intraperitoneal (i.p.), intramuscular (i.m.), intraventricular, and subcutaneous (s.c.) routes.

As used herein, the term "aerosol" refers to suspension in the air. In particular, aerosol refers to the formation of particles or particulates in a formulation of the invention and its suspension in the air. According to the present invention, an aerosol formulation is a formulation comprising a peptide of the present invention that is suitable for aerosolization, i.e., formation of particles or particulates and suspension in the air, for inhalation or pulmonary administration.

As used herein, the term "dispersant" refers to an agent that assists aerosolization of the peptide or absorption of the protein in lung tissue, or both. Preferably, the dispersant is pharmaceutically acceptable. As used herein, the modifier "pharmaceutically-acceptable" means approved by a regulatory agency of the federal or a state government or listed in the U.S. Pharmacopeia or other generally recognized pharmacopeia for use in animals, and more particularly in humans.

B. Modes for Carrying Out the Invention

The present invention relates to various classifications of peptides having the function of displacing IGFBP-1. In one embodiment, the peptide comprises the following sequence:

$Xaa_{(1-4)}CysXaa_{(6)}Xaa_{(7)}GlyXaa_{(9)}Xaa_{(10)}Xaa_{(11)}Xaa_{(12)}Xaa_{(13)}CysXaa_{(15)}Xaa_{(16)}Xaa_{(17)}Xaa_{(18)}$ (SEQ ID NO:1), wherein $Xaa_{(1-4)}$ is absent or is between 1 and 4 amino acids of any kind, $Xaa_{(6)}$, $Xaa_{(7)}$, $Xaa_{(9)}$, $Xaa_{(11)}$, $Xaa_{(15)}$, and $Xaa_{(16)}$ are independently any amino acid, $Xaa_{(10)}$ and $Xaa_{(13)}$ are independently Leu or Nle, and $Xaa_{(12)}$, $Xaa_{(17)}$, and $Xaa_{(18)}$ are independently Nal(1), His, Phe, Trp, Tyr, Pro, Gln, or Met.

Preferably, in SEQ ID NO:1 above, $Xaa_{(1-4)}$, $Xaa_{(6)}$, $Xaa_{(7)}$, $Xaa_{(9)}$, $Xaa_{(11)}$, $Xaa_{(15)}$, and $Xaa_{(16)}$ are independently Ala, Leu, Ile, Glu, Arg, Val, Gly, Gln, Ser, Met, Pro, Thr, Asn, Lys, or Trp, more preferably Ala, Glu, Arg, Val, Gly, Gln, Ser, Pro, Asn, or Lys. Independently, or in combination with this, preferably $Xaa_{(12)}$, $Xaa_{(17)}$ and $Xaa_{(18)}$ are independently Phe, Trp, Tyr, Pro, Gln, or Met, more preferably Phe, Trp, or Tyr, and most preferably Phe or Trp. Independently, or in combination with this, $Xaa_{(9)}$ is Ala, Arg, Asn, or Pro. In more preferred embodiments, $Xaa_{(6)}$ is Arg, $Xaa_{(7)}$ is Ala, $Xaa_{(9)}$ is Pro, $Xaa_{(11)}$ is Gln, $Xaa_{(12)}$ is Trp, $Xaa_{(15)}$ is Glu, $Xaa_{(16)}$ is Lys, $Xaa_{(17)}$ is Tyr, and/or $Xaa_{(18)}$ is Phe.

One preferred peptide comprising SEQ ID NO:1 comprises the following sequence:

GluAlaArgValCysArgAlaGlyPro-LeuGlnTrpLeuCysGluLysTyrPhe (SEQ ID NO:2).

Another preferred set of peptides comprising SEQ ID NO:1 is $CysXaa_{(6)}Xaa_{(7)}GlyXaa_{(9)}Xaa_{(10)}Xaa_{(11)}TrpXaa_{(13)}CysXaa_{(15)}Xaa_{(16)}Xaa_{(17)}Xaa_{(18)}$ (SEQ ID NO:3). More specifically preferred such peptides comprise one of the following sequences: SEQ ID NO:4, 5,6,7,8,9,10, or 11.

Also preferred is the peptide having after the C-terminal $Xaa_{(18)}$ residue in SEQ ID NO:1 the sequence $Xaa_{(19)}ThrTyr$, wherein $Xaa_{(19)}$ is any amino acid, preferably Ala, Ser, Gln, Asp, Glu, or Lys, and more preferably Ser. More preferred such peptides comprise the following sequence:

$Xaa_{(1-4)}CysArgAlaGlyProLeuGlnTrpLeuCysGluXaa_{(16)}$ TyrPheXaa$_{(19)}$ThrTyr (SEQ ID NO:12), wherein $Xaa_{(16)}$ is Lys or His and $Xaa_{(19)}$ is Ala, Ser, Gln, Asp, Glu, or Lys, with still more preferred peptides comprising one of the following sequences: SEQ ID NO:13, 14, 15, 16, 17, 18, 19, 20, 21, 22, 23, 24, 25, 26, 27, 28, or 29. Of these latter peptides, most preferred are SEQ ID NO:20, 21, or 29.

The most preferred of those peptides comprising SEQ ID NO:1 comprise one or the 13 following sequences: SEQ ID NO:4, 5, 6, 7, 8, 9, 10, 11, 14, 15, 16, 17, 18, 19, 20, 21, 22, 23, 24, 25, 26, 27, 28, or 29. In another preferred aspect, the peptide comprising SEQ ID NO:1 has a C-terminal fusion (e.g., a sequence attached to C-terminal residue $Xaa_{(18)}$) comprising the following sequence:

GlyGlyGlySerGlyGlyAlaGlnHisAspGluAlaVal AspAsnLysPheAsnLysGluGlnGlnAsnAlaPheTyrGlu IleLeuHisLeuProAsnLeuAsnGluGluGlnArgAsnAla PheIleGlnSerLeuLysAspAspProSerGlnSerAlaAsn LeuLeuAlaGluAlaLysLysLeuAsnAspAlaGlnAla ProAsnValAspMetAsn (SEQ ID NO:30).

In another preferred embodiment, the peptide comprising after the C-terminal $Xaa_{(18)}$ residue in SEQ ID NO:1 the sequence $Xaa_{(19)}ThrTyr$ has a C-terminal fusion (e.g., a sequence attached to the C-terminal Tyr residue) which fusion comprises SEQ ID NO:30.

In another aspect, the invention entails a constrained helical peptide comprising a sequence of nine amino acid residues having a first terminal residue and a second terminal residue, wherein said residues flank an internal sequence of seven amino acids and have side-chains linked, i.e., covalently bonded, to each other to form a locking moiety and thereby constrain the peptide. Preferably, the internal sequence is $Xaa_{(7)}LeuAlaXaa_{(10)}Xaa_{(11)}Xaa_{(12)}Xaa_{(13)}$ (SEQ ID NO:31), wherein $Xaa_{(7)}$, $Xaa_{(11)}$, $Xaa_{(12)}$, and $Xaa_{(13)}$ are independently Nal(1), His, Phe, Trp, Tyr, Pro, Gln, or Met, and $Xaa_{(10)}$ is any amino acid.

In another embodiment, the invention provides a peptide comprising the following sequence:

$Xaa_{(1-4)}Xaa_{(5)}Xaa_{(6-7)}ProLeuGluXaa_{(11)}LeuAlaXaa_{(14)}$ $Xaa_{(15)}Xaa_{(16)}Xaa_{(17)}GluXaa_{(19)}$ (SEQ ID NO:32), wherein $Xaa_{(1-4)}$ is absent or is between 1 and 4 amino acids of any kind; $Xaa_{(5)}$ is any amino acid, $Xaa_{(6-7)}$ is absent or is between 1 and 2 amino acids, $Xaa_{(14)}$ and $Xaa_{(15)}$ are independently any amino acid, $Xaa_{(11)}$ and $Xaa_{(16)}$ are independently Nal(1), His, Phe, Trp, Tyr, Pro, Gln, or Met, $Xaa_{(17)}$ is absent or is Nal(1), His, Phe, Trp, Tyr, Pro, Gln, or Met, and $Xaa_{(19)}$ is absent or is Gly.

In a preferred aspect, $Xaa_{(1-4)}$ is absent and an acetyl group is attached to $Xaa_{(5)}$. In another preferred aspect, the Glu residues in SEQ ID NO:32 are joined by forming amides with 1,5-diaminopentane.

In another preferred aspect, C-terminal to the C-terminal $Xaa_{(19)}$ in SEQ ID NO:32 is the sequence $Xaa_{(20)}ThrTyr$, wherein $Xaa_{(20)}$ is any amino acid, preferably Ala, Ser, Gln, Asp, Glu, or Lys.

In another aspect, this peptide comprises the following sequence:

$Xaa_{(5)}Xaa_{(6-7)}ProLeuGluXaa_{(11)}LeuAlaXaa_{(14)}Xaa_{(15)}$ $Xaa_{(16)}Xaa_{(17)}GluGly$ (SEQ ID NO:33), wherein $Xaa_{(6-7)}$ is two amino acids.

In the above peptide preferably, independently or in combination, $Xaa_{(5)}$ is Arg, $Xaa_{(6-7)}$ is absent or is AlaGly, $Xaa_{(11)}$ is Trp, $Xaa_{(14)}$ is Glu, $Xaa_{(15)}$ is Lys, $Xaa_{(16)}$ is Tyr, and /or $Xaa_{(17)}$ is Phe.

In specific aspects, the peptide comprises one of the following sequences: ArgAlaGlyProLeuGluTrpLeuAlaG-luLysTyrGluGly (SEQ ID NO:34); ArgProLeuGluTr-pLeuAlaGluLysTyrPheGlu (SEQ ID NO:35); or ArgAlaG-lyProLeuGluTrpLeuAlaGluLysTyrPheGlu (SEQ ID NO:36).

The peptides of this invention can be made by chemical synthesis or by employing recombinant technology. These methods are known in the art. Chemical synthesis, especially solid-phase synthesis, is preferred for short (e.g., less than 50 residues) peptides or those containing unnatural or unusual amino acids such as D-Tyr, ornithine, amino-adipic acid, and the like. Recombinant procedures are preferred for longer polypeptides. When recombinant procedures are selected, a synthetic gene may be constructed de novo or a natural gene may be mutated by, for example, cassette mutagenesis.

A useful method for identification of certain residues or regions of the peptides herein suitable for amino acid substitution other than those described herein is called alanine-scanning mutagenesis as described by Cunningham and Wells, *Science*, 244:1081–1085 (1989). Here a residue or group of target co residues are identified (e.g. charged residues such as Arg, Asp, His, Lys, and Glu) and replaced by a neutral or negatively-charged amino acid to affect the interaction of the amino acids with the surrounding aqueous environment in or outside the cell. Those domains demonstrating functional sensitivity to the substitution then are refined by introducing further or other variations at or for the sites of substitution. Thus, while the site for introducing an amino acid sequence variation is predetermined, the nature of the mutation per se need not be predetermined. For example, to optimize the performance of a mutation at a given site, Ala-scanning or random mutagenesis may be conducted at the target codon or region and the expressed compound screened for the optimal combination of desired activity.

Phage display of protein or peptide libraries offers another methodology for the selection of compounds with improved affinity, altered specificity, or improved stability (Smith, *Curr. Opin. Biotechnol.*, 2:668–673 (1991)). High affinity proteins, displayed in a monovalent fashion as fusions with the M13 gene III coat protein (Clackson et al., *Trends Biotechnol*. 12:173–183 (1994)), can be identified by cloning and sequencing the corresponding DNA packaged in the phagemid particles after a number of rounds of binding selection.

Other peptides include the fusion to the N- or C-tenminus of the peptides described herein of immunogenic polypeptides, e.g., bacterial polypeptides such as beta-lactamase or an enzyme encoded by *E. coli* Trp locus or yeast protein, and C-terminal fusion with proteins having a long half-life such as immunoglobulin constant region or other immunoglobulin regions, albumin, or ferritin as described in WO 89/02922 published 6 Apr. 1989. Further, free functional groups on the side-chains of the amino acid residues can also be modified by amidation, acylation, or other substitution, which can, for example, change the solubility of the peptides without affecting their activity.

Set forth below are exemplary general recombinant procedures.

From a purified IGF and its amino acid sequence, for example, an IGF agonist that is a peptidyl mutant of an IGF may be produced using recombinant DNA techniques. These techniques contemplate, in simplified form, taking the gene, either natural or synthetic, encoding the peptide; inserting it into an appropriate vector; inserting the vector into an appropriate host cell; culturing the host cell to cause expression of the gene; and recovering or isolating the peptide produced thereby. Preferably, the recovered peptide is then purified to a suitable degree.

Somewhat more particularly, the DNA sequence encoding a peptidyl IGF agonist is cloned and manipulated so that it may be expressed in a convenient host. DNA encoding parent polypeptides can be obtained from a genomic library, from cDNA derived from mRNA from cells expressing the peptide, or by synthetically constructing the DNA sequence (Sambrook et al., *Molecular Cloning: A Laboratory Manual* (2d ed.) (Cold Spring Harbor Laboratory: N.Y., 1989)).

The parent DNA is then inserted into an appropriate plasmid or vector that is used to transform a host cell. In general, plasmid vectors containing replication and control sequences derived from species compatible with the host cell are used in connection with those hosts. The vector ordinarily carries a replication site, as well as sequences encoding proteins or peptides that are capable of providing phenotypic selection in transformed cells.

For example, *E. coli* may be transformed using pBR322, a plasmid derived from an *E. coli* species (Mandel et al., *J. Mol. Biol*. 53: 154 (1970)). Plasmid pBR322 contains genes for ampicillin and tetracycline resistance, and thus provides easy means for selection. Other vectors include different features such as different promoters, which are often important in expression. For example, plasmids pKK223-3, pDR720, and pPL-lambda represent expression vectors with the tac, trp, or $P_L$ promoters that are currently available (Pharmacia Biotechnology).

One preferred vector is pB0475. This vector contains origins of replication for phage and *E. coli* that allow it to be shuttled between such hosts, thereby facilitating both mutagenesis and expression (Cunningham et al., *Science*, 243: 1330–1336 (1989), U.S. Pat. No. 5,580,723). Other preferred vectors are pR1T5 and pR1T2T (Pharmacia Biotechnology). These vectors contain appropriate promoters followed by the Z domain of protein A, allowing genes inserted into the vectors to be expressed as fusion proteins.

Other preferred vectors can be constructed using standard techniques by combining the relevant traits of the vectors described above. Relevant traits include the promoter, the ribosome binding site, the decorsin or ornatin gene or gene fusion (the Z domain of protein A and decorsin or ornatin and its linker), the antibiotic resistance markers, and the appropriate origins of replication.

The host cell may be prokaryotic or eukaryotic. Prokaryotes are preferred for cloning and expressing DNA sequences to produce parent IGF-I polypeptide, segment-substituted peptides, residue-substituted peptides, and peptide variants. For example, *E. coli* K12 strain 294 (ATCC No. 31446) may be used as well as *E. coli* B, *E. coli* X1776 (ATCC No. 31537), and *E. coli* c600 and c600hfl, *E. coli* W3110 (F-, gamma-, prototrophic/ATCC No. 27325), bacilli such as *Bacillus subtilis*, and other enterobacteriaceae such as *Salmonella typhimurium* or *Serratia marcesans*, and various Pseudomonas species. The preferred prokaryote is *E. coli* W3110 (ATCC 27325). When expressed by prokaryotes the peptides typically contain an N-terminal methionine or a formyl methionine and are not glycosylated. In the case of fusion proteins, the N-terminal methionine or formyl methionine resides on the amino terminus of the fusion protein or the signal sequence of the fusion protein. These examples are, of course, intended to be illustrative rather than limiting.

In addition to prokaryotes, eukaryotic organisms, such as yeast cultures, or cells derived from multicellular organisms may be used. In principle, any such cell culture is workable. However, interest has been greatest in vertebrate cells, and propagation of vertebrate cells in culture (tissue culture) has W become a reproducible procedure. *Tissue Culture*, Academic Press, Kruse and Patterson, editors (1973). Examples of such useful host cell lines are VERO and HeLa cells, Chinese Hamster Ovary (CHO) cell lines, W138, 293, BHK, COS-7 and MDCK cell lines.

A variation on the above procedures contemplates the use of gene fusions, wherein the gene encoding the desired peptide is a associated, in the vector, with a gene encoding another protein or a fragment of another protein. This results in the desired peptide being produced by the host cell as a fusion with another protein or peptide. The "other" protein or peptide is often a protein or peptide that can be secreted by the cell, making it possible to isolate and purify the desired peptide from the culture medium and eliminating the necessity of destroying the host cells that arises when the desired peptide remains inside the cell. Alternatively, the fusion protein can be expressed intracellularly. It is useful to use fusion proteins that are highly expressed.

The use of gene fusions, though not essential, can facilitate the expression of heterologous peptides in *E. coli* as well as the subsequent purification of those gene products. Harris, in *Genetic Engineering*, Williamson, R., Ed. (Academic Press, London, Vol. 4, 1983), p. 127; Ljungquist et al., *Eur. J. Biochem.*, 186: 557–561 (1989) and Ljungquist et al., *Eur. J. Biochem.*, 186: 563–569 (1989). Protein A fusions are often used because the binding of protein A, or more specifically the Z domain of protein A, to IgG provides an "affinity handle" for the purification of the fused protein. See Nilsson et al., *Protein Engineering*, 1: 107–113 (1987). It has also been shown that many heterologous proteins are degraded when expressed directly in *E. coli*, but are stable when expressed as fusion proteins. Marston, *Biochem J.*, 240: 1 (1986).

After expression and secretion, for example, from *E. coli*, the fusion protein is cleaved to yield free peptide, which can be purified from the reaction mix. The cleavage may be accomplished using chemicals, such as cyanogen bromide, which cleaves at a methionine, or hydroxylamine, which cleaves between an Asn and Gly residue. Using standard recombinant DNA methodology, the nucleotide base pairs encoding these amino acids may be inserted just prior to the 5' end of the gene encoding the desired peptide.

Alternatively, one can employ proteolytic cleavage of fusion protein (Carter, in *Protein Purification: From Molecular Mechanisms to Large-Scale Processes*, Ladisch et al., eds. (American Chemical Society Symposium Series No. 427, 1990), Ch 13, pages 181–193; Varadarajan et al., *Proc. Natl. Acad. Sci. USA*, 82: 5681–5684 (1985); Castellanos-Serra et al., *FEBS Letters*, 378: 171–176 (1996); Nilsson et al., *J. Biotechnol.*, 48: 241–250 (1996)).

Proteases such as Factor Xa, thrombin, subtilisin, or trypsin, or its mutants, and a number of others have been successfully used to cleave fusion proteins. Trypsin is preferred because peptide-Z-domain fusions are found to be readily cleaved by this protease. Detailed procedures for employing trypsin as protease are found in Smith, Methods in *Mol. Biol.*, 32: 289–196 (1994). Typically, a peptide linker that is amenable to cleavage by the protease used is inserted between the "other" protein (e.g., the Z domain of protein A) and the desired peptide. Using recombinant DNA methodology, the nucleotide base pairs encoding the linker are inserted between the genes or gene fragments coding for the other proteins. Proteolytic cleavage of the partially-purified fusion protein containing the correct linker can then be carried out on either the native fusion protein, or the reduced or denatured fusion protein.

The peptide may or may not be properly folded when expressed as a fusion protein. Also, the specific peptide linker containing the cleavage site may or may not be accessible to the protease. These factors determine whether the fusion protein must be denatured and refolded, and if so, whether these procedures are employed before or after cleavage.

When denaturing and refolding are needed, typically the peptide is treated with a chaotrope, such as guanidine HCl, and is then treated with a redox buffer, containing, for example, reduced and oxidized dithiothreitol or glutathione at the appropriate ratios, pH, and temperature, such that the peptide is refolded to its native structure.

As well as by recombinant methods, peptides of the invention can be conveniently prepared using solid phase peptide synthesis (Merrifield, *J. Am, Chem. Soc.*, 85: 2149 (1964); Houghten, *Proc. Natl. Acad. Sci. USA*, 82: 5132 (1985)), although other equivalent chemical syntheses known in the art are employable. Solid-phase synthesis is initiated from the C-terminus of the peptide by coupling a protected α-amino acid to a suitable resin. Such a starting material can be prepared by attaching an α-amino-protected amino acid by an ester linkage to a chloromethylated resin or a hydroxymethyl resin, or by an amide bond to a BHA resin or MBHA resin. The preparation of the hydroxymethyl resin is described by Bodansky et al., *Chem. Ind.* (*London*), 38: 1597–1598 (1966). Chloromethylated resins are commercially available from BioRad Laboratories, Richmond, Calif. and from Lab. Systems, Inc. The preparation of such a resin is described by Stewart et al., "Solid Phase Peptide Synthesis" (Freeman & Co., San Francisco 1969), Chapter 1, pp. 1–6. BHA and MBHA resin supports are commercially available and are generally used only when the desired polypeptide being synthesized has an unsubstituted amide at the C-terminus.

The amino acids are coupled to the peptide chain using techniques well known in the art for the formation of peptide bonds. One method involves converting the amino acid to a derivative that will render the carboxyl group more susceptible to reaction with the free N-terminal amino group of the peptide fragment. For example, the amino acid can be converted to a mixed anhydride by reaction of a protected amino acid with ethylchloroformate, phenyl chloroformate, sec-butyl chloroformate, isobutyl chloroformate, pivaloyl chloride or like acid chlorides. Alternatively, the amino acid can be converted to an active ester such as a 2,4,5-trichlorophenyl ester, a pentachlorophenyl ester, a pentafluorophenyl ester, a p-nitrophenyl ester, a N-hydroxysuccinimide ester, or an ester formed from 1-hydroxybenzotriazole.

Another coupling method involves use of a suitable coupling agent such as N,N'-dicyclohexylcarbodiimide or N,N'-diisopropyl-carbodiimide. Other appropriate coupling agents, apparent to those skilled in the art, are disclosed in E. Gross & J. Meienhofer, *The Peptides: Analysis, Structure, Biology*, Vol. I: Major Methods of Peptide Bond Formation (Academic Press: New York, 1979).

It should be recognized that the α-amino group of each amino acid employed in the peptide synthesis must be protected during the coupling reaction to prevent side reactions involving their active α-amino function. It should also be recognized that certain amino acids contain reactive side-chain functional groups (e.g., sulfhydryl, amino, carboxyl, and hydroxyl) and that such functional groups must also be protected with suitable protecting groups to prevent a chemical reaction from occurring at that site during both the initial and subsequent coupling steps. Suitable protecting groups, known in the art, are described in Gross and Meienhofer, *The Peptides: Analysis, Structure, Biology*, Vol.3: "Protection of Functional Groups in Peptide Synthesis" (Academic Press: New York, 1981).

In the selection of a particular side-chain protecting group to be used in synthesizing the peptides, the following general rules are followed. An α-amino protecting group (a) must render the α-amino function inert under the conditions employed in the coupling reaction, (b) must be readily removable after the coupling reaction under conditions that will not remove side-chain protecting groups and will not alter the structure of the peptide fragment, and (c) must eliminate the possibility of racemization upon activation immediately prior to coupling. A side-chain protecting group (a) must render the side-chain functional group inert under the conditions employed in the coupling reaction, (b) must be stable under the conditions employed in removing the amino protecting group, and (c) must be readily removable upon completion of the desired amino acid peptide under reaction conditions that will not alter the structure of the peptide chain.

It will be apparent to those skilled in the art that the protecting groups known to be useful for peptide synthesis will vary in reactivity with the agents employed for their removal. For example, certain protecting groups such as triphenylmethyl and 2-(p-biphenylyl)isopropyloxycarbonyl are very labile and can be cleaved under mild acid conditions. Other protecting groups, such as t-butyloxycarbonyl (BOC), t-amyloxycarbonyl, adamantyl-oxycarbonyl, and p-methoxybenzyloxycarbonyl, are less labile and require moderately strong acids, such as trifluoroacetic, hydrochloric, or boron trifluoride in acetic acid, for their removal. Still other protecting groups, such as benzyloxy-carbonyl (CBZ or Z), halobenzyloxycarbonyl, p-nitrobenzyloxycarbonyl cycloalkyloxycarbonyl, and isopropyloxycarbonyl, are even less labile and require stronger acids, such as hydrogen fluoride, hydrogen bromide, or boron trifluoroacetate in trifluoroacetic acid, for their removal. Among the classes of useful amino acid protecting groups are included:

(1) for an α-amino group, (a) aromatic urethane-type protecting groups, such as fluorenylmethyloxycarbonyl (FMOC) CBZ, and substituted CBZ, such as, e.g., p-chlorobenzyloxycarbonyl, p-6-nitrobenzyloxycarbonyl, p-bromobenzyloxycarbonyl, and p-methoxybenzyloxycarbonyl, o-chlorobenzyloxycarbonyl, 2,4-dichlorobenzyloxycarbonyl, 2,6-dichlorobenzyloxycarbonyl, and the like; (b) aliphatic urethane-type protecting groups, such as BOC, t-amyloxycarbonyl, isopropyloxycarbonyl, 2-(p-biphenylyl)-isopropyloxycarbonyl, allyloxycarbonyl and the like; (c) cycloalkyl urethane-type protecting groups, such as cyclopentyloxycarbonyl, adamantyloxycarbonyl, and cyclohexyloxycarbonyl; and d) allyloxycarbonyl. The preferred α-amino protecting groups are BOC or FMOC.

(2) for the side chain amino group present in Lys, protection may be by any of the groups mentioned above in (1) such as BOC, p-chlorobenzyloxycarbonyl, etc.

(3) for the guanidino group of Arg, protection may be by nitro, tosyl, CBZ, adamantyloxycarbonyl, 2,2,5,7,8-pentamethylchroman-6-sulfonyl, 2,3,6-trimethyl-4-methoxyphenylsulfonyl, or BOC.

(4) for the hydroxyl group of Ser, Thr, or Tyr, protection may be, for example, by C1–C4 alkyl, such as t-butyl; benzyl (BZL); or substituted BZL, such as p-methoxybenzyl, p-nitrobenzyl, p-chlorobenzyl, o-chlorobenzyl, and 2,6-dichlorobenzyl.

(5) for the carboxyl group of Asp or Glu, protection may be, for example, by esterification using groups such as BZL, t-butyl, cyclohexyl, cyclopentyl, and the like.

(6) for the imidazole nitrogen of His, the tosyl moiety is suitably employed.

(7) for the phenolic hydroxyl group of Tyr, a protecting group such as tetrahydropyranyl, tert-butyl, trityl, BZL, chlorobenzyl, 4-bromobenzyl, or 2,6-dichlorobenzyl is suitably employed. The preferred protecting group is 2,6-dichlorobenzyl.

(8) for the side-chain amino group of Asn or Gln, xanthyl (Xan) is preferably employed.

(9) for Met, the amino acid is preferably left unprotected.

(10) for the thio group of Cys, p-methoxybenzyl is typically employed.

The C-terminal amino acid, e.g., Lys, is protected at the N-amino position by an appropriately-selected protecting group, in the case of Lys, BOC. The BOC-Lys-OH can be first coupled to the benzyhydrylamine or chloromethylated resin according to the procedure set forth in Horiki et al., *Chemistry Letters*, 165–168 (1978) or using isopropylcarbodiimide at about 25° C. for 2 hours with stirring. Following the coupling of the BOC-protected amino acid to the resin support, the α-amino protecting group is removed, as by using trifluoroacetic acid (TFA) in methylene chloride or TFA alone. The deprotection is carried out at a temperature between about 0° C. and room temperature. Other standard cleaving reagents, such as HCl in dioxane, and conditions for removal of specific α-amino protecting groups are described in the literature.

After removal of the α-amino protecting group, the remaining α-amino and side-chain protected amino acids are coupled stepwise within the desired order. As an alternative to adding each amino acid separately in the synthesis, some may be coupled to one another prior to addition to the solid-phase synthesizer. The selection of an appropriate coupling reagent is within the skill of the art. Particularly suitable as a coupling reagent is N,N'-dicyclohexyl carbodiimide or diisopropylcarbodiimide.

Each protected amino acid or amino acid sequence is introduced into the solid-phase reactor in excess, and the oupling is suitably carried out in a medium of dimethylformamide (DMF) or $CH_2Cl_2$ or mixtures thereof. If incomplete coupling occurs, the coupling procedure is repeated before removal of the N-amino protecting group prior to the coupling of the next amino acid. The success of the coupling reaction at each stage of the synthesis may be monitored. A preferred method of monitoring the synthesis is by the ninhydrin reaction, as described by Kaiser et al., *Anal. Biochem*, 34: 595 (1970). The coupling reactions can be performed automatically using well-known methods, for example, a BIOSEARCH 9500™ peptide synthesizer.

Upon completion of the desired peptide sequence, the protected peptide must be cleaved from the resin support, and all protecting groups must be removed. The cleavage reaction and removal of the protecting groups is suitably accomplished simultaneously or stepwise. When the resin support is a chloro-methylated polystyrene resin, the bond anchoring the peptide to the resin is an ester linkage formed between the free carboxyl group of the C-terminal residue and one of the many chloromethyl groups present on the resin matrix. It will be appreciated that the anchoring bond can be cleaved by reagents that are known to be capable of breaking an ester linkage and of penetrating the resin matrix.

One especially convenient method is by treatment with liquid anhydrous hydrogen fluoride. This reagent not only will cleave the peptide from the resin but also will remove all protecting groups. Hence, use of this reagent will directly afford the fully deprotected peptide. When the chloromethylated resin is used, hydrogen fluoride treatment results in the formation of the free peptide acids. When the benzhydrylamine resin is used, hydrogen fluoride treatment results directly in the free peptide amines. Reaction with hydrogen fluoride in the presence of anisole and dimethylsulfide at 0° C for one hour will simultaneously remove the side-chain protecting groups and release the peptide from the resin.

When it is desired to cleave the peptide without removing protecting groups, the protected peptide-resin can undergo methanolysis to yield the protected peptide in which the C-terminal carboxyl group is methylated. The methyl ester is then hydrolyzed under mild alkaline conditions to give the free C-terminal carboxyl group. The protecting groups on the peptide chain then are removed by treatment with a strong acid, such as liquid hydrogen fluoride. A particularly useful technique for methanolysis is that of Moore et al., *Peptides. Proc. Fifth Amer. Pest. Symp.*, M. Goodman and J. Meienhofer, Eds., (John Wiley, N.Y., 1977), p. 518–521, in which the protected peptide-resin is treated with methanol and potassium cyanide in the presence of crown ether.

Another method for cleaving the protected peptide from the resin when the chloromethylated resin is employed is by ammonolysis or by treatment with hydrazine. If desired, the resulting C-terminal amide or hydrazide can be hydrolyzed to the free C-terminal carboxyl moiety, and the protecting groups can be removed conventionally.

It will also be recognized that the protecting group present on the N-terminal α-amino group may be removed preferentially either before or after the protected peptide is cleaved from the support.

Purification of the polypeptides of the invention is typically achieved using conventional procedures such as preparative high-pressure liquid chromatography (HPLC) (including reversed-phase HPLC) or other known chromatographic techniques such as gel permeation, ion exchange, partition chromatography, affinity chromatography (including monoclonal antibody columns), or countercurrent distribution.

The peptides of this invention may be stabilized by polymerization. This may be accomplished by crosslinking monomer chains with polyfunctional crosslinking agents, either directly or indirectly, through multi-functional polymers, ordinarily, two substantially identical polypeptides are crosslinked at their C- or N-termini using a bifunctional crosslinking agent. The agent is used to crosslink the terminal amino and/or carboxyl groups. Generally, both terminal carboxyl groups or both terminal amino groups are crosslinked to one another, although by selection of the appropriate crosslinking agent the α-amino group of one polypeptide is crosslinked to the terminal carboxyl group of the other polypeptide. Preferably, the polypeptides are substituted at their C-termini with cysteine. Under conditions well known in the art a disulfide bond can be formed between the terminal cysteines, thereby crosslinking the polypeptide chains. For example, disulfide bridges are conveniently formed by metal-catalyzed oxidation of the free cysteines or by nucleophilic substitution of a suitably modified cysteine residue. Selection of the crosslinking agent will depend upon the identities of the reactive side-chains of the amino acids present in the polypeptides. For example, disulfide crosslinking would not be preferred if cysteine was present in the polypeptide at additional sites other than the C-terminus. Also within the scope hereof are peptides crosslinked with methylene bridges.

Suitable crosslinking sites on the peptides, aside from the N-terminal amino and C-terminal carboxyl groups, include epsilon amino groups found on lysine residues, as well as amino, imino, carboxyl, sulfhydryl and hydroxyl groups located on the side-chains of internal residues of the peptides or residues introduced into flanking sequences. Crosslinking through externally added crosslinking agents is suitably achieved, e.g., using any of a number of reagents familiar to those skilled in the art, for example, via carbodiimide treatment of the polypeptide. Other examples of suitable multi-functional (ordinarily bifunctional) crosslinking agents are found in the literature.

The peptides of this invention also may be conformationally stabilized by cyclization. The peptides ordinarily are cyclized by covalently bonding the N- and C-terminal domains of one peptide to the corresponding domain of another peptide of this invention so as to form cyclo-oligomers containing two or more iterated peptide sequences, each internal peptide having substantially the same sequence. Further, cyclized peptides (whether cyclo-oligomers or cyclo-monomers) are crosslinked to form 1–3 cyclic structures having from 2 to 6 peptides comprised therein. The peptides preferably are not covalently bonded through α-amino and main-chain carboxyl groups (head to tail), but rather are crosslinked through the side-chains of residues located in the N- and C-terminal domains. The linking sites thus generally will be between the side-chains of the residues.

Many suitable methods per se are known for preparing mono- or poly-cyclized peptides as contemplated herein. Lys/Asp cyclization has been accomplished using Na-Boc-amino acids on solid-phase support with Fmoc/9-fluorenylmethyl (OFm) side-chain protection for Lys/Asp; the process is completed by piperidine treatment followed by cyclization. Glu and Lys side-chains also have been crosslinked in preparing cyclic or bicyclic peptides: the peptide is synthesized by solid-phase chemistry on a p-methylbenzhydrylamine resin. The peptide is cleaved from the resin and deprotected. The cyclic peptide is formed using diphenylphosphorylazide in diluted methylformamide. For an alternative procedure, see Schiller et al., *Pentide Protein Res.*, 25: 171–177 (1985). See also U.S. Pat. No. 4,547,489.

Disulfide crosslinked or cyclized peptides are generated by conventional methods. The method of Pelton et al. (*J. Med. Chem.*, 29: 2370–2375 (1986)) is suitable, except that a greater proportion of cyclo-oligomers are produced by conducting the reaction in more concentrated solutions than the dilute reaction mixture described by Pelton et al., supra, for the production of cyclo-monomers. The same chemistry is useful for synthesis of dimers or cyclo-oligomers or cyclo-monomers. Also useful are thiomethylene bridges. Lebl and Hruby, *Tetrahedron Letters*, 25: 2067–2068 (1984). See also Cody et al., *J. Med. Chem.*, 28: 583 (1985).

The desired cyclic or polymeric peptides are purified by gel filtration followed by reversed-phase HPLC or other conventional procedures. The peptides are sterile filtered and formulated into conventional pharmacologically acceptable vehicles.

The starting materials required for the processes described herein are known in the literature or can be prepared using known methods and known starting materials.

If in the peptides being created carbon atoms bonded to four nonidentical substituents are asymmetric, then the compounds may exist as diastereoisomers, enantiomers, or mixtures thereof. The syntheses described above may employ racemates, enantiomers, or diastereomers as starting materials or intermediates. Diastereomeric products resulting from such syntheses may be separated by chromatographic or crystallization methods. Likewise, enantiomeric product mixtures may be separated using the same techniques or by other methods known in the art. Each of the asymmetric carbon atoms, when present, may be in one of two configurations (R or S), and both are within the scope of the present invention.

The peptides described in this invention may be isolated as the free acid or base or converted to salts of various inorganic and organic acids and bases. Such salts are within the scope of this invention. Examples of such salts include ammonium, metal salts like sodium, potassium, calcium, and magnesium; salts with organic bases like dicyclohexylamine, N-methyl-D-glucamine and the like; and salts with amino acids like arginine or lysine. Salts with inorganic and organic acids may be likewise prepared, for example, using hydrochloric, hydrobromic, sulfuric, phosphoric, trifluoroacetic, methanesulfonic, malic, maleic, fumaric acid, and the like. Non-toxic and physiologically-compatible salts are particularly useful, although other less desirable salts may have use in the processes of isolation and purification.

A number of methods are useful for the preparation of the salts described above and are known to those skilled in the art. Examples include reaction of the free acid or free base form of the peptide with one or more molar equivalents of the desired acid or base in a solvent or solvent mixture in which the salt is insoluble; or in a solvent like water after which the solvent is removed by evaporation, distillation or freeze drying. Alternatively, the free acid or base form of the product may be passed over an ion-exchange resin to form the desired salt or one salt form of the product may be converted to another using the same general process.

Certain specific schemes appropriate for chemical synthesis of the peptides herein are shown in WO 96/15148 published May 23, 1996 and WO 98/20036 published May 14, 1998 on locked helix peptides, which are self-connected peptides but do not contain disulfide bonds. Specifically, in another aspect the invention provides a method for removing elements of α-helical secondary structure from the context of a IGFBP-1 displacer peptide herein without losing the well-defined structure found within the protein's α-helix. This method may be used to stabilize the conformational structure of a peptide herein. The present methods can be employed to lock in place one (or more) α-helical determinant(s) of interest in a bp1-01 derivative pep tide such that the peptide retains an α-helical conformation in environments or conditions that would destabilize or deteriorate the α-helical secondary structure of an unconstrained peptide species.

In this vein, as noted above, the invention provides a constrained helical peptide comprising a sequence of nine amino acid residues having a first terminal residue and a second terminal residue, wherein said residues flank an internal sequence of seven amino acids and have side-chains covalently bonded to each other to form a locking moiety and thereby constrain the peptide.

While the locking moiety can be any structure that constrains the internal sequence to a helical peptide form and does not interfere with the active face of the constrained peptide, the preferred peptides use the locking chemistry taught herein. Peptides of the invention can have the first and second terminal residues with side-chains containing an amide bond-forming substituent that are linked to each other via an amide bond to form a constrained helical peptide. The side-chain amide bond-forming substituent of the first terminal residue and the side-chain amide bond-forming substituent of the second terminal residue may be independently selected from the group consisting of an amino substituent and a carboxy substituent. Preferably, the side-chain amide bond-forming substituent of the first terminal residue is a carboxy substituent, the side-chain amide bond-forming substituent of the second terminal residue is a carboxy substituent, and the difunctional linker is a diamine wherein the first and second functional groups are amino groups. In preferred form the first terminal residue and the second terminal residue are independently selected from the group consisting of Asp and Glu, more preferred the first terminal residue and the second terminal residue are both Glu. The first terminal residue can have a D-thio-lysine side-chain and the second terminal residue a L-thio-lysine that are linked to each other resulting in a disulfide-bonded locking moiety, and hence a constrained helical peptide.

More preferably, the peptide of the invention is selected from the group consisting of constrained helical peptides of each possible sequence having any one or any combination of amino acid substitutions indicated in the constrained helical peptide wherein the internal sequence is $Xaa_{(7)}$LeuAla$Xaa_{(10)}Xaa_{(11)}Xaa_{(12)}Xaa_{(13)}$ (SEQ ID NO:31), wherein $Xaa_{(7)}$, $Xaa_{(11)}$, $Xaa_{(12)}$, and $Xaa_{(13)}$ are independently Nal(1), His, Phe, Trp, Tyr, Pro, Gln, or Met, and $Xaa_{(10)}$ is any amino acid.

In yet another embodiment of the invention, peptides comprising the sequences described herein can be synthesized with additional chemical groups present at their amino and/or carboxy termini, such that, for example, the stability, bioavailability, and/or inhibitory activity of the peptides is enhanced. For example, hydrophobic groups such as carbobenzoxyl, dansyl, or t-butyloxycarbonyl groups, may be added to the amino termini. An acetyl group or a 9-fluorenylmethoxy-carbonyl group may be placed at the amino termini. A hydrophobic group, t-butyloxycarbonyl, or an amido group may be added to carboxy termini. Furthermore, the peptides of the invention can be synthesized such that their steric configuration is altered. For example, the D-isomer of one or more of the amino acid residues of the peptide can be used, rather than the usual L-isomer. The peptides can contain at least one bond linking adjacent amino acids that is a non-peptide bond, and is preferably not helix breaking. Non-peptide bonds for use in flanking sequences include an imino, ester, hydrazine, semicarbazide, oxime, or azo bond. Still further, at least one of the amino acid residues of the peptides of the invention can be substituted by one of the well-known non-naturally-occurring amino acid residues that is preferably not helix breaking. Most preferably, the non-natural amino acid or non-amide bond linking adjacent amino acids, when present, are present outside of the internal sequence, and are, more preferably, not helix breaking. Still further, at least one of the amino acid residues of the peptides of the invention can be substituted by one of the well-known non-naturally-occurring amino acid residues. Alterations such as these can serve to increase the stability, bioavailability, immunogenicity, and/or inhibitory action of the peptides of the invention.

According to the present method, an element of α-helical structure is removed from its context in a native protein by constructing a peptide with an amino acid sequence spanning the α-helical secondary structure of interest in the native protein, and constraining the short peptide into an α-helical conformation that mimics the α-helical secondary structure of interest. The present methods enable the practitioner to lock into a helical. conformation any peptide that is seven amino acids in length by placing an amino acid with a side-chain amide bond-forming substituent at the N-terminus of the peptide and placing another amino acid with a side-chain amide bond-forming substituent at the C-terminus of the peptide, and then joining the side-chain amide bond-forming substituents of the N-terminal and C-terminal residues to form a cyclized structure that mimics the conformation of an α-helix. The present methods also enable the practitioner to lock into a helical conformation any sequence of seven amino acid residues in a larger peptide by importing two residues with side-chain amide bond-forming substituents into the N-terminal amino acid position and the C-terminal position amino acid position flanking the sequence (of seven amino acid residues) of interest within a larger peptide, and then joining the side-chain amide bond-forming substituents of the N-terminal and C-terminal flanking residues to form a cyclized structure that mimics the conformation of an α-helix.

There are at least two general methods for constructing the constrained helix peptides of the invention: (1) synthesis of a linear peptide comprising a pair of residues that flank an amino acid sequence that is seven residues in length, wherein the two flanking residues are independently selected from the group consisting of amino acid residues with side-chain amide bond-forming substituents, followed by bridging the side-chain amide bond-forming substituents of the flanking residues with a difunctional linker to cyclize the peptide; and (2) synthesis of a linear peptide comprising a pair of residues that flank an amino acid sequence that is seven residues in length, wherein the two flanking residues are independently selected from the group consisting of amino acid residues with side-chain amide bond-forming substituents, and wherein one of the flanking residues is added to the peptide chain carrying a difunctional linker such that one functional group of the linker is coupled to the residue's side-chain amide bond-forming substituent, followed by coupling of the linker's free functional group to the side-chain amide bond-forming substituent on the other flanking residue to cyclize the peptide.

Any amino acid that has a side-chain containing a substituent capable of forming an amide bond can be used as a flanking residue herein. Suitable flanking amino acid residues include amino acids with side-chains carrying a free carboxy group, such as aminopropanedioic acid, Asp, Glu, 2-aminohexanedioic acid, 2-aminoheptanedioic acid, 2-aminooctanedioic acid, 2-aminononanedioic acid, and amino acids with side-chains carrying a free amino group, such as 2,3-diaminopropanoic acid (2,3-diaminopropionic acid), 2,4-diaminobutanoic acid (2,4-diaminobutyric acid), 2,5-diaminopentanoic acid, 2,7-diaminoheptanoic acid, 2,8-diaminooctanoic acid, 2,9-diaminononanoic acid, and Lys. It is preferably Asp and/or Glu, most preferably Glu. In a most preferred aspect, the Glu residues are joined by forming amides with 1,5-diaminopentane.

In some embodiments, the desired peptide contains an additional amino acid or amino acids extending from the C-terminal flanking residue and/or N-terminal flanking residue.

Once the desired peptide sequence is selected, chemical synthesis can be employed to construct the constrained helix peptide of the invention. This can be accomplished by modifying any one of a number of methodologies well known in the art (see Kelley, R. F. & Winkler, M. E. in *Genetic Engineering Principles and Methods*, Setlow, J. K, ed., Plenum Press, N.Y., vol. 12, pp 1–19 (1990), Stewart, J. M. Young, J. D., *Solid Phase Pentide Synthesis*, Pierce Chemical Co., Rockford, Ill. (1984); see also U.S. Pat. Nos. 4,105,603; 3,972,859;3,842,067; and 3,862,925) to produce the desired peptide.

In addition, the methods of the invention can be practiced in conjunction with solution phase peptide synthesis, for example, the solution phase peptide synthesis methods described in *Principles of Pentide Synthesis*, 2d ed, M. Bodanszky, Springer-Verlag (1993) or in *The Practice of Peptide Synthesis*, 2d ed, M. Bodanszky and A. Bodanszky, Springer-Verlag (1994). It will be appreciated that solution phase peptide synthesis methods can be easily modified to incorporate the desired flanking residues, with or without orthogonally-protected side-chain amide bond-forming substituents, into the peptide chain of interest, using procedures similar to those used in the solid phase peptide synthesis methods described herein. It will be further appreciated that all references to peptide synthesis herein encompass both solid phase and solution (or liquid) phase peptide synthesis methods, unless otherwise indicated.

After the desired amino acid sequence has been completed, the linear peptide is cyclized in order to constrain the peptide in a helical conformation. Any method of bridging the side-chain amide bond-forming substituents of the flanking residues with a difunctional linker is suitable for producing the constrained helical peptides of the invention. See WO 98/20036, supra, for details on cyclization and cleavage of the peptide from the solid support, as well as for details on synthesis of linear peptides without a difunctional linker-coupled flanking amino acid and linear peptides with a difunctional linker-coupled flanking amino acid.

The peptides of this invention are shown to inhibit the interaction of an IGF with one or more of its binding proteins and thereby agonize IGF action. It is known to those skilled in the art that there are many uses for IGFs. Therefore, administration of the peptides of this invention for purposes of agonizing an IGF action can have the same effects or uses as administration of an exogenous IGF itself. These uses of IGF include the following, which may be additional to or the same as the disorders as defined above: increasing whole body, bone, and muscle growth rate in normal and hypopituitary animals; protection of body weight and nitrogen loss during catabolic states (such as fasting, nitrogen restriction, elevated corticosteroid levels, and/or diabetes); kidney regeneration; treating peripheral and central nervous system (CNS) degenerative disorders and promoting neuroprotection or repair following CNS damage or injury; treating hypoxia; promotion of wound healing; cardiac regeneration; reversal of cancer cachexia; inhibition of angiogenesis; regeneration of the gastrointestinal tract; stimulation of mammary function; counteracting IGF-I-dependent actions of GH such as metabolic stress, age-related decreases in GH activity, and adult GH deficiency; treating maturity-onset diabetes; and/or treating a specific IGF deficiency.

Additional and specific disorders for which the peptides herein are useful include growth disorders such as GH-resistant short stature, GH-insensitivity syndrome, osteoporosis, and catabolic states; disorders where treatment requires regeneration of tissues or cells, for example, peripheral nerves and supporting cells, central nervous system cells including nerves and glia, and other cells such as oligodendrocytes, muscle, skin, and bone; heart disorders, e.g., heart ischemia, cardiac myopathy, and congestive heart disorders; hyperglycemic disorders such as insulin-dependent and non-insulin-dependent diabetes mellitus and extreme insulin resistance; and renal disorders such as renal failure. These also include stimulation of an anabolic response in elderly humans, prevention of catabolic side effects of glucocorticoids, treatment of osteoporosis, stimulation of the immune system, reduction of obesity, acceleration of wound healing, acceleration of bond fracture repair, treatment of growth retardation, treatment of renal failure or insufficiency resulting in growth retardation, treatment of physiological short stature, including growth-hormone-deficient children, treating short stature associated with chronic illness, treatment of obesity and growth retardation associated with obesity, treatment of growth retardation associated with Prader-Willi syndrome and Turner's syndrome, acceleration of the recovery and reduction in the hospitalization of burn patients, treatment of interuterine growth retardation, skeletal dysplasia, hypercortisolism, and Cushings syndrome, induction of pulsatile growth hormone release, replacement of growth hormone in stressed patients, treatment of osteochondrodysplasias, Noonans syndrome, schizophrenia, depression, peripheral neuropathy, ALS, depression, Alzheimer's disease, diseases of demyelination, multiple sclerosis, and delayed wound healing, stimulation of the immune system, treatment of physcosocia depravation, treatment of pulmonary dysfunction and ventilator dependency, attenuation of protein catabolic response after a major operation, reduction of cachexia and protein loss due to chronic illness such as cancer or AIDS, treatment of hyperinsulinemia including Type II and Type I diabetes, adjuvant treatment for ovulation induction, stimulation of thymic development and prevention of the age-related decline of thymic function, treatment of immunosuppressed patients, treatment of bone marrow transplanted patients, improvement in muscle strength, mobility, diseases of muscle function, muscular dystrophy, maintenance of skin thickness, and metabolic homeostasis, enhancement of renal function and homeostasis including acute and chronic renal failure, stimulation of osteoblasts, bone remodeling, and cartilage growth, stimulation of the immune system, and growth promotion in livestock. Various IGF-I uses are found, for example, in WO 94/04569; WO 96/33216; and Bondy, *Ann Intern. Med.*, 120: 593–601 (1994). All these are included in the definition of "disorder."

In one example, the peptides can be administered to commercially-important mammals such as swine, cattle, sheep, and the like to accelerate and increase their rate and extent of growth and the efficiency of their conversion of feed into body tissue. The peptides can be administered in vivo to adults and children to stimulate IGF action.

The peptides of this invention may be administered to the mammal by any suitable technique, including oral, parenteral (e.g., intramuscular, intraperitoneal, intravenous, or subcutaneous injection or infusion, or implant), nasal, pulmonary, vaginal, rectal, sublingual, or topical routes of administration, and can be formulated in dosage forms appropriate for each route of administration. The specific route of administration will depend, e.g., on the medical history of the patient, including any perceived or anticipated side effects using the peptide, the type of peptide being administered, and the particular disorder to be corrected. Most preferably, the administration is orally or by continuous infusion (using, e.g., slow-release devices or minipumps such as osmotic pumps or skin patches), or by injection (using, e.g., intravenous or subcutaneous means).

The peptide to be used in the therapy will be formulated and dosed in a fashion consistent with good medical practice, taking into account the clinical condition of the individual patient (especially the side effects of treatment with the peptide), the site of delivery, the method of administration, the scheduling of administration, and other factors known to practitioners. The "effective amounts" of the peptide for purposes herein are thus determined by such considerations and must be amounts that result in bioavailability of the drugs to the mammal and the desired effect.

One preferred administration is a chronic administration of about two times per day for 4–8 weeks to reproduce the effects of IGF-I. Although injection is preferred, chronic infusion may also be employed using an infusion device for continuous subcutaneous (SC) infusions. A small peptide may be administered orally. An intravenous bag solution may also be employed, as well as pulmonary administration, as described below. The key factor in selecting an appropriate dose specifically for diabetes is the result obtained, asmeasured by decreases in blood glucose so as to approximate the normal range, or by other criteria for measuring treatment of diabetes as are deemed appropriate by the medical practitioner.

As a general proposition, the total pharmaceutically effective amount of the IGF agonist peptide administered parenterally per dose will be in a range that can be measured by a dose-response curve. For example, IGFs bound to IGFBPs or in the blood can be measured in body fluids of the mammal to be treated to determine the dosing. Alternatively, one can administer increasing amounts of the IGF agonist peptide to the patient and check the serum levels of the patient for IGF-I and IGF-II. The amount of IGF agonist to be employed can be calculated on a molar basis based on these serum levels of IGF-I and IGF-II. See the examples below on displacement of IGF-I tracer from IGFBPs present in human serum.

Specifically, one method for determining appropriate dosing of the peptide entails measuring IGF levels in a biological fluid such as a body or blood fluid. Measuring such levels can be done by any means, including RIA and ELISA. After measuring IGF levels, the fluid is contacted with a peptide herein using single or multiple doses. After this contacting step, the IGF levels are re-measured in the fluid. If the fluid IGF levels have fallen by an amount sufficient to produce the desired efficacy for which the molecule is to be administered, then the dose of the molecule can be adjusted to produce maximal efficacy. This method may be carried out in vitro or in vivo. Preferably, this method is carried out in vivo, i.e., after the fluid is extracted from a mammal and the IGF levels measured, the peptide herein is administered to the mammal using single or multiple doses (that is, the contacting step is achieved by administration to a mammal) and then the IGF levels are remeasured from fluid extracted from the mammal.

Another method for determining the amount of a particular IGFBP or the amount of the peptide herein bound to a particular IGFBP in a biological fluid so that dosing of the peptide can be adjusted appropriately involves:

(a) contacting the fluid with 1) a first antibody attached to a solid-phase carrier, wherein the first antibody is specific for epitopes on the IGFBP such that in the presence of antibody the IGF binding sites remain available on the IGFBP for binding to the peptide, thereby forming a complex between the first antibody and the IGFBP; and 2) the peptide for a period of time sufficient to saturate all available IGF binding sites on the IGFBP, thereby forming a saturated complex;

(b) contacting the saturated complex with a detectably-labeled second antibody which is specific for epitopes on the peptide which are available for binding when the peptide is bound to the IGFBP; and (c) quantitatively analyzing the amount of the labeled second antibody bound as a measure of the IGFBP in the biological fluid, and therefore as a measure of the amount of the peptide bound. This technique can be expanded to include a diagnostic use whereby the peptide is administered to a mammal to displace an IGF from a specific IGFBP for which the peptide has affinity, such as IGFBP-1 or IGFBP-3, and measuring the amount that is displaced.

The quantitative technique mentioned above using antibodies, called the ligand-mediated immunofunctional method (LIFA), is described for determining the amount of IGFBP by contact with IGF in U.S. Pat. No. 5,593,844, and for determining the amount of GHBP by contact with GH in U.S. Pat. No. 5,210,017. These references describe antibodies and other materials and conditions that can be used in the assay.

Another method for determining dosing is to use antibodies to the IGF agonist or another detection method for the IGF agonist in the LIFA format. This would allow detection of endogenous or exogenous IGFs bound to IGFBP and the amount of IGF agonist bound to the IGFBP.

Another method for determining dosing would be to measure the level of "free" or active IGF in blood. For some uses the level of "free" IGF would be a suitable marker of efficacy and effective doses or dosing.

For example, one method is described for detecting endogenous or exogenous IGF bound to an IGF binding protein or the amount of a peptide herein or detecting the level of unbound IGF in a biological fluid. This method comprises:

(a) contacting the fluid with 1) a means for detecting the peptide that is specific for the peptide (such as a first antibody specific for epitopes on the peptide) attached to a solid-phase carrier, such that in the presence of the peptide the IGF binding sites remain available on the peptide for binding to the IGF binding protein, thereby forming a complex between the means and the IGF binding protein; and 2) the peptide for a period of time sufficient to saturate all available IGF binding sites on the IGF binding protein, thereby forming a saturated complex;

(b) contacting the saturated complex with a detectably-labeled second means that is specific for the IGF binding protein (such as a second antibody specific for epitopes on the IGFBP) that are available for binding when the peptide is bound to the IGF binding protein; and (c) quantitatively analyzing the amount of the labeled means bound as a measure of the IGFBP in the biological fluid, and therefore as a measure of the amount of bound peptide and IGF binding protein, bound IGF and IGF binding protein, or active IGF present in the fluid.

Given the above methods for determining dosages, and assuming dosing shares at least some of the characteristics demonstrated in Example 11 of WO 98/45427, supra, for IGF-I, in general, the amount of IGF agonist peptide that may be employed can be estimated. An orally active small IGF agonist would have a molecular weight of approximately 500 daltons, compared to 7500 daltons for IGF-I and IGF-II. Assuming the IGF agonist is 16-fold less able to bind to IGFBPs than IGF-I or IGF-II, then equal weights of IGF-I or IGF-II and these molecules could be equally effective, so that doses from about 10 µg/kg/day to 200 µg/kg/day might be used, based on kg of patient body weight, although, as noted above, this will be subject to a great deal of therapeutic discretion.

A further method is provided to estimate the distribution of IGFs on specific IGFBPs, e.g., on IGFBP-1 or IGFBP-3 using the LIFA format.

The peptide is suitably administered by a sustained-release system. Suitable examples of sustained-release compositions include semi-permeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (Sidman et al., *Biopolymers*, 22, 547–556 (1983)), poly(2-hydroxyethyl methacrylate) (Langer et al., *J. Biomed. Mater. Res.*, 15: 167–277 (1981), and Langer, *Chem. Tech.*, 12: 98–105 (1982)), ethylene vinyl acetate (Langer et al., supra) or poly-D-(−)-3-hydroxybutyric acid (EP 133,988). Sustained-release compositions also include a liposomally-entrapped peptide. Liposomes containing the peptide are prepared by methods known per se: DE 3,218,121; Epstein et al., *Proc. Natl. Acad. Sci. U.S.A.*, 82: 3688–3692 (1985); Hwang et al., *Proc. Natl. Acad. Sci. U.S.A.*, 77: 4030–4034 (1980); EP 52,322; EP 36,676; EP 88,046; EP 143,949; EP 142,641; Japanese Pat. Appln. 83-118008; U.S. Pat. Nos. 4,485,045 and 4,544,545; and EP 102,324. Ordinarily, the liposomes are of the small (from or about 200 to 800 Angstroms) unilamellar type in which the lipid content is greater than about 30 mol. percent cholesterol, the selected proportion being adjusted for the most efficacious therapy.

Peptides derivatized with polyethylene glycol (PEG) having a longer life can also be employed, based on, e.g., the conjugate technology described in WO 95/32003 published Nov. 30, 1995.

For parenteral administration, in one embodiment, the peptide herein is formulated generally by mixing it at the desired degree of purity, in a unit dosage injectable form (solution, suspension, or emulsion), with a pharmaceutically, or parenterally, acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the peptide uniformly and intimately with liquid carriers or finely-divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, a buffered solution, and dextrose solution. Non-aqueous vehicles such as fixed oils and ethyl oleate are also useful herein.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; glycine; amino acids such as glutamic acid, aspartic acid, histidine, or arginine; monosaccharides, disaccharides, and other carbohydrates including cellulose or its derivatives, glucose, mannose, trehalose, or dextrins; chelating agents such as EDTA; sugar alcohols such as mannitol or sorbitol; counter-ions such as sodium; non-ionic surfactants such as polysorbates, poloxamers, or polyethylene glycol (PEG); and/or neutral salts, e.g., NaCl, KCl, $MgCl_2$, $CaCl_2$, etc. The peptide is typically formulated in such vehicles at a pH of from about 4.5 to 8. It will be understood that use of certain of the foregoing excipients, carriers, or stabilizers will result in the formation of salts of the peptide. The final preparation may be a stable liquid or lyophilized solid.

The peptide to be used for therapeutic administration must be sterile. Sterility is readily accomplished by filtration through sterile filtration membranes (e.g., 0.2 micron membranes). Therapeutic compositions generally are placed into a container having a sterile access port, for example, an intravenous solution bag or vial having a stopper pierceable by a hypodermic injection needle.

The peptide ordinarily will be stored in unit or multi-dose containers, for example, sealed ampules or vials, as an aqueous solution or as a lyophilized formulation for reconstitution. As an example of a lyophilized formulation, 10-mL vials are filled with, 5 mL of sterile-filtered 1% (w/v) aqueous solution of peptide, and the resulting mixture is lyophilized. The infusion solution is prepared by reconstituting the lyophilized peptide using bacteriostatic Water-for-Injection.

A preferred route of administration of the present invention is in the aerosol or inhaled form. The peptides of the present invention, combined with a dispersing agent, or dispersant, can be administered in an aerosol formulation as a dry powder or in a solution or suspension with a diluent.

Suitable dispersing agents are well known in the art, and include but are not limited to surfactants and the like. For example, surfactants that are generally used in the art to reduce surface-induced aggregation of the peptide caused by atomization of the solution forming the liquid aerosol may be used. Non-limiting examples are surfactants such as polyoxyethylene fatty acid esters and alcohols and polyoxyethylene sorbitan fatty acid esters. Amounts of surfactants used will vary, being generally within the range of about 0.001 and 4% by weight of the formulation. In a specific aspect, the surfactant is polyoxyethylene sorbitan monooleate or sorbitan trioleate. Suitable surfactants are well known in the art, and can be selected on the basis of desired properties, depending on the specific formulation, concentration of the peptide, diluent (in a liquid formulation), or form of powder (in a dry powder formulation), etc.

Moreover, depending on the choice of the peptide, the desired therapeutic effect, the quality of the lung tissue (e.g., diseased or healthy lungs), and numerous other factors, the liquid or dry formulations can comprise additional components, as discussed further below.

The liquid aerosol formulations generally contain the peptide and a dispersing agent in a physiologically-acceptable diluent. The dry powder aerosol formulations of the present invention consist of a finely divided solid form of the peptide and a dispersing agent. With either the liquid or dry powder aerosol formulation, the formulation must be aerosolized. That is, it must be broken down into liquid or solid particles to ensure that the aerosolized dose actually reaches the alveoli. In general, the mass median dynamic diameter will be about 5 micrometers or less in order to ensure that the drug particles reach the lung alveoli (Wearley, *Crit. Rev. in Ther. Drug Carrier Systems*, 8: 333 (1991)). Aerosol particles are the liquid or solid particles suitable for pulmonary administration, i.e., that will reach the alveoli. Other considerations such as construction of the delivery device, additional components in the formulation, and particle characteristics are important. These aspects of pulmonary administration of a drug are well known in the art, and manipulation of formulations, aerosolization means, and construction of a delivery device require at most routine experimentation by one of ordinary skill in the art.

With regard to construction of the delivery device, any form of aerosolization known in the art, including but not limited to nebulization, atomization, or pump aerosolization of a liquid formulation, and aerosolization of a dry powder formulation, can be used in the practice of the invention. A delivery device that is uniquely designed for administration of solid formulations is envisioned. Often, the aerosolization of a liquid or a dry powder formulation will require a propellent. The propellant may be any propellant generally used in the art. Specific nonlimiting examples of such useful propellants include a chlorofluorocarbon, a hydrofluorocarbon, a hydrochlorofluorocarbon, or a hydrocarbon, including trifluoromethane, dichlorodifluoromethane, dichlorotetrafluoroethanol, and 1,1,1,2-tetrafluoroethane, or combinations thereof.

In a preferred aspect of the invention, the device for aerosolization is a metered dose inhaler. A metered dose inhaler provides a specific dosage when administered, rather than a variable dose depending on administration. Such a metered dose inhaler can be used with either a liquid or a dry powder aerosol formulation. Metered dose inhalers are well known in the art.

Once the peptide reaches the lung, a number of formulation-dependent factors affect the drug absorption. It will be appreciated that in treating a disease or disorder that requires circulatory levels of the peptide, such factors as aerosol particle size, aerosol particle shape, the presence or absence of infection, lung disease, or emboli may affect the absorption of the peptides. For each of the formulations described herein, certain lubricators, absorption enhancers, protein stabilizers or suspending agents may be appropriate. The choice of these additional agents will vary depending on the goal. It will be appreciated that in instances where local delivery of the peptides is desired or sought, such variables as absorption enhancement will be less critical.

The liquid aerosol formulations of the present invention will typically be used with a nebulizer. The nebulizer can be either compressed air driven or ultrasonic. Any nebulizer known in the art can be used in conjunction with the present invention such as but not limited to the: ULTRAVENT™ nebulizer (Mallinckrodt, Inc., St. Louis, Mo.) or the ACORN II™ nebulizer (Marquest Medical Products, Englewood Colo.). Other nebulizers useful in conjunction with the present invention are described in U.S. Pat. Nos. 4,624,251; 3,703,173; 3,561,444; and 4,635,627.

The liquid aerosol formulation may include a carrier. The carrier is a macromolecule that is soluble in the circulatory system and that is physiologically acceptable where physiological acceptance means that those of skill in the art would accept injection of said carrier into a patient as part of a therapeutic regime. The carrier preferably is relatively stable in the circulatory system with an acceptable plasma half life for clearance. Such macromolecules include but are not limited to soya lecithin, oleic acid, and sorbitan trioleate, with sorbitan trioleate preferred.

The liquid aerosol formulations herein may also include other agents useful for protein stabilization or for the regulation of osmotic pressure. Examples of the agents include but are not limited to salts, such as sodium chloride or potassium chloride, and carbohydrates, such as glucose, galactose or mannose, and the like.

It is also contemplated that the present pharmaceutical formulation will be used as a dry powder inhaler formulation comprising a finely divided powder form of the peptide and a dispersant. The form of the peptide will generally be a lyophilized powder. Lyophilized forms of peptides can be obtained through standard techniques.

In another embodiment, the dry powder formulation will comprise a finely divided dry powder containing one or more peptides of the present invention, a dispersing agent and also a bulking agent. Bulking agents useful in conjunction with the present formulation include such agents as lactose, sorbitol, sucrose, or mannitol, in amounts that facilitate the dispersal of the powder from the device.

Combination therapy with the IGF agonist peptide herein and one or more other appropriate reagents that increase total IGF in the blood or enhance the effect of the IGF agonist is also part of this invention. These reagents generally allow the IGF agonist peptide herein to release the generated IGF, and include growth-promoting agents.

Growth-promoting agents for this purpose include, but are not limited to, GH secretagogues that promote the release of endogenous GH in mammals to increase concentrations of the IGF in the blood. Examples include TRH, diethylstilbestrol, theophylline, enkephalins, E series prostaglandins, peptides of the VIP-secretin-glucagon-GRF family, and other GH secretagogues such as GHRP-6, GHRP-1 as described in U.S. Pat. No. 4,411,890, and benzo-fused lactams such as those disclosed in U.S. Pat. No. 5,206,235. See also, e.g., WO 96/15148 published May 23, 1996. Other growth-promoting agents include GHRPs, GHRFs, GH and their analogs. For example, GHRPs are described in WO 95/17422 and WO 95/17423, both published June 29, 1995; Bowers, *J. Pediatr. Endocrinol.*, 6: 21–31 (1993); and Schoen et al., *Annual Reports in Medicinal Chemistry*, 28: 177–186 (1993). GHRFs and their analogs are described, for example, in WO 96/37514 published Nov. 28, 1996.

Additionally, GHRH, any of the IGFBPs, long-acting GH, GH plus GHBP, insulin, or a hypoglycemic agent can be employed in conjunction with the IGF agonist peptide herein for this purpose. In addition, IGF-I or IGF-II or an IGF with an IGFBP such as IGF-I complexed to IGFBP-3 can also be employed with the IGF agonist peptide herein. For example, pharmaceutical compositions containing IGF-I and IGFBP in a carrier as described in WO 94/16723 published Aug. 4, 1994 can be used in conjunction with the peptide. The entities can be administered sequentially or simultaneously with the IGF agonist peptide. In addition, other means of manipulating IGF status, such as regimens of diet or exercise, are also considered to be combination treatments as part of this invention.

If insulin is also administered, it can be any formulation of insulin, such as Regular, Lente, or NPH insulin, and the dose of insulin is typically from about 5 to 50 units/injection (i.e., from about 0.2 to 2 mg) twice a day subcutaneously. For a combination of insulin and the peptide, the ratio of insulin to peptide in this formulation by weight is generally from about 10:1 to 1:50, preferably from about 1:1 to 1:20, more preferably from about 1:1 to 1:10, still more preferably, from about 1:1 to 1:5, and most preferably from about 1:1 to 1:3.

Furthermore, the formulation is suitably administered along with an effective amount of a hypoglycemic agent such as a sulfonylurea. The hypoglycemic agent is administered to the mammal by any suitable technique including parenterally, intranasally, orally, or by any other effective route. Most preferably, the administration is by the oral route. For example, MICRONASE™ tablets (glyburide) marketed by Upjohn in 1.25, 2.5, and 5 mg tablet concentrations are suitable for oral administration. The usual maintenance dose for Type II diabetics, placed on this therapy, is generally in the range of from or about 1.25 to 20 mg per day, which may be given as a single dose or divided throughout the day as deemed appropriate (*Physician's Desk Reference*, 2563–2565 (1995)). Other examples of glyburide-based tablets available for prescription include GLYNASE™ brand drug (Upjohn) and DIABETA™ brand drug (Hoechst-Roussel). GLUCOTROL™ (Pratt) is the trademark for a glipizide (1-cyclohexyl-3-(p-(2-(5-methylpyrazine carboxamide)ethyl)phenyl)sulfonyl)urea) tablet available in both 5- and 10-mg strengths and is also prescribed to Type II diabetics who require hypoglycemic therapy following dietary control or in patients who have ceased to respond to other sulfonylureas (*Physician's Desk Reference*, 1902–1903 (1995)). Other hypoglycemic agents than sulfonylureas, such as the biguanides (e.g., metformin and phenformin) or thiazolidinediones (e.g., troglitozone), or other drugs affecting insulin action may also be employed. If a thiazolidinedione is employed with the peptide, it is used at the same level as currently used or at somewhat lower levels, which can be adjusted for effects seen with the peptide alone or together with the dione. The typical dose of troglitazone (REZULIN™) employed by itself is about 100–1000 mg an per day, more preferably 200–800 mg/day, and this range is applicable herein. See, for example, Ghazzi et al., *Diabetes*, 46: 433–439 (1997). Other thiazolidinediones that are stronger insulin-sensitizing agents than troglitazone would be employed in lower doses.

Another aspect of this invention is a composition comprising a combination of an IGF, a thiazolidinedione, and a peptide of this invention. Additionally, a method for effecting glycemic control is provided by administering to a mammal in need thereof an effective amount of an IGF, a thiazolidinedione, and a peptide of this invention. The active agents may be administered to the mammal sequentially or together, whether in the same formulation or concurrently. Effective amounts are determined by the practitioner as described above and would generally mean an amount the same or less than the amount of IGF that is used to treat the condition in question (for example, from about 10 to about 250 μg/kg/day of IGF-I for diabetes) and an amount of dione that is known to be useful to treat the condition in question, or if the three are used, the amount of peptide using the dosages as determined above.

In addition, the invention contemplates using gene therapy for treating a mammal, using nucleic acid encoding the IGF agonist peptide. Generally, gene therapy is used to increase (or overexpress) IGF levels in the mammal. Nucleic acids that encode the IGF agonist peptide can be used for this purpose. Once the amino acid sequence is known, one can generate several nucleic acid molecules using the degeneracy of the genetic code, and select which to use for gene therapy.

There are two major approaches to getting the nucleic acid (optionally contained in a vector) into the patient's cells for purposes of gene therapy: in vivo and ex vivo. For in vivo delivery, the nucleic acid is injected directly into the patient, usually at the site where the IGF agonist peptide is required. For ex vivo treatment, the patient's cells are removed, the nucleic acid is introduced into these isolated cells and the modified cells are administered to the patient either directly or, for example, encapsulated within porous membranes which are implanted into the patient. See, e.g. U.S. Pat. Nos. 4,892,538 and 5,283,187. There are a variety of techniques available for introducing nucleic acids into viable cells. The techniques vary depending upon whether the nucleic acid is transferred into cultured cells in vitro or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retrovirus. The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE, and DC-Chol, for example). In some situations it is desirable to provide the nucleic acid source with an agent that targets the target cells, such as an antibody specific for a cell surface membrane protein or the target cell, a ligand for a receptor on the target cell, etc. Where liposomes are employed, proteins that bind to a cell-surface membrane protein associated with endocytosis may be used for targeting and/or to facilitate uptake, e.g., capsid proteins or fragments thereof tropic for a particular cell type, antibodies for proteins that undergo internalization in cycling, and proteins that target intracellular localization and enhance intracellular half-life. The technique of receptor-mediated endocytosis is described, for example, by Wu et al., *J. Biol. Chem.*, 262: 4429–4432 (1987) and Wagner et al., *Proc. Natl. Acad. Sci. USA*, 87: 3410–3414 (1990). For review of the currently known gene marking and gene therapy protocols, see Anderson et al., Science, 256: 808–813 (1992). See also WO 93/25673 and the references cited therein.

Kits are also contemplated for this invention. A typical kit would comprise a container, preferably a vial, for the IGF agonist peptide formulation comprising IGF agonist peptide in a pharmaceutically acceptable buffer and instructions, such as a product insert or label, directing the user to utilize the pharmaceutical formulation. The kit optionally includes a container, preferably a vial, for a GH, a GHRP, a GHRH, a GH secretagogue, an IGF, an IGF complexed to an IGFBP, an IGFBP, a GH complexed with a GHBP, insulin, or a hypoglycemic agent.

In another embodiment herein, a method is provided for directing endogenous IGF either away from, or towards, a particular site in a mammal comprising administering to the mammal an effective amount of the peptide herein that is specific for an IGFBP that is either prevalent at, or absent from, the site. "Sites" for this purpose include specific tissues or organs such as the heart, or such as the brain via brain-specific IGFBPs. Prevalence at the site indicates that the IGFBP in question is located at the site and constitutes a substantial or biologically-important portion of the IGFBP at the site. This indication follows from the specificity for IGFBP-1 versus IGFBP-3 of the peptides demonstrated herein.

The invention will be more fully understood by reference to the following examples. They should not, however, be construed as limiting the scope of the invention. The disclosures of all literature and patent citations mentioned herein are expressly incorporated by reference.

EXAMPLES

Peptides mentioned herein as starting materials and/or intermediates are described in WO 98/45427, supra. In addition, data on a model compound (an IGF-I mutant with amino acid changes at residues 24 and 31 (Y24L,Y31A), also designated ($Leu^{24}$,$Ala^{31}$)hIGF-I or IGF-M) for predicting behavior of the peptides herein in vitro and in vivo is also disclosed in WO 98/45427, supra, as well as how to dose an IGF agonist for use in humans, where from the doses of IGF-I used and the concentrations of IGFBP and IGF-I and IGF-II demonstrated, it is simple to calculate how much of an IGF agonist should be given to increase levels of active endogenous IGF. The molar size relative to IGF-I, the affinity of the IGF agonist for the IGFBP, and its bioavailability would be other variables taken into account to arrive at doses that increased active IGF in a human.

Using either polyvalent phage display (by fusion to the major coat protein, g8p, of bacteriophage M13) or monovalent display (by fusion to g3p; for a review, see Lowman, Annu. Rev. Biophys. Biomol. Struct., 26: 401–424 (1997)) of the bp1-01 or bp1-02 peptide, a variety of substitutions were found to be tolerated by the peptide with little or no effect on its binding affinity to IGFBP-1 (WO 98/45427, supra). A few positions could not be substituted by alanine or other natural or non-natural amino acid residues without significant loss of binding. These included C1 and C10 (disulfide-bonded Cys residues; numbering is according to the sequence of bp1-01 or bp1-16 described in WO 98/45427, supra), as well as P5, L6, and L9. While some substitutions were tolerated at W8, K12, Y13, and F14, alanine substitutions caused smaller (about 10-fold or less) reductions in binding affinity. Simultaneous substitution of Y13A/F14A caused a >100-fold loss in affinity (bp1-18), and deletion of the Lys-Tyr-Phe residues resulted in >1000-fold loss in binding affinity (bp1-17).

On the other hand, substitutions of the N-terminal four residues of bp1-02, and additions to the C-terminus of bp1-02, yielded affinity improvements of about 5-fold. For example, addition of Ser-Thr-Tyr to the C-terminus of bp1-02 resulted in a 3.2-fold improvement in apparent affinity (bp1-21A), and mutation of the initial four amino acids of bp1-02 resulted in a 2.6-fold improvement in apparent affinity (bp1-20).

Example 1

Substitutions in bp1-16

Several single-residue substitutions in bp1-16 were tested for their effect on IGFBP-1 binding affinity by synthesizing peptides and measuring inhibition of IGFBP-1 binding to IGF-I. Sites for substitution were chosen based upon the known effect of an alanine or other substituted residue at the site.

G4 was previously found to be substitutable by D-alanine. Because the conformational effects of D-alanine are different from those of L-alanine, L-alanine was substituted for G4 in peptide bp1-29. Inhibition assays showed a 50-fold loss in binding affinity with this substitution (Table I).

P5 was previously found to be highly conserved in phage-displayed peptide libraries; however, some substitutions were observed. For example, three different peptide-phage clones were found with arginine at this position. Therefore, the L-alanine substitution for proline was tested, as well as several alternative substitutions (bp1-30, bp1-31, bp1-34). The results (Table I) show that PSA, PSN, and P5R are well tolerated.

L6 and L9 were completely conserved in 40 of 40 sequenced clones and 61 of 61 sequenced clones, respectively, from two different IGFBP-1 selected peptide-phage libraries. In addition, 94 substitution of either of these residues with L-alanine or aib (alpha-aminoisobutyrate) side-chains resulted in a significant loss in IGFBP-1 binding affinity. Two further substitutions were tested at each position: norleucine (Nle), an isomer of leucine, or arginine (the aliphatic portion of the side-chain of which might still be able to pack into the peptide structure). While the Arg substitutions resulted in peptides having undetectable IGFBP-1 affinity (bp1-32 and bp1-26), the Nle substitutions were well-tolerated (bp1-36 and bp1-37). The non-natural substitutions L6(Nle) and L9(Nle) are therefore the only substitutions at these positions known to preserve moderate-affinity binding to IGFBP-1.

W8 was also completely conserved in IGFBP-1 selected peptide-phage libraries, although the alanine substitution had a smaller effect on binding than in the case of L6 or L9. Therefore, several large side-chain substitutions were tested at this position. Interestingly, arginine, 1-naphthylalanine (Nal(1)), or histidine substitutions (bp1-22, bp1-23, and bp1-24, respectively) each had modest (<10-fold) effects on IGFBP-1 binding affinity (Table I).

From these experiments, a new consensus sequence for IGFBP-1 binding may be formulated as follows:

CysXaa$_{(6)}$Xaa$_{(7)}$GlyXaa$_{(9)}$Xaa$_{(10)}$Xaa$_{(11)}$TrpXaa$_{(13)}$ CysXaa$_{(15)}$Xaa$_{(16)}$Xaa$_{(17)}$Xaa$_{(18)}$ (SEQ ID NO:3), where Xaa$_{(6)}$, Xaa$_{(7)}$, Xaa$_{(9)}$, Xaa$_{(11)}$, Xaa$_{(15)}$, and Xaa$_{(16)}$ are independently any amino acid, Xaa$_{(10)}$ and Xaa$_{(13)}$ are independently Leu or Nle, and Xaa$_{(12)}$, Xaa$_{(17)}$, and Xaa$_{(18)}$ are independently Nal(1), His, Phe, Trp, Tyr, Pro, Gln, or Met.

TABLE I

| bp1-16 Variant | Peptide Sequence | Fold potency reduction $IC_{50}$(mut)/ $IC_{50}$(bp1-16) |
|---|---|---|
| | Relative affinities of bp1-16 variants measured by ELISA or BIAcore ™(*) inhibition assays | |
| bp1-16 | CRAGPLQWLCEKYF (SEQ ID NO:37) | -1- |
| bp1-29 | CRAAPLQWLCEKYF (SEQ ID NO:38) | 50 |
| bp1-30 | CRAGALQWLCEKYF (SEQ ID NO:4) | 1.5 |
| bp1-31 | CRAGRLQWLCEKYF (SEQ ID NO:5) | 2.0 |
| bp1-34 | CRAGNLQWLCEKYF (SEQ ID NO:6) | 3.1 |
| bp1-32 | CRAGPRWLCEKYF (SEQ ID NO:39) | >1000 |
| bp1-36 | CRAGPXQWLCEKYF (SEQ ID NO:7), where the underlined X is Nle | 6.9 |
| bp1-26 | CRAGPLQWRCEKYF (SEQ ID NO:40) | >570 |
| bp1-37 | CRAGPLQWXCEKYF (SEQ ID NO:8), where the underlined X is Nle | 1.7 |
| bp1-22 | CRAGPLQRLCEKYF (SEQ ID NO:9) | 3.3* |
| bp1-23 | CRAGPLQXLCEKYF (SEQ ID NO:10), where the underlined X is Nal(1) | 4.8* |
| bp1-24 | CRAGPLQHLCEKYF (SEQ ID NO:11) | 7.5 |

Example 2

Minimization of the bp1-01 Peptide Via "Locked Helix"

It was previously shown that removal of the disulfide bond in bp1-01 is destabilizing to both structure and function of the peptide. The possibility has been investigated of replacing the disulfide bond of bp1-01 with a chemically distinct structural constraint, while maintaining moderate binding affinity to IGFBP-1. These constraints were designed to link side-chain positions separated by 7 (from position i to position i+7) or 8 (from i to i+8) residues in the bp1-01 peptide.

The i+7 locked helix strategy, one of the approaches used herein, has been described by Phelan et al., *J. Am. Chem. Soc.*, 119: 455–460 (1997); WO 98/20036 published May 14, 1998, as have other i+7, i+3, and i+4 linkages (reviewed in Phelan et al., supra). In addition, other side-chain substitutions, allowing for ionic or hydrophobic interactions or metal chelation, have been used for the purpose of stabilizing a helical structure (reviewed by Phelan et al., supra). Herein is described a novel i+8 locked helix strategy, which is particularly useful for stabilization of the helical structure found in the bp1-01 peptide family.

Mutagenesis studies indicated that major determinants for IGFBP-1 binding reside primarily in the helical segment of bp1-01. These important binding determinants segregate mainly to one face of the helix, and include Leu6 and Leu9, and the aromatic residues Trp8, Tyrl3, and Phel4. Without being limited to any one theory, the remainder of the peptide might act primarily to stabilize the helix and to ensure appropriate presentation of the major side-chain binding determinants. Therefore, other methods for constraining the binding segment of the peptide to a helical conformation might yield potent BP1-binding peptides. Side-chain-5 side-chain crosslinks on the opposite helical face from the major BP1-binding determinants were chosen for use. This method has been described in WO 98/20036, supra. In the present case, the i+7 crosslinking connects residues replacing Gln7 to Phe14, which replaces one of the hydrophobic IGFBP-1 binding determinants. The i+8 crosslinking connects residues replacing Gln7 to Gly15.

The crosslinking chemistry involves replacement of the appropriate two residues with glutamic acid residues (the first and last Glu (E) residues shown in Table II), where the two Glu residues are joined by forming amides with 1,5-diaminopentane. This cross-linking method has been described in WO 98/20036, supra.

To develop active peptides shorter than bp1-01, it was also decided to delete the disulfide (Cys1–Cys10) and truncate the N-terminal loop region in constrained helical peptides. The Cys10 was changed to Ala and Cys1 replaced with an acetyl group (ac in Table II). Several shorter variants lacked one or more of the other loop residues. Thus, these peptides were cyclized only through the 1,5-diaminopentane linkage. Such peptides, lacking disulfide bonds, may be more stable to degradation in vitro and in vivo. They may also be reduced in immunogenicity compared to disulfide-containing analogs.

Functional Analysis of Locked Helices

Peptides were assayed in a BIAcore™ assay as described in WO 98/45427, supra. These inhibition assays (FIG. 1) compared the relative potency of these peptides for blocking the interaction of IGFBP-1 with IGF-1. Adding the "i+7 helical lock" to a variant of bp1-01 reduced relative potency (Table II) by 6-fold (peptide (i+8)C) to 8-fold (peptide (i+7)D or (i+8)B) in the best locked-helix variants. These peptides demonstrate that a disulfide bond is not necessary to obtain structured, functional peptides of the bp1-01 family.

In contrast to the locked helix variants described above, a locked helix variant in which two of the key IGFBP-1 binding determinants were lost ((i+7)A; Table II) exhibited significant loss in binding activity relative to bp1-01. In this peptide, W8 is replaced with the first cross-linking residue and Gly15 is replaced with the second cross-linking residue; F14 is replaced by alanine in this peptide. The disulfide bond is still present in this peptide.

Certain additions to the N-terminus and C-terminus of these peptides (see Example 3) are predicted to improve their binding affinity and potency, as in the case of disulfide-constrained peptide variants discussed below.

Hence, a consensus sequence can be formulated as follows: $Xaa_{(1-4)}Xaa_{(5)}Xaa_{(6-7)}$ProLeuGlu$Xaa_{(11)}$LeuAla $Xaa_{(14)}Xaa_{(15)}Xaa_{(16)}$ $Xaa_{(17)}$Glu$Xaa_{(19)}$ (SEQ ID NO:32), wherein $Xaa_{(1-4)}$ is absent or is between 1 and 4 amino acids of any kind; $Xaa_{(5)}$ is any amino acid, $Xaa_{(6-7)}$, is absent or is between 1 and 2 amino acids, $Xaa_{(14)}$ and $Xaa_{(15)}$ are independently any amino acid, $Xaa_{(11)}$ and $Xaa_{(16)}$ are independently Nal(1), His, Phe, Trp, Tyr, Pro, Gln, or Met, $Xaa_{(17)}$ is absent or is 1-napthyl-Ala, His, Phe, Trp, Tyr, Pro, Gln, or Met, and $Xaa_{(19)}$is absent or is Gly.

NMR Analysis of Locked Helices $^{1}$H NMR spectroscopy was used to ascertain that the locked helix variants of bp1-01 did have the desired three-dimensional helical structure. 1-dimensional spectra and 2-dimensional COSY, TOCSY, and ROESY spectra were acquired for peptides (i+7)A, (i+7)B, (i+7)C, (i+7)D and (i+8)C; experimental details were similar to those described for bp1-01 in Lowman et al., supra, 1998. Preliminary analysis of backbone $^{3}J_{HN-H\alpha}$ scalar coupling constants (derived from 2D COSY spectra) and short $H^{\alpha}(i)$-$H^{N}(i+3)$ distances (derived from ROESY spectra), indicated that for (i+7)A, (i+7)C, (i+7)D, and (i+8)C, the designed helix was present. In the case of (i+7)B, the NMR data were not consistent with a helical structure. The lack of a well-folded structure presumably explains the low affinity of this peptide for IGFBP-1 (>360 fold weaker than bp1-01).

The scalar coupling and ROESY data for (i+7)A, (i+7)D, and (i+8)C were analyzed in more detail to generate input restraints for the calculation of three-dimensional structures as described previously for bp1-01 (Lowman et al., supra, 1998). Comparison of the minimized mean structures of the locked helix variants to that of bp1-01 yielded RMSDs (N', Ca, C atoms of Leu6-Phe14) of 1.02 Å and 0.22 Å for (i+7)D and (i+8)C, respectively. Further, the packing of hydrophobic side-chains Leu6, Trp8, Leu9, and Tyr13 in these two locked helix variants was also very similar to the packing in bp1-01. Thus, the (i, i+7) and (i,i+8) locked helix scaffolds have successfully maintained many aspects of the bp1-01 structure without the need for a disulfide bond. Although the covalent tethers in (i+7)A did produce the desired two turns of helix (the N,Ca,C RMSD between minimized means of bp1-01 and (i+7)A is 1.06 Å), some side- chain rotamers differed significantly from those of bp1-01.

The structural analyses described above suggest that covalent tethers (other than the disulfide bond observed in bp1-01) may be used to control peptide structure. The use of i,i+7 or i,i+8 tethers produced peptides (i+7)D and (i+8)C that retained high affinity towards IGFBP-1 in the absence of a disulfide bond. Presumably, the affinity derives from stabilization of a structure that maintains both the backbone helical fold and the side-chain packing arrangement of the key binding determinants observed in bp1-01. Although the peptide (i+7)A maintains the backbone fold, two of the key determinants (Trp8 and Phe14) are missing, and the orientation of others (e.g. Tyr13) is perturbed; as a result, this peptide has reduced affinity. The peptide (i+7)B fails to adopt the desired fold, and hence has no measurable affinity for IGFBP-1.

TABLE II

Locked-helix variants of bp1-01
(The first and last Glus (Es) are sites of cyclizing "lock")

| bp1-16 Variant | Peptide Sequence | Fold potency reduction $IC_{50}$ (bp1-01)/$IC_{50}$ (mut) |
|---|---|---|
| bp1-01 | CRAGPLQWLCEKYFG (SEQ ID NO:41) | -1- |
| (i + 7)A | acCRAGPLQELCEKYAE (SEQ ID NO:42) | 40 |
| (i + 7)B | acLEWLAEKYEG (SEQ ID NO:43) | >360 |
| (i + 7)C | acPLEWLAEKYEG (SEQ ID NO:44) | 20 |
| (i + 7)D | acRAGPLEWLAEKYEG (SEQ ID NO:34) | 7.7 |
| (i + 8)A | acLEWLAEKYFE (SEQ ID NO:45) | >200 |
| (i + 8)B | acRPLEWLAEKYFE (SEQ ID NO:35) | 7.7 |
| (i + 8)C | acRAGPLEWLAEKYFE (SEQ ID NO:36) | 5.9 |

Example 3

N-terminal Variants of bp1-16

Previous affinity-maturation experiments led to a peptide addition to the C-terminus of bp1-02, including a number of peptide-phage clones (Table III), and the synthetic peptide bp1-21A, the sequence of which is shown in Table III. Table III illustrates the C-terminal substitutions in the background of bp1-02.

TABLE III

C-terminal substitutions derived from round 3 of monovalent phage selections in the bp1-02 peptide background

| bp1-02 Variant | Peptide Sequence | SEQ ID NO: | Number of clones sequenced |
|---|---|---|---|
| Y135C (bp1-21A) | SEVGCRAGPLQWLCEKYFSTY | 13 | 2 |
| Y135D | SEVGCRAGPLQWLCEKYFATY | 14 | 3 |
| Y135F | SEVGCRAGPLQWLCEKYFQTY | 15 | 1 |
| Y135B | SEVGCRAGPLQWLCEKYFQTYT | 16 | 1 |
| Y135A | SEVGCRAGPLQWLCEKYFDTY | 17 | 1 |
| Y135E | SEVGCRAGPLQWLCEKYFETY | 18 | 1 |
| Y135K | SEVGCRAGPLQWLCEKYFKTY | 19 | 1 |

It is sought herein to improve affinity further by two methods: substitution of the first four N-terminal amino acid residues from bp1-20 into bp1-21A, and re-randomization of the N-terminal amino acid residues of bp1-21A (in the context of the previously improved C-terminus).

Peptide bp1-25 (Table V) was synthesized to test the additivity (Wells, *Biochemistry*, 29: 8509–8517 (1990)) for the N-terminal and C-terminal maximally-preferred substitutions. Compared with bp1-16 in inhibition assays, bp1-25 showed about a 20-fold affinity improvement. However, the affinity of bp1-25 was not significantly improved over bp1-21A. This affinity improvement was confirmed in other assays described below.

In the second approach, a monovalent-display peptide-phage library, presenting bp1-21A as a fusion to g3p, was randomized (Lowman, *Methods Mol. Biol.*, 87: 249–264 (1998)) at the N-terminal four residues. Binding selection to IGFBP-1 was carried out by first allowing library phage to bind to solution biotinylated IGFBP-1, with an initial concentration of 50 nM, followed by 28 nM for the subsequent four rounds of selection. Peptide-phage capable of binding IGFBP-1 were captured by incubating with streptavidin magnetic beads (Promega) for 10 minutes at room temperature. For each round of selection, the washing was gradually modified to be more stringent. Off-rate selection was performed by adding 2.5–5 $\mu$M IGF in solution to prevent rebinding of phage with faster off-rates. It is of interest to note that for the last round of selection (round 5), with an overnight incubation at 4° C. in the presence of 2.5 EM IGF, there were still phage remaining bound to the beads ($2.2 \times 10^{04}$ total phage were eluted). Subsequent sequencing data revealed that 14 out of 20 selected clones had converged to a single DNA sequence (clone Y0791A; Table IV). A peptide corresponding to this sequence, bp1-40, was synthetically produced for analysis.

TABLE IV

N-terminal substitutions derived from round 5 of monovalent phage selections in the bp1-21A peptide background

| bp1-16 Variant | Peptide Sequence | SEQ ID NO: | Number of clones sequenced |
|---|---|---|---|
| Y0791A (bp1-40) | GQQSCRAGPLQWLCEKYFSTY | 21 | 14 |
| Y0791D | ASSMCRAGPLQWLCEKYFSTY | 22 | 1 |
| Y0791H | QGPDCRAGPLQWLCEKYFSTY | 23 | 1 |
| Y0791K | QASECRAGPLQWLCEKYFSTY | 24 | 1 |
| Y0791L | AETLCRAGPLQWLCEKYFSTY | 25 | 1 |
| Y0791S | NSLLCRAGPLQWLCEKYFSTY | 26 | 1 |
| Y0791T | AQWVCRAGPLQWLCEKYFSTY | 27 | 1 |

Inhibition assays for measuring relative potencies of peptides for inhibiting IGFBP-1 binding to IGF-I have been described (e.g., WO 9B/45427, supra). Peptides described herein were of sufficient binding affinity to allow for direct measurement of binding affinities by surface plasmon resonance (SPR) using a BIAcorem system. The direct binding kinetics of IGFBP-1 peptides were measured by injecting a series of 2-fold diluted peptides in running buffer (0.05% TWEEN 20™ in PBS) over a carboxy-methyl (CM) biosensor chip coupled with about 590–1000 RU of IGFBP-1 at a flow rate of 50 μl/min on a BIAcore-2000™ or BIAcore-30007™ instrument. The immobilization of IGFBP-1 was performed through EDC/NHS chemistry as described by the manufacturer. Peptides were also injected through a flow cell containing IGFBP-3 as background control. Since the off-rate for most of the peptides is relatively fast (in the range of $2 \times 10^{-2}$ s$^{-1}$), off-rate measurement was set for 30 minutes. This allowed for regeneration of IGFBP-1 on the chip by simple dissociation, rather than by addition of eluent. For each dilution of peptides, a global fit of the sensorgram data was performed using a 1:1 Langmuir binding model. On-rates ranged from $4 \times 10^5$ to $1.9 \times 10^6$ M$^{-1}$ s$^{-2}$. The binding affinities, $K_d$, calculated as $k_{off}/k_{on}$ are summarized in Table V. Peptides bp1-20, bp1-21A, bp1-25, and bp1-40 were all found to have similar binding affinities ($K_d$) of about 20 nM to 40 nM.

The conclusion from these experiments is that N-terminal extensions to the bp1-01 peptide can improve binding affinity (as in bp1-02, bp1-20, bp1-21A, bp1-25, bp1-40, and other variants identified in Table IV). Some substitutions may alter expression levels in E. coli, since GQQS (SEQ ID NO:46) was clearly selected from phage-displayed peptide libraries. However, peptides having the sequences SEVG (SEQ ID NO:47), SEMV (SEQ ID NO:48), EARV (SEQ ID NO:49), or GQQS (SEQ ID NO:46) at their N-termini all had similar binding affinities. Therefore, the nature of added side-chains at the N-terminus appears to have little effect upon peptide binding affinity. This suggests that main-chain interaction of the peptide in this region may contribute to binding affinity for IGFBP-1.

An improved consensus sequence for IGFBP-1 binding peptides is expected therefore to be:

Xaa$_{(1-4)}$CysXaa$_{(6)}$Xaa$_{(7)}$GlyXaa$_{(9)}$Xaa$_{(10)}$Xaa$_{(11)}$Xaa$_{(12)}$Xaa$_{(13)}$CysXaa$_{(15)}$Xaa$_{(16)}$Xaa$_{(17)}$Xaa$_{(18)}$ (SEQ ID NO: 1), wherein Xaa$_{(1-4)}$ is absent or is between 1 and 4 amino acids of any kind, Xaa$_{(6)}$, Xaa$_{(7)}$, Xaa$_{(9)}$, Xaa$_{(11)}$, Xaa$_{(15)}$, and Xaa$_{(16)}$ are independently any amino acid, Xaa$_{(10)}$ and Xaa$_{(13)}$ are independently Leu or Nle, and Xaa$_{(12)}$, Xaa$_{(17)}$, and Xaa$_{(18)}$ are independently Nal(1), His, Phe, Trp, Tyr, Pro, Gln, or Met. As noted in Example 1, truncation of the amino-terminal 4 residues (Xaa$_{(1-4)}$) has only a small effect on activity, giving a shorter consensus that still retains binding:

CysXaa$_{(6)}$Xaa$_{(7)}$GlyXaa$_{(9)}$Xaa$_{(10)}$Xaa$_{(11)}$TrpXaa$_{(13)}$ CysXaa$_{(15)}$Xaa$_{(16)}$Xaa$_{(17)}$Xaa$_{(18)}$ (SEQ ID NO:3).

TABLE V

Peptide affinity determinations by BIAcore ™ kinetics

| bp1-16 Variant | Peptide Sequence | $K_d$ ± (SD or SE) (nM) |
|---|---|---|
| bp1-02 | SEVGCRAGPLQWLCEKYFG (SEQ ID NO:50) | 210 ± 46 |
| bp1-20 | EARVCRAGPLQWLCEKYF (SEQ ID NO:2) | 33 ± 15 |

TABLE V-continued

Peptide affinity determinations by BIAcore ™ kinetics

| bp1-16 Variant | Peptide Sequence | $K_d$ ± (SD or SE) (nM) |
|---|---|---|
| bp1-21A | SEVGCRAGPLQWLCEKYFSTY (SEQ ID NO:13) | 41 ± 17 |
| bp1-25 | EARVCRAGPLQWLCEKYFSTY (SEQ ID NO:20) | 42 ± 11 |
| bp1-40 | GQQSCRAGPLQWLCEKYFSTY (SEQ ID NO:21) | 27 ± 21 |

Example 4

Cell-based Assay of Peptide Activity

A cell-based (KIRA) assay was previously described for measuring the amount of IGF-like activity displaced by peptides from mixtures of IGF-I and binding proteins (Lowman et al., supra, 1998; WO 98/45427, supra). The KIRA assay was used to compare in vitro bioactivity of bp1-16, bp1-02, bp1-25, and bp1-40. In this example, very low concentrations of IGF-I and IGFBP-1 were used, i.e., below the $k_d$ of the peptide: 2 nM [IGF-I] and 1.5 nM [IGFBP-1], with a titration series of [peptide]=0.1 to 200 nM. IGF-I and peptide were mixed and added to cells expressing IGF receptor for 30 min, then IGFBP-1 was added for an additional 1 h.

Increased potency was observed for both peptides bp1-25 and bp1-40 over peptides bp1-16 and bp1-02 (FIG. 2). However, under these conditions, bp1-02 was not significantly more active than bp1-16; and bp1-40 was not significantly more active than bp1-25. The EC$_{20}$ (concentration at which 20% of maximal IGF-I activity is observed) values were 10-20 nM for bp1-25 and bp1-40, and 150–200 nM for bp1-16 and bp1-02.

Example 5

Biosynthesis of a bp1-01 Peptide Variant

An additional variant of bp1-21A was designed for peptide biosynthesis in E. coli. For this approach, a DNA sequence encoding the peptide was fused by site-directed mutagenesis to the gene for a consensus domain of protein-A known as Z-domain (Nilsson et al., supra, 1987). After expression and secretion from E. coli, the fusion protein was enzymatically cleaved with trypsin to yield free peptide, which can be purified from the enzymatic reaction mix (see, e.g., Varadarajan et al., supra; Castellanos-Serra et al., supra; Nilsson et al., supra, 1996).

A detailed procedure for trypsin digestions has been described in Smith, supra. Because this protease is highly specific for Arg and Lys residues, the bp1-40 peptide was modified by mutation of these residues for construction of the fusion. From previous mutagenesis and phage-library results, it was known that Arg and Lys residues of bp1-01 could be substituted without significant loss of binding affinity. Therefore, a fusion protein was designed with substitutions R2A and K12H (numbering is according to the bp1-01 sequence). Furthermore, bp1-01, having a Gly residue following the C-terminal F14 of bp1-16, was known to have no significant effect on binding affinity. Therefore, a Gly-Arg sequence was added at the end of the peptide to allow for trypsin cleavage. The sequences of the bp1-625-Z fusion protein and the bp1-625 peptide (as cleaved by trypsin) are given in Table VI.

TABLE VI

Peptide sequences for E. coli biosynthesis

| Construct | Peptide sequence |
|---|---|
| bp1-625-Z | GQQSCAAGPLQWLCEHYFSTYGRGGGSGGAQHDEAVD NKFNKE QQNAFYEILHLPNLNEEQRNAFIQSLKDDPSQSANLLAE AKKLN DAQAPNVDMN (SEQ ID NO:51) |
| bp1-625 | GQQSCAAGPLQWLCEHYFSTYGR (SEQ ID NO:29) |

The fusion protein bp1-625-Z was produced from *E. coli* shake-flask cultures. Culture supernatants were sterile-filtered, then applied to an IgG-Sepharose™ column (Pharmacia). The bound fraction was eluted with 1M acetic acid, then lyophilized and resuspended in trypsin-digest buffer: 10 mM Tris (pH 8.0), 100 mM NaCl, 1 mM $CaCl_2$. TPCK-treated trypsin (Sigma) was added at a weight/weight ratio of 1:100 to 1:200 (trypsin to substrate) and digestion was carried out at 25° C. for 1–2 hours. Thereafter, PMSF was added to 1 mM to stop the reaction. Samples were adjusted to 1 mM TFA and run on an analytical HPLC column with a 0–60% acetonitrile gradient in 0.1% TFA. The two predominant peaks were collected (FIG. 3) and shown by mass spectrometry to correspond to a Z-domain fragment, and the peptide bp1-625.

Figure 4:
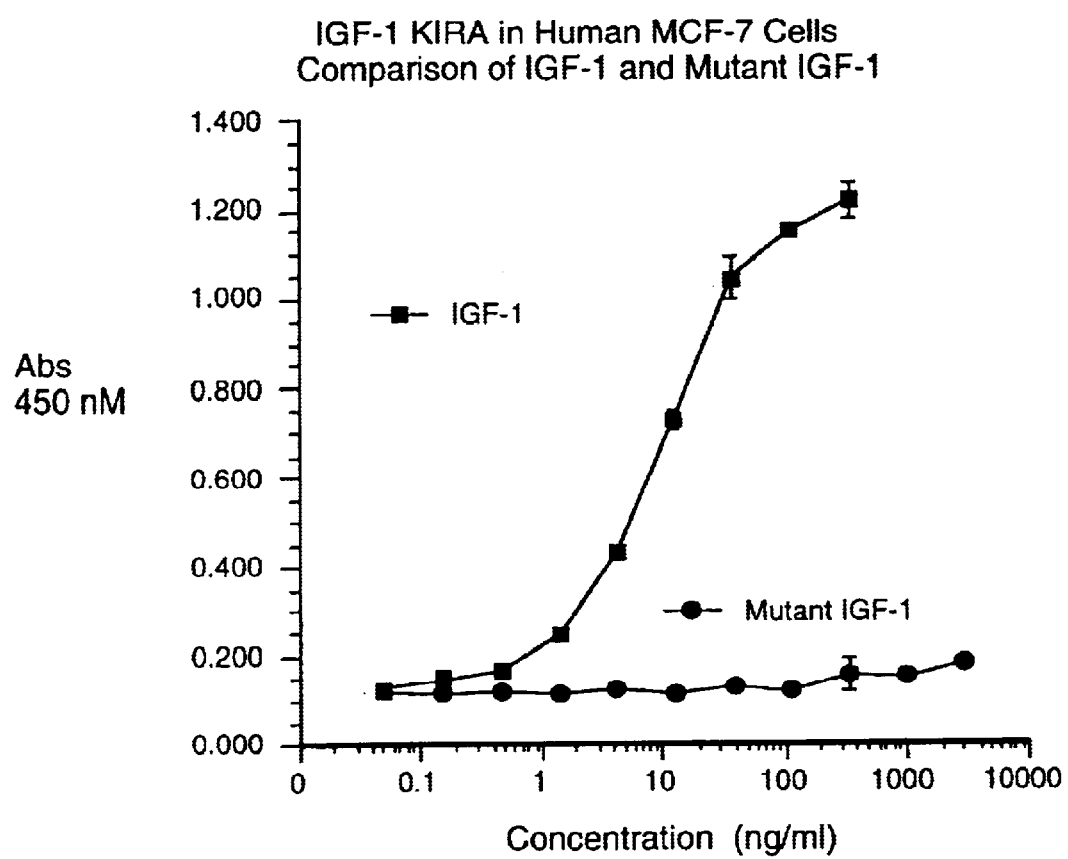
FIG. 4 shows a BIAcorem inhibition assay of IGF-I activity using four different peptides (bp1-16: circles, bp1-02: squares, bp1-25: triangles, and bp1-40: diamonds).
Figure 5:
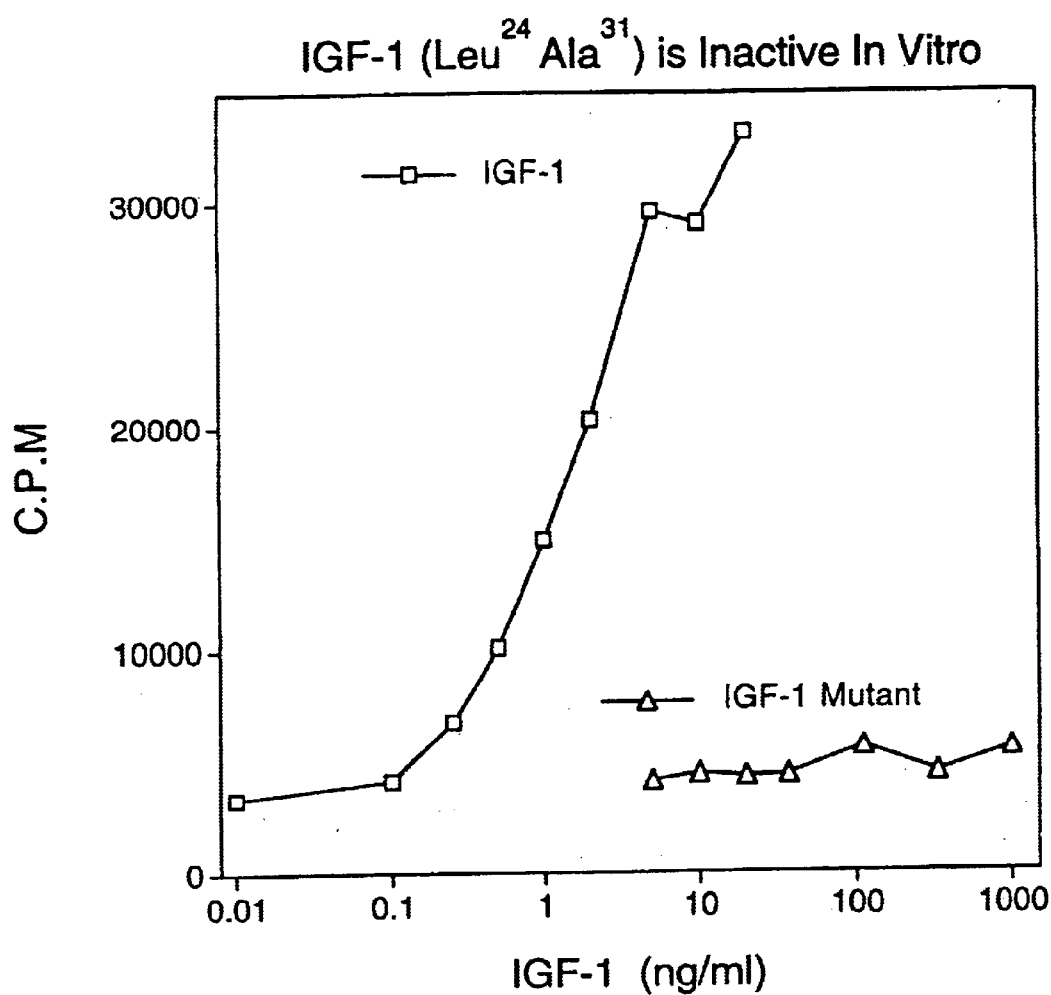
Figure 6:
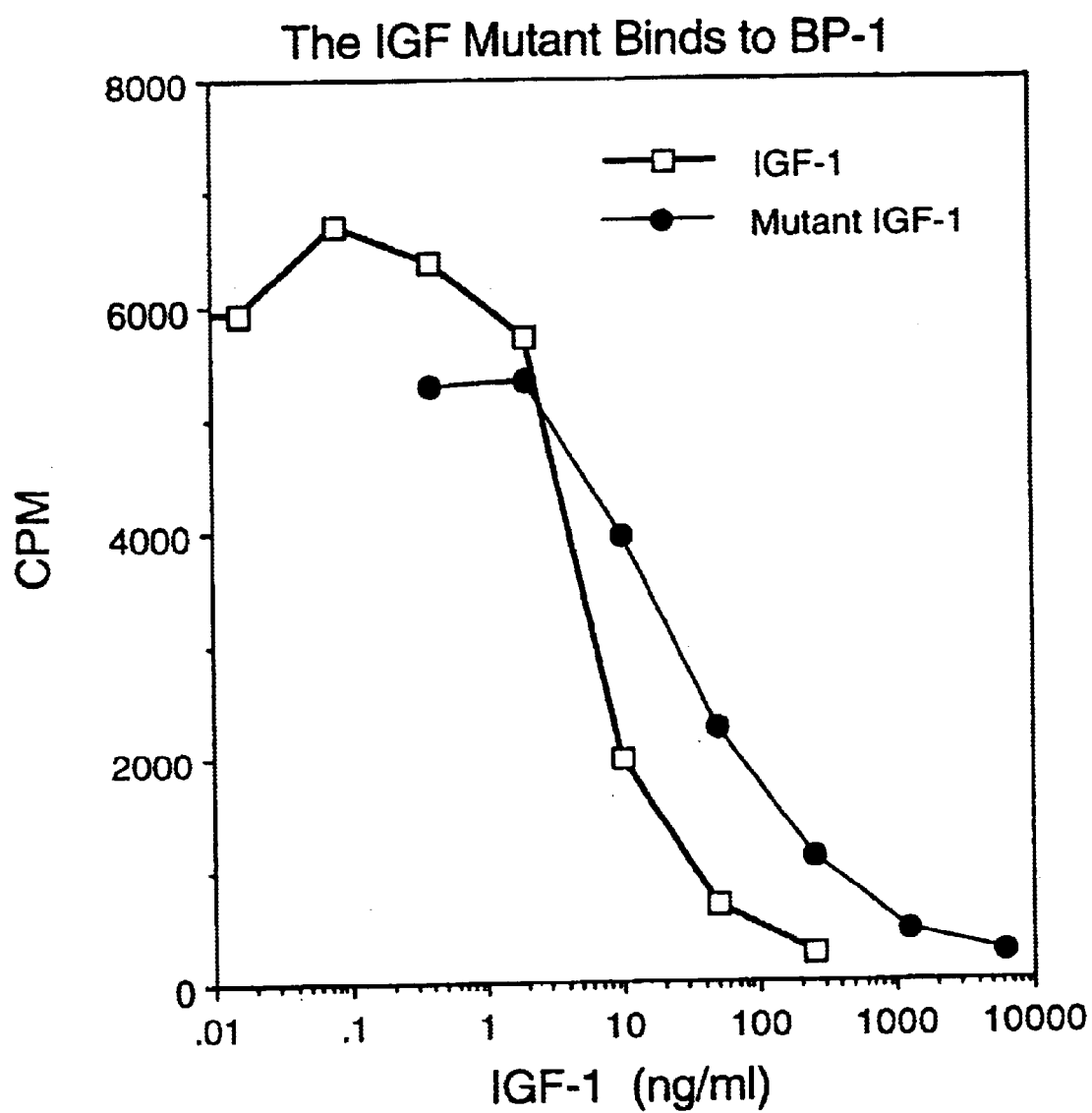
Figure 7:
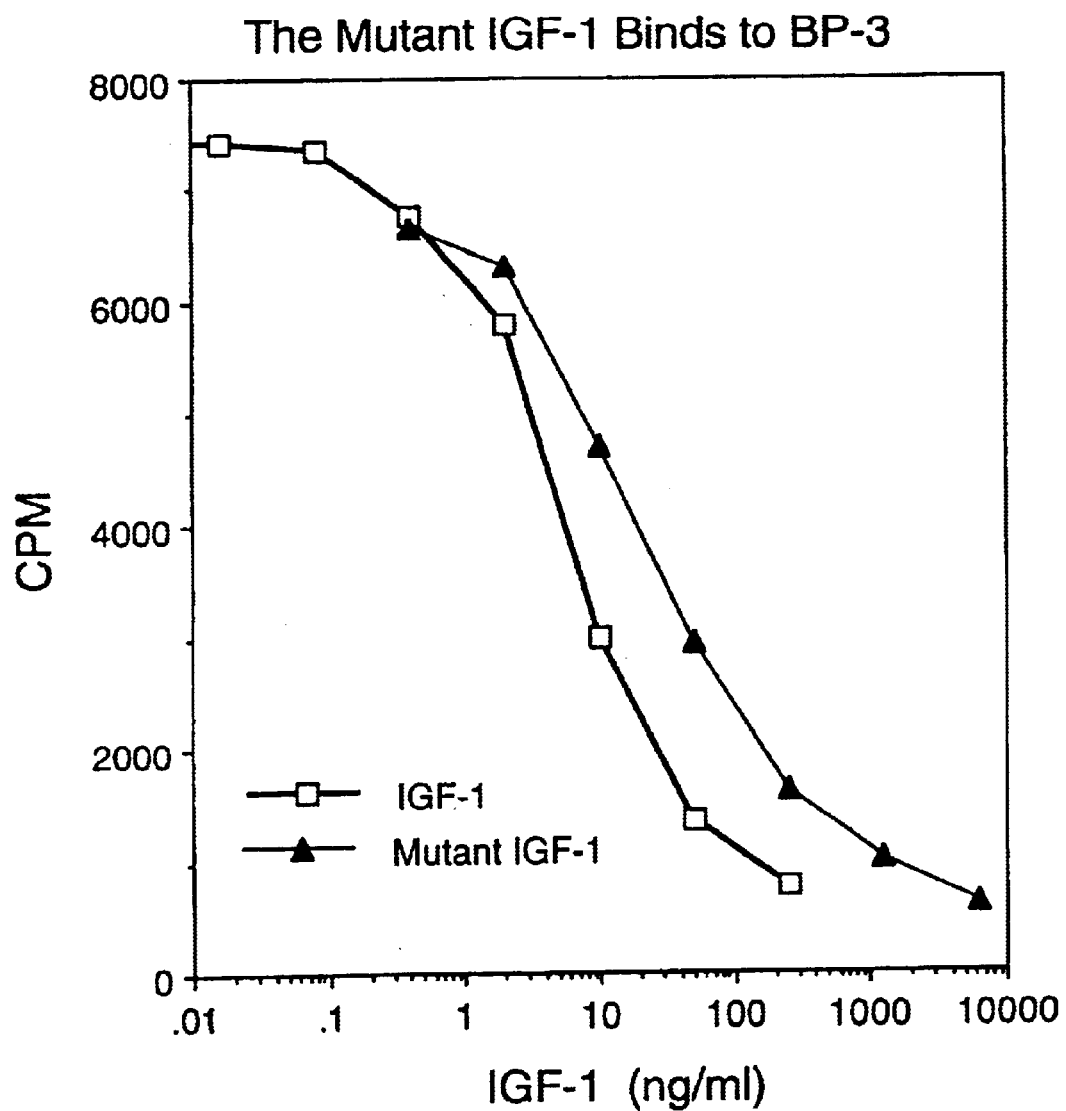
Figure 8A:
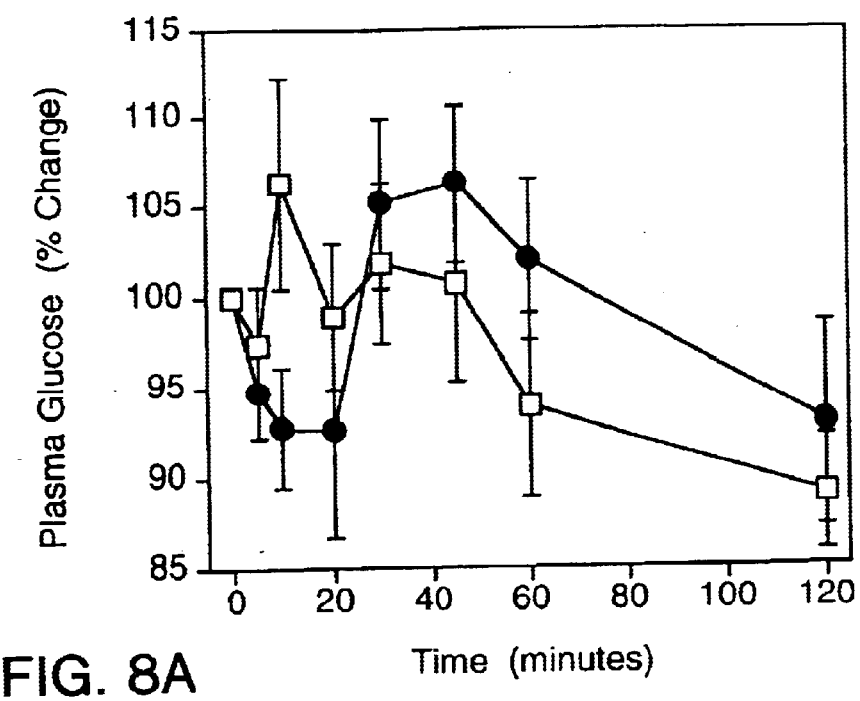
Figure 8B:
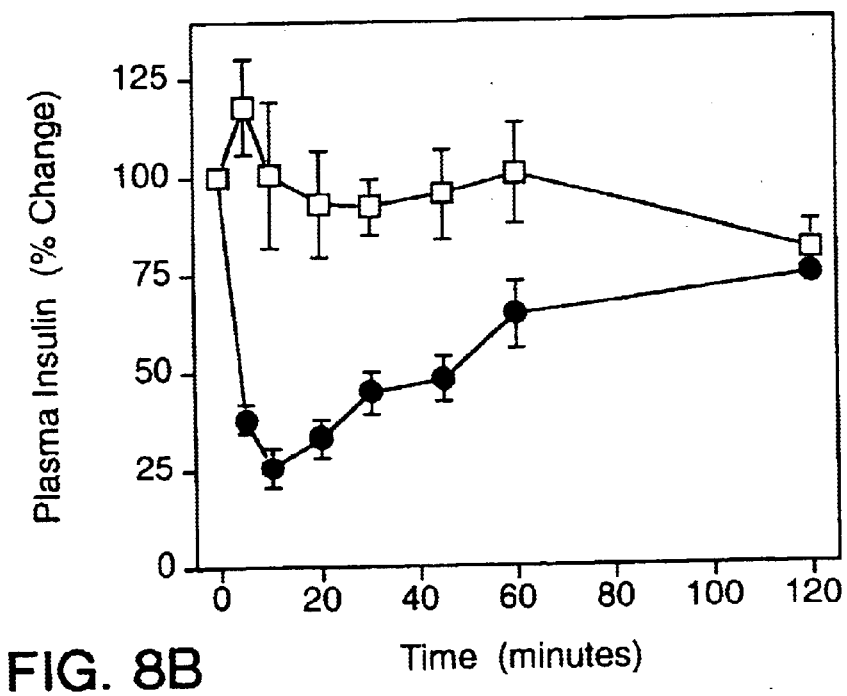
Figure 9A:
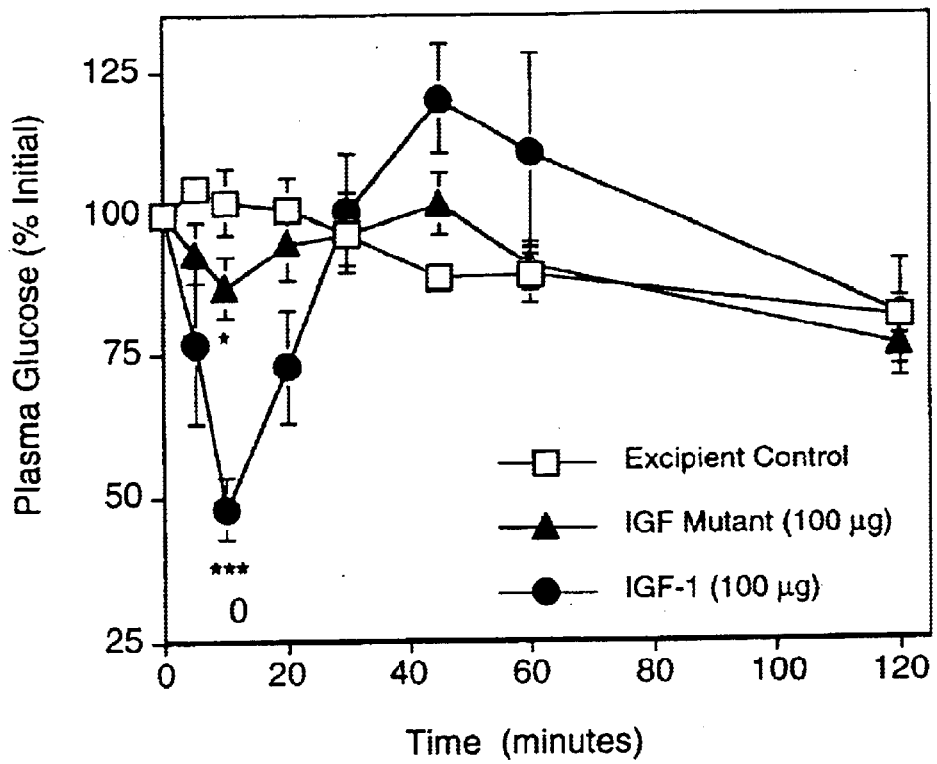
Figure 9B:
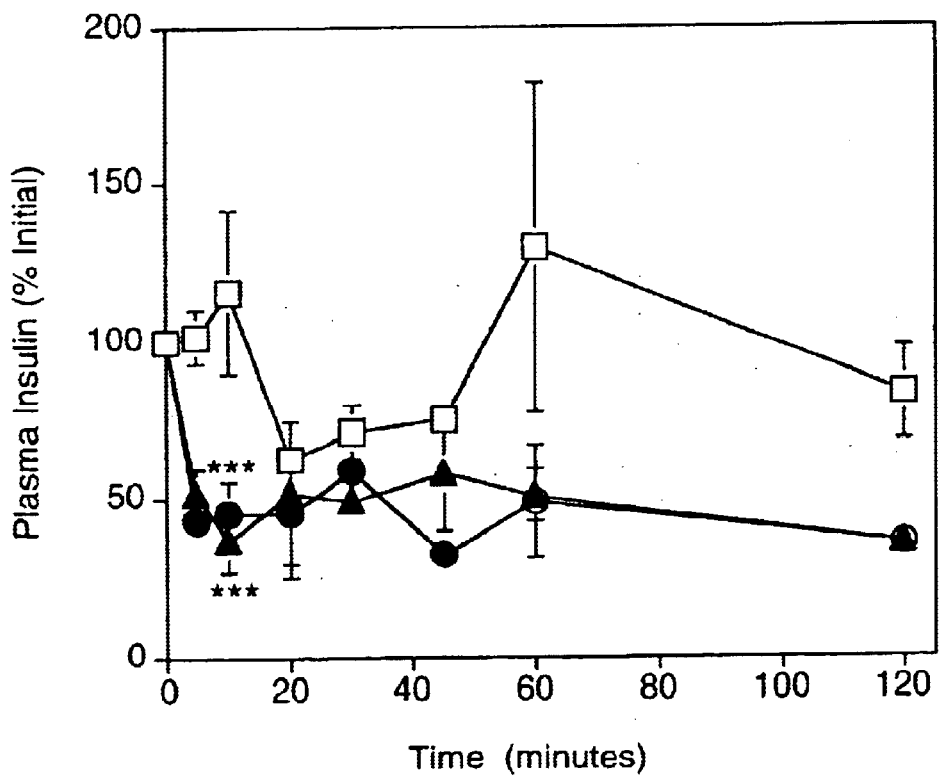
Figure 10A:
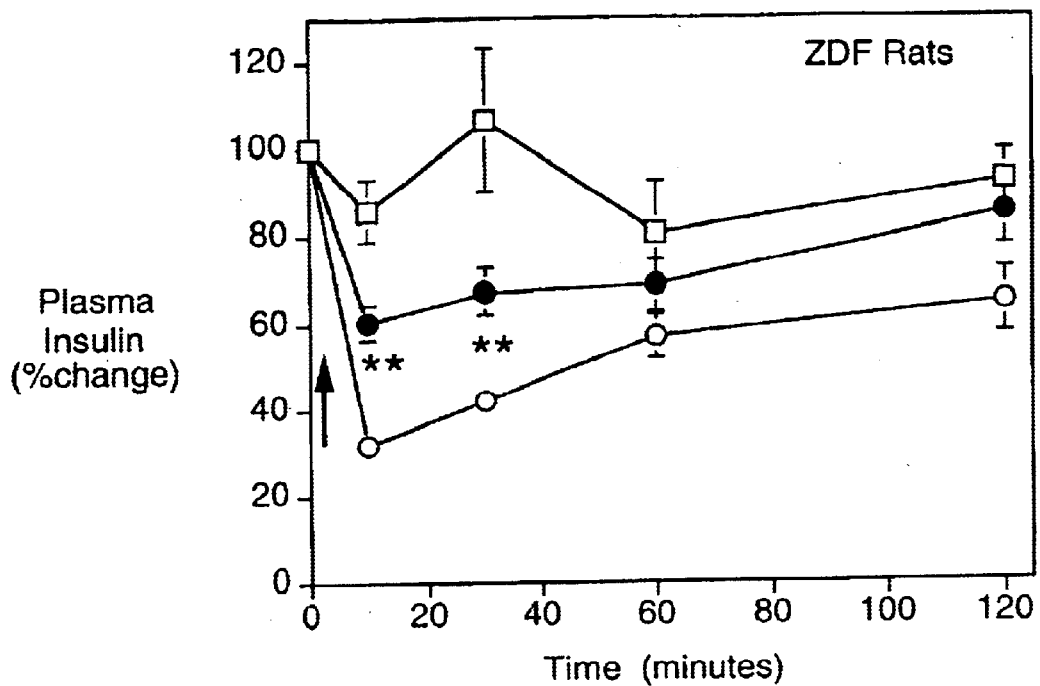
Figure 10B:
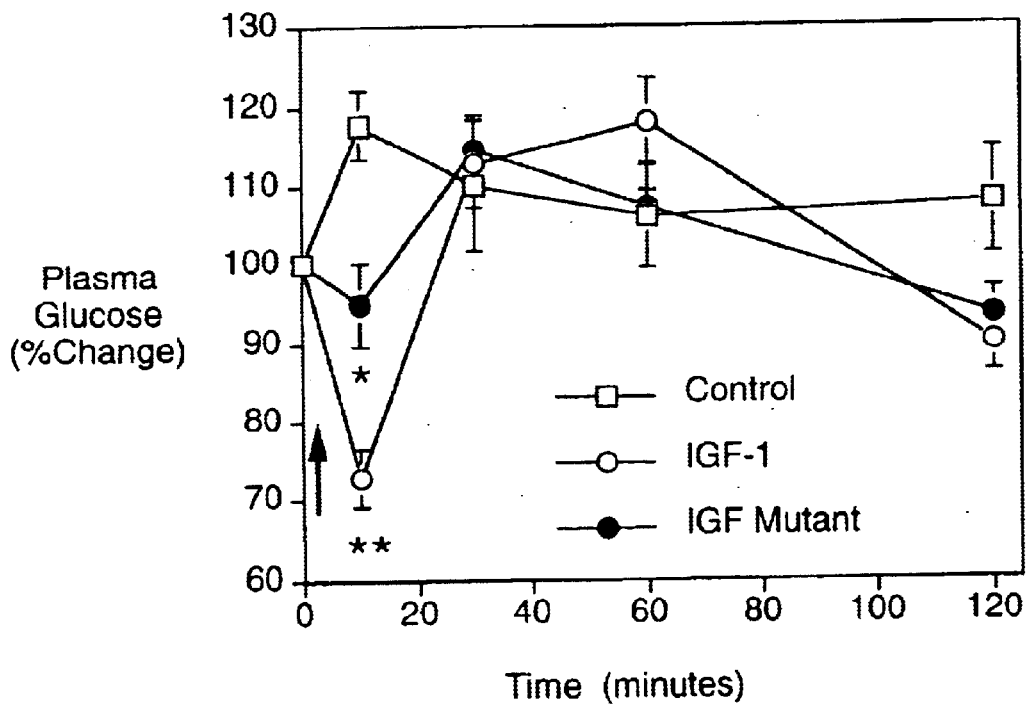
Figure 11A:
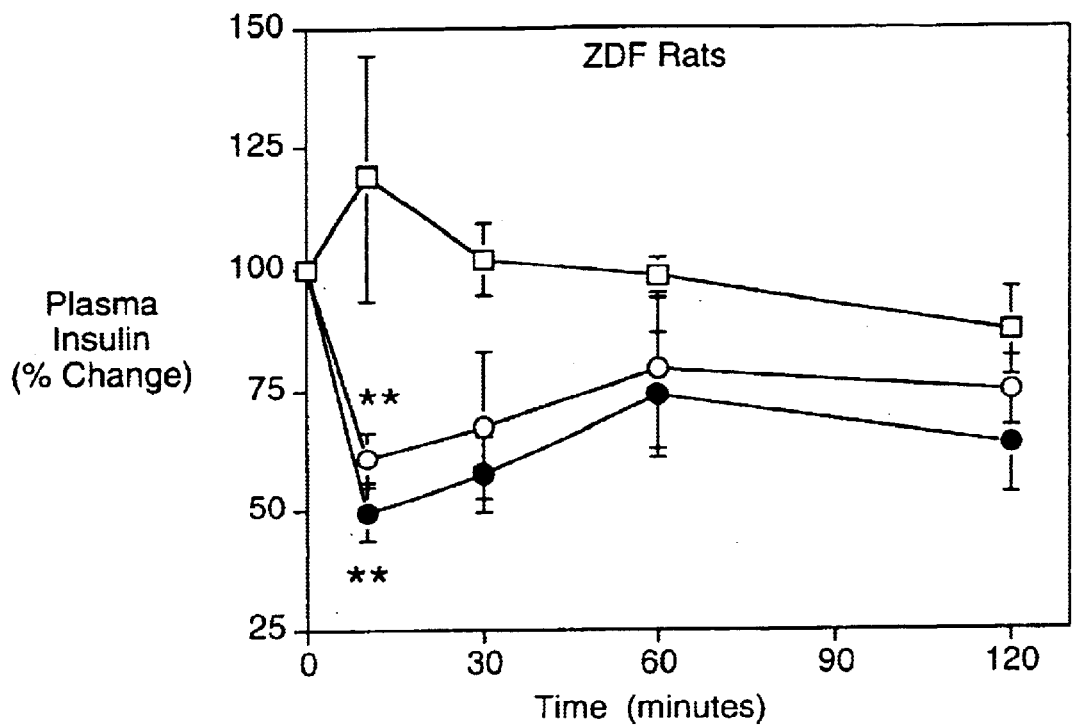
Figure 11B:
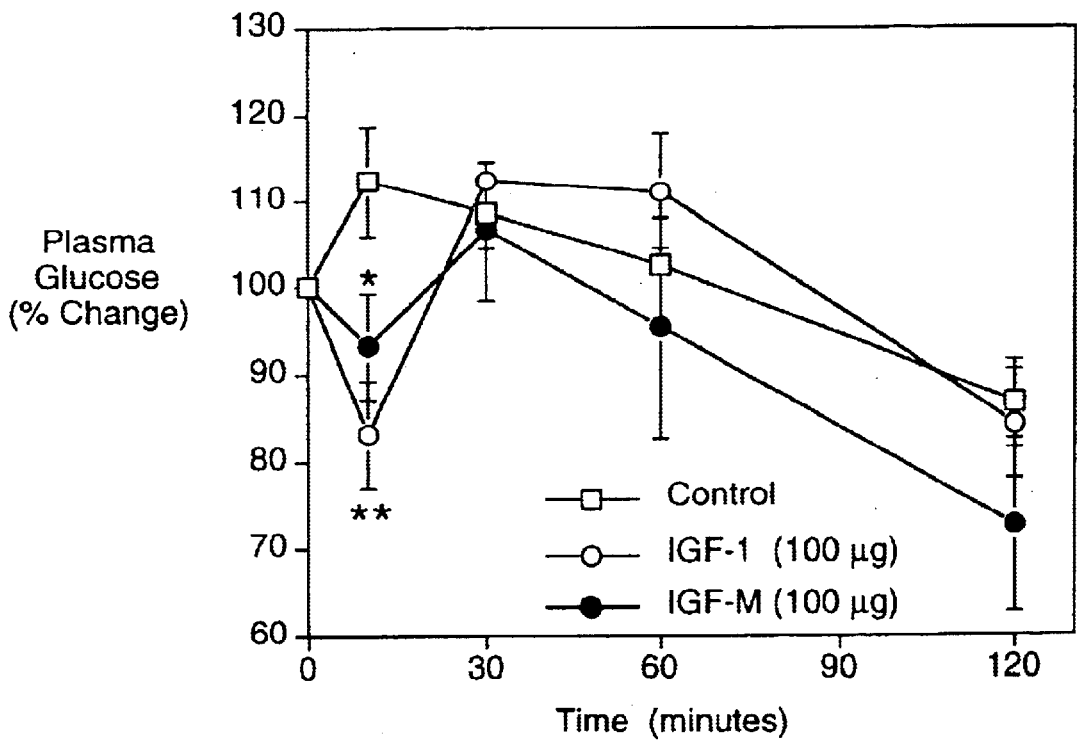
Figure 12:
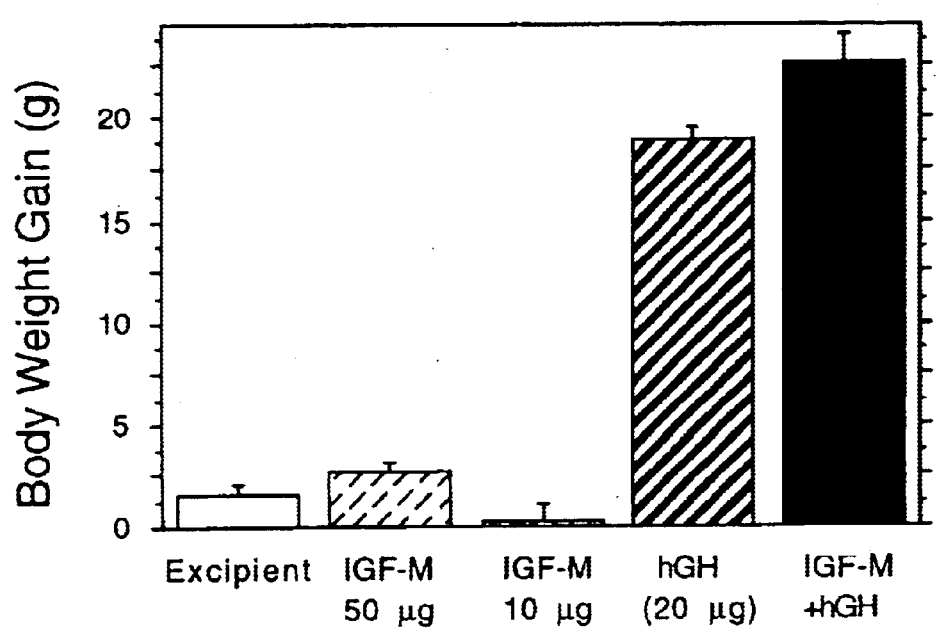
Figure 13A:
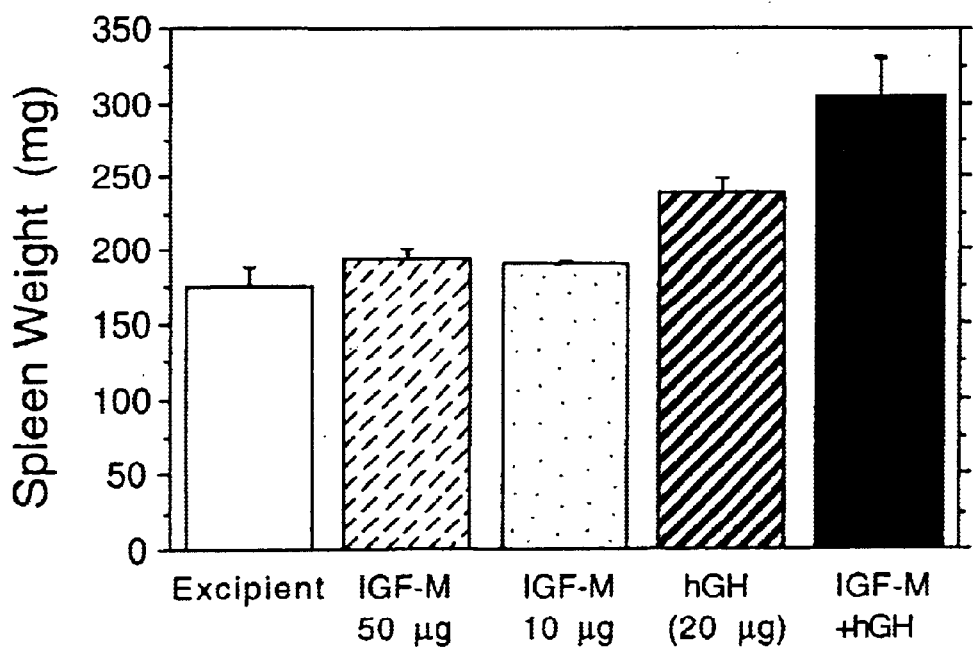
Figure 13B:
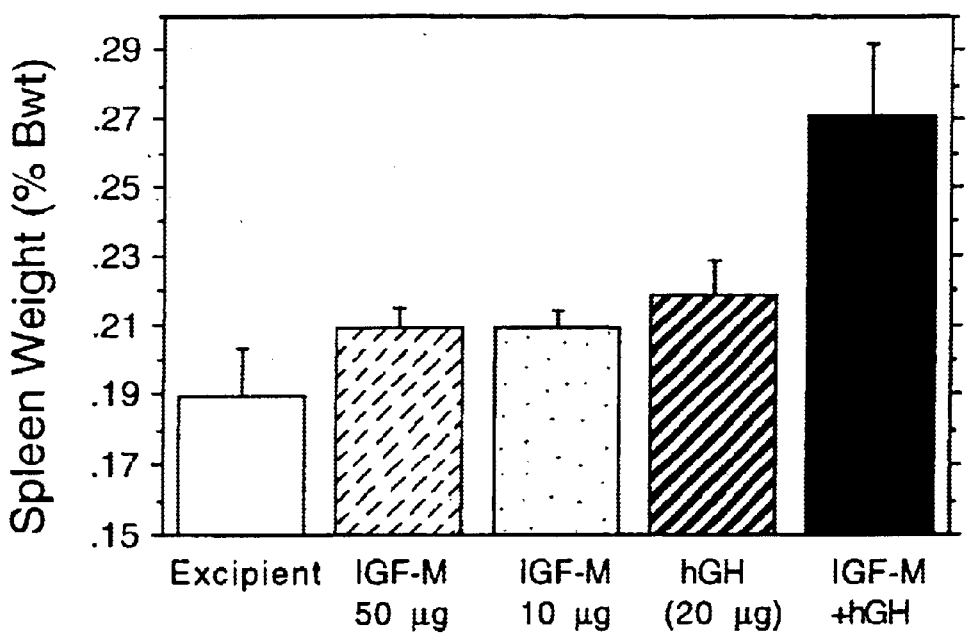
Figure 14A:
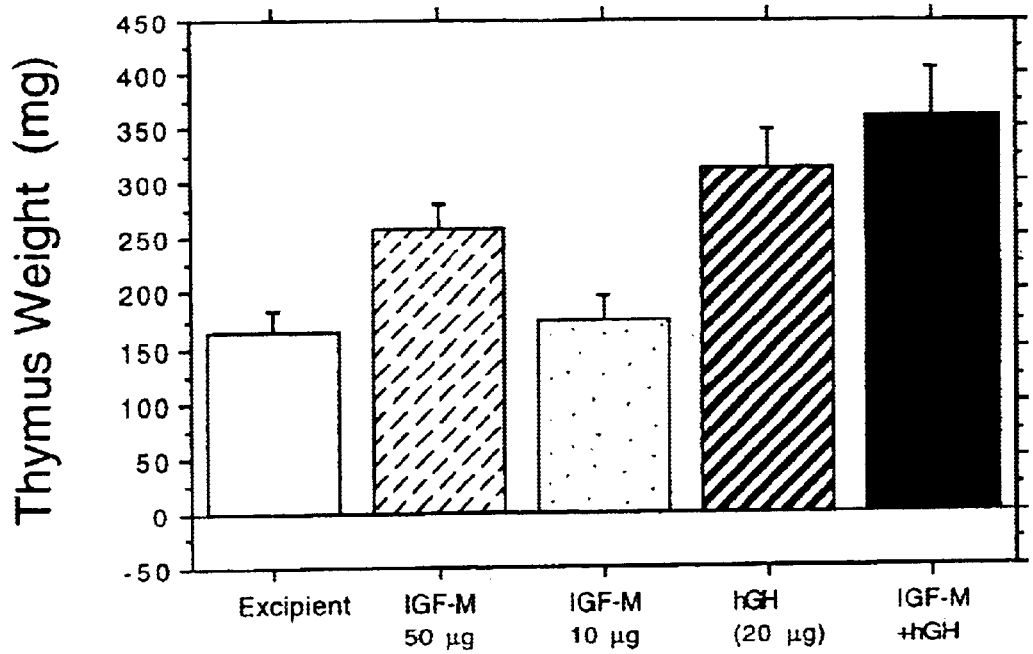
Figure 14B:
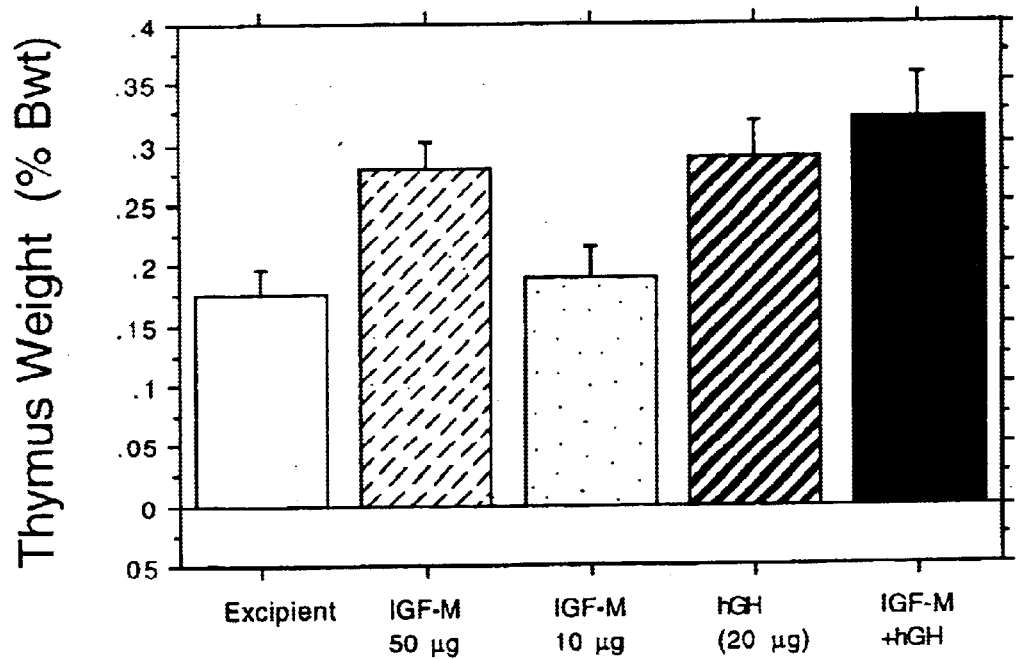
Figure 15A:
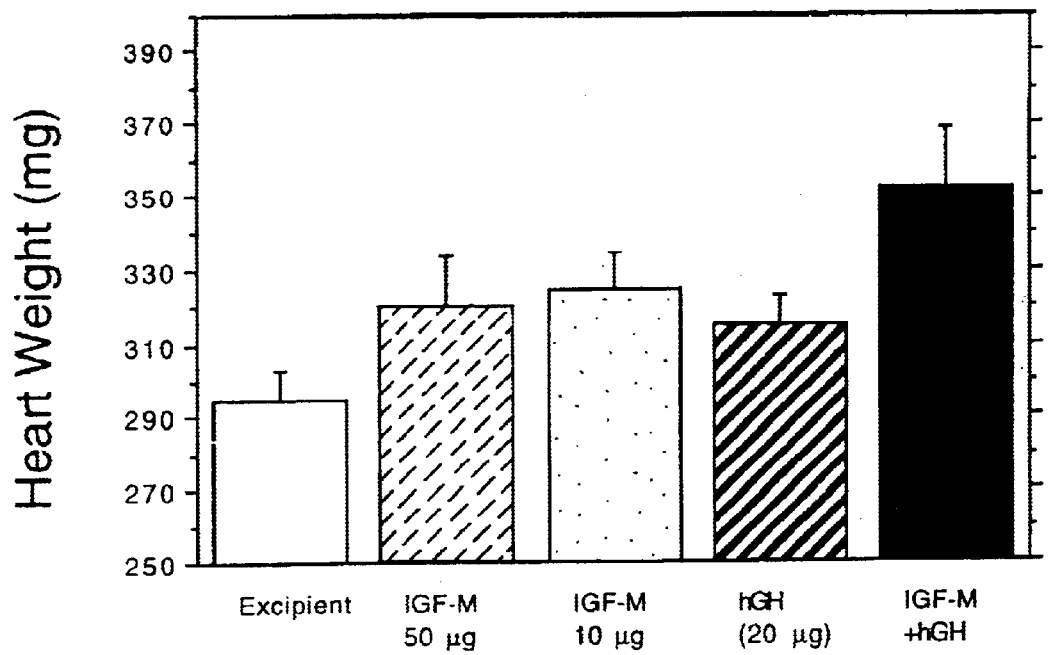
Figure 15B:
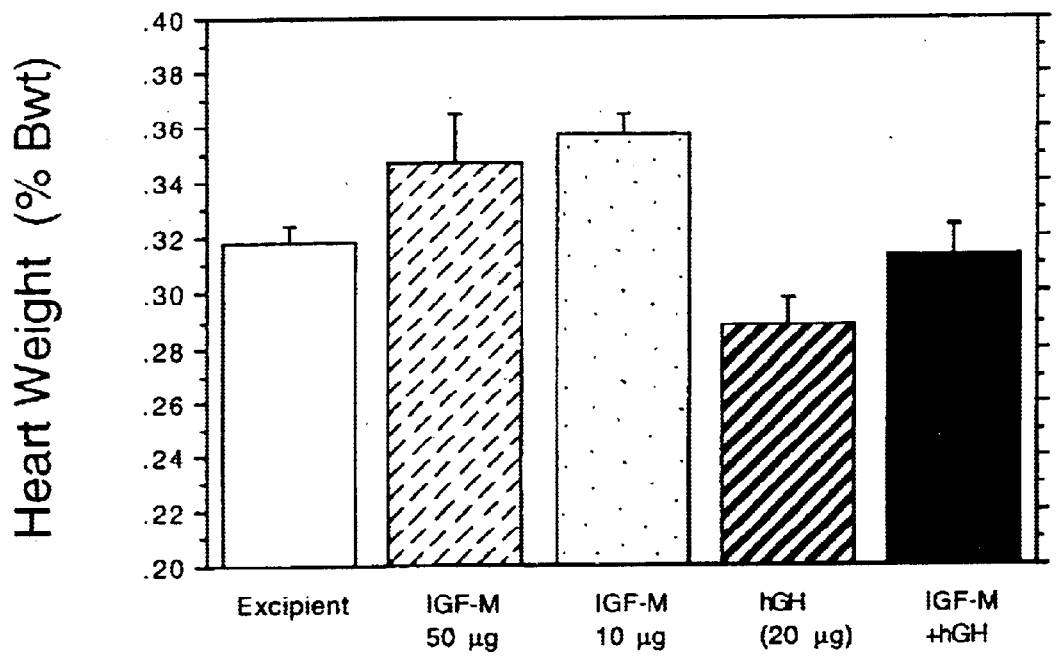
Figure 16:
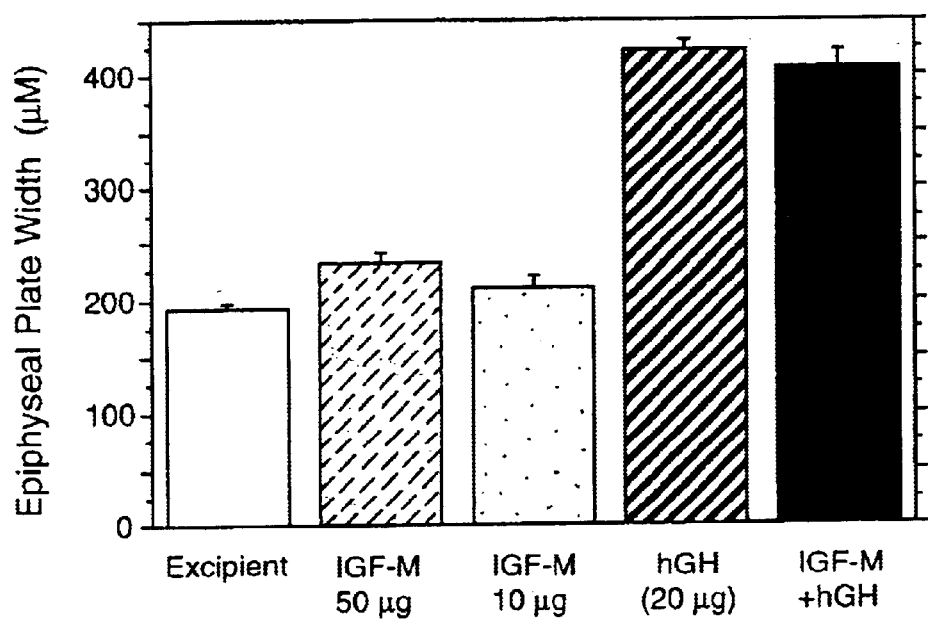
Figure 17A:
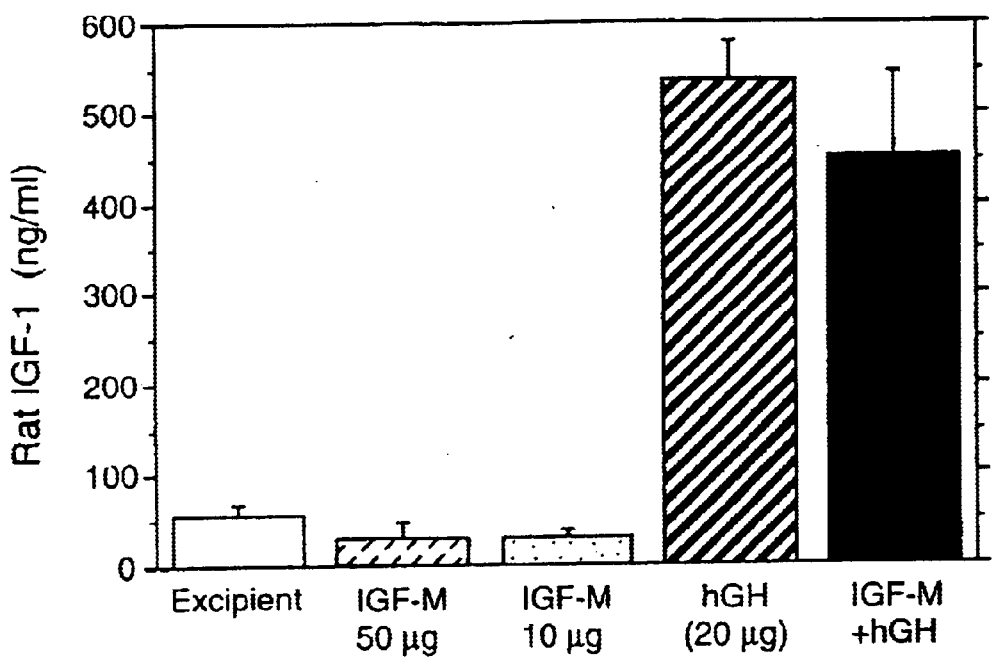
Figure 17B:
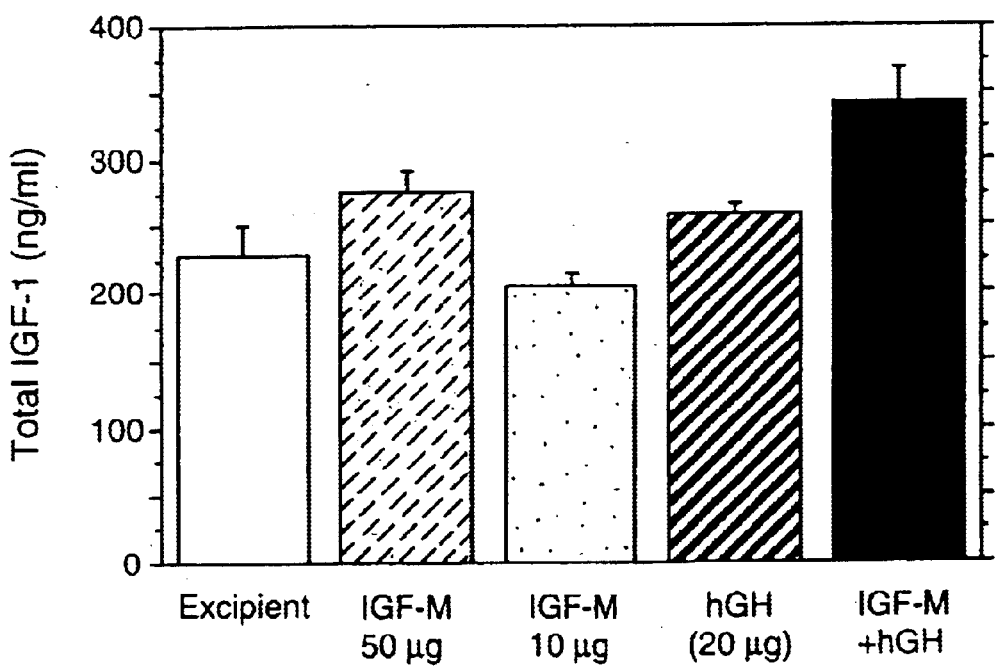
Figure 18:
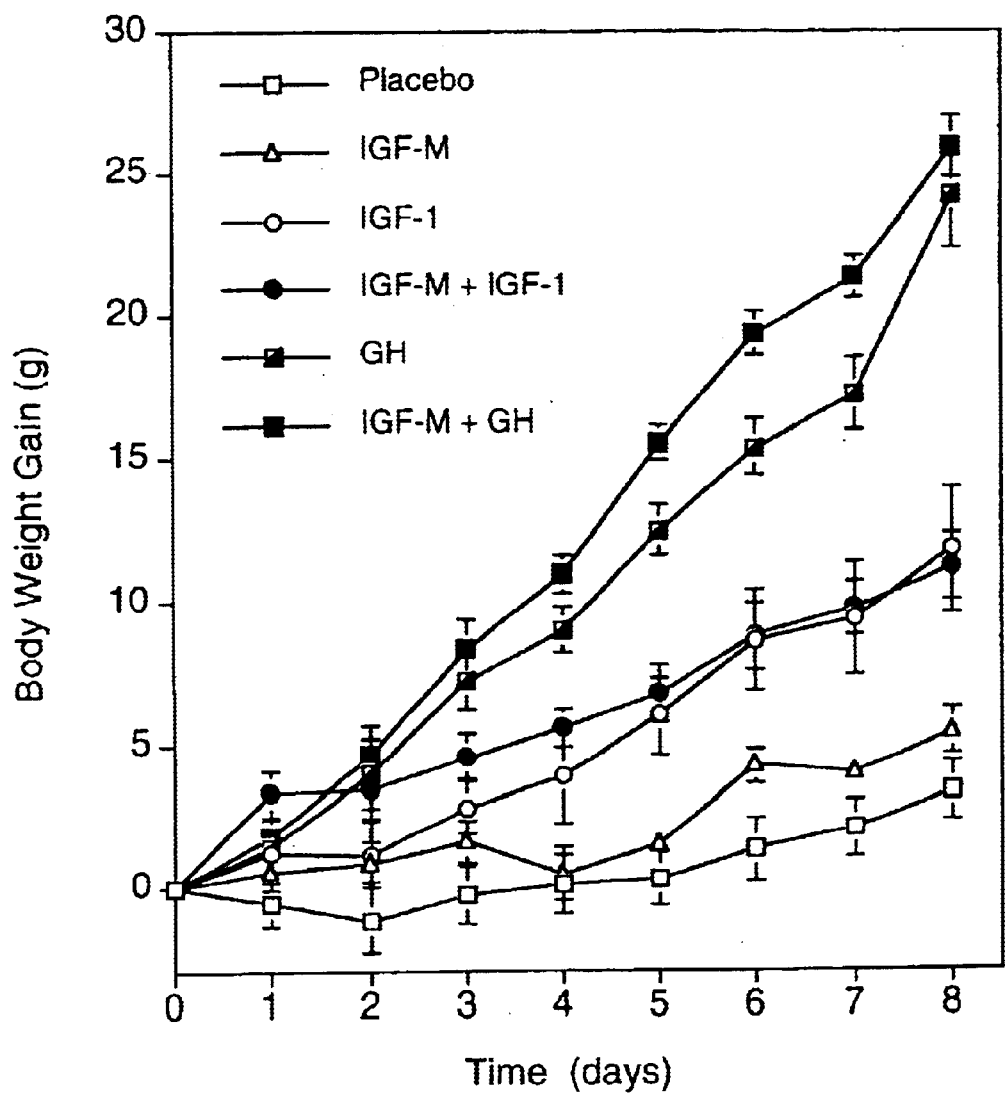
Figure 19A:
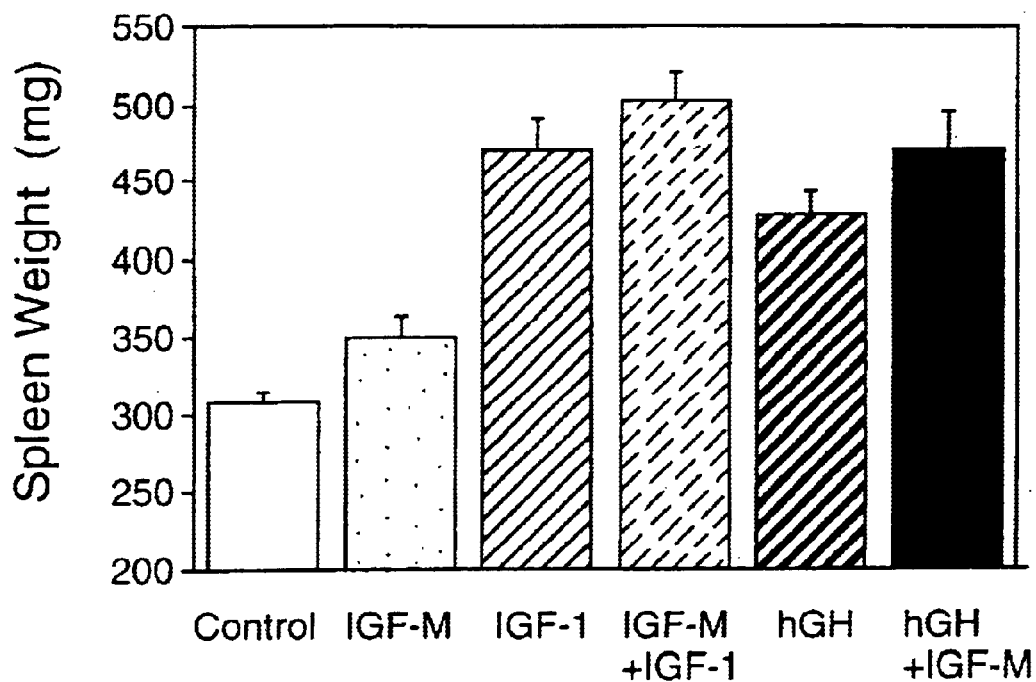
Figure 19B:
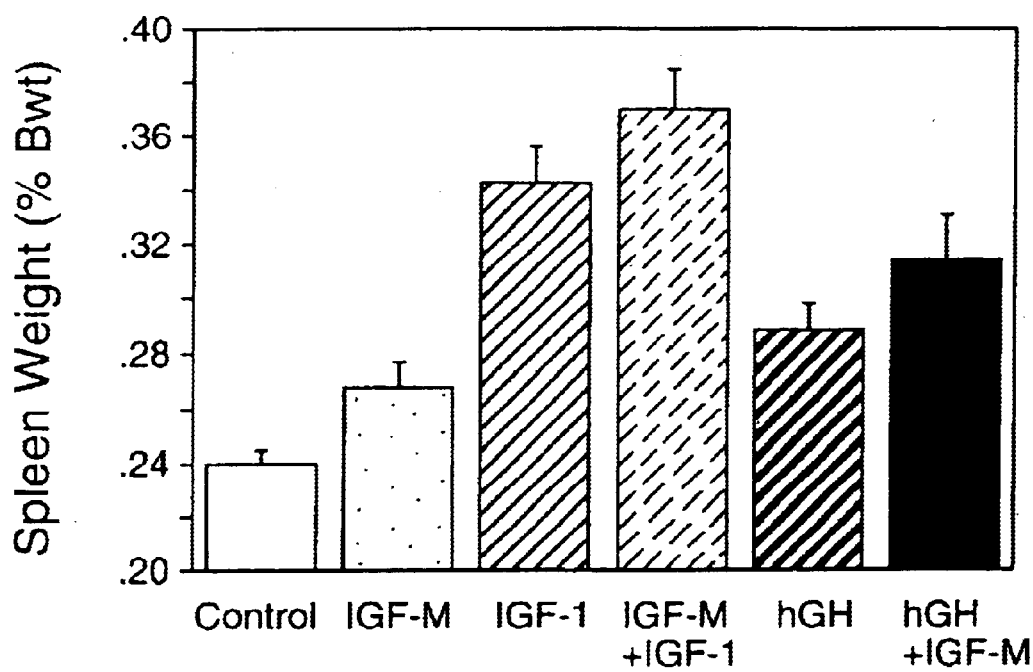
Figure 20A:
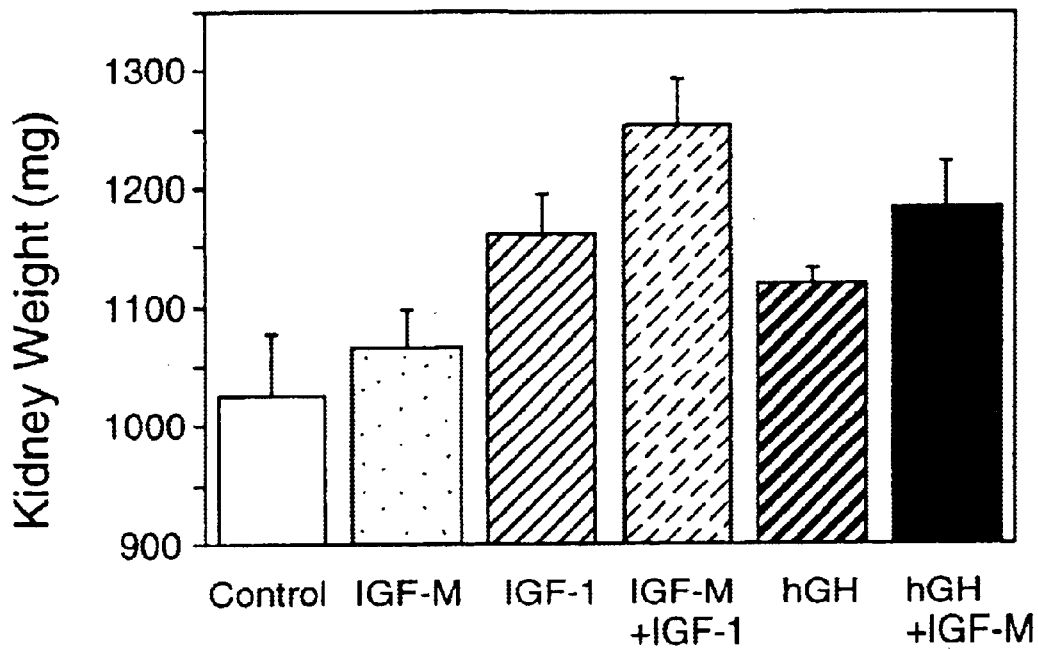
Figure 20B:
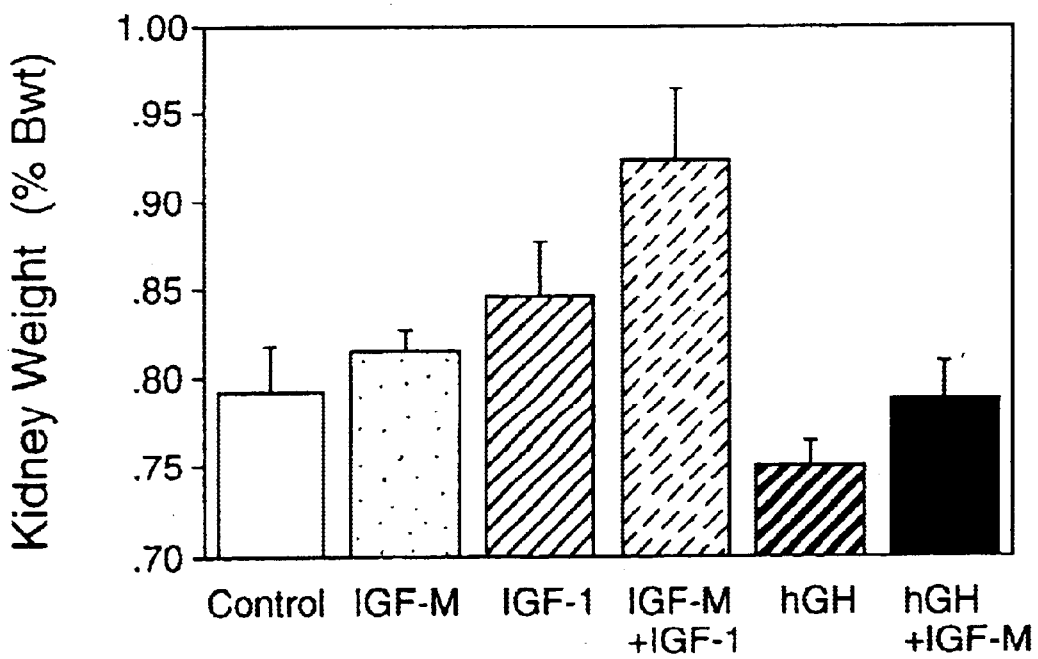
Figure 21A:
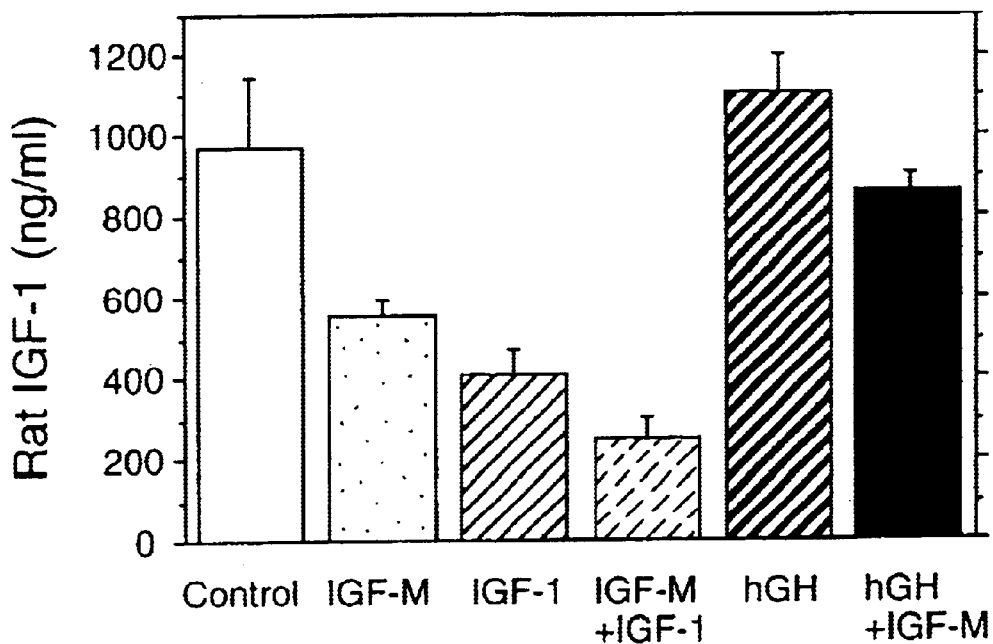
Figure 21B:
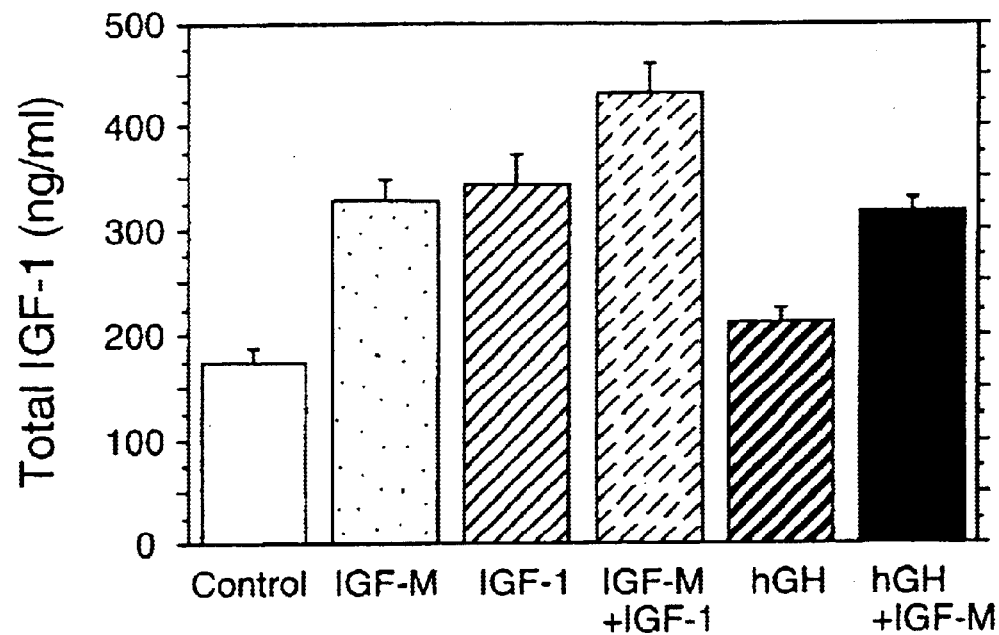
Figure 22A:
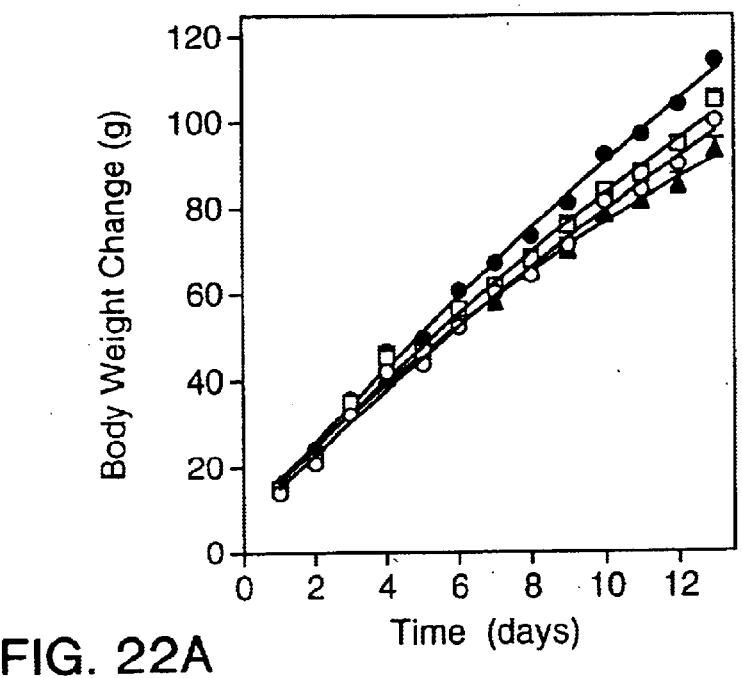
Figure 22B:
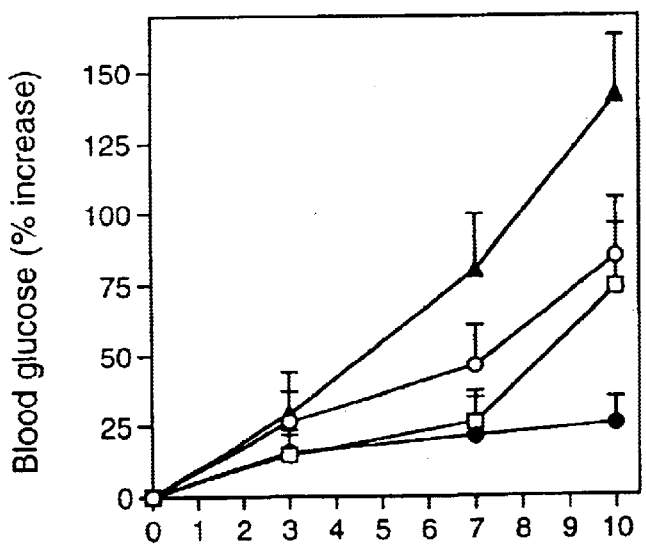
Figure 25:
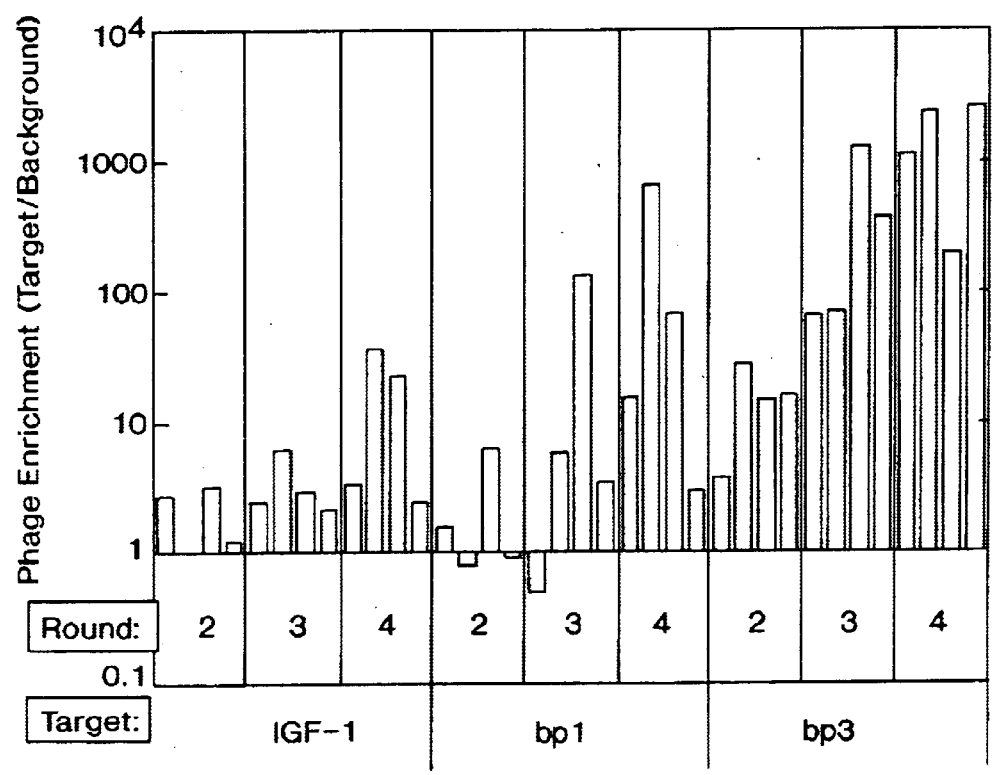
Figure 26:
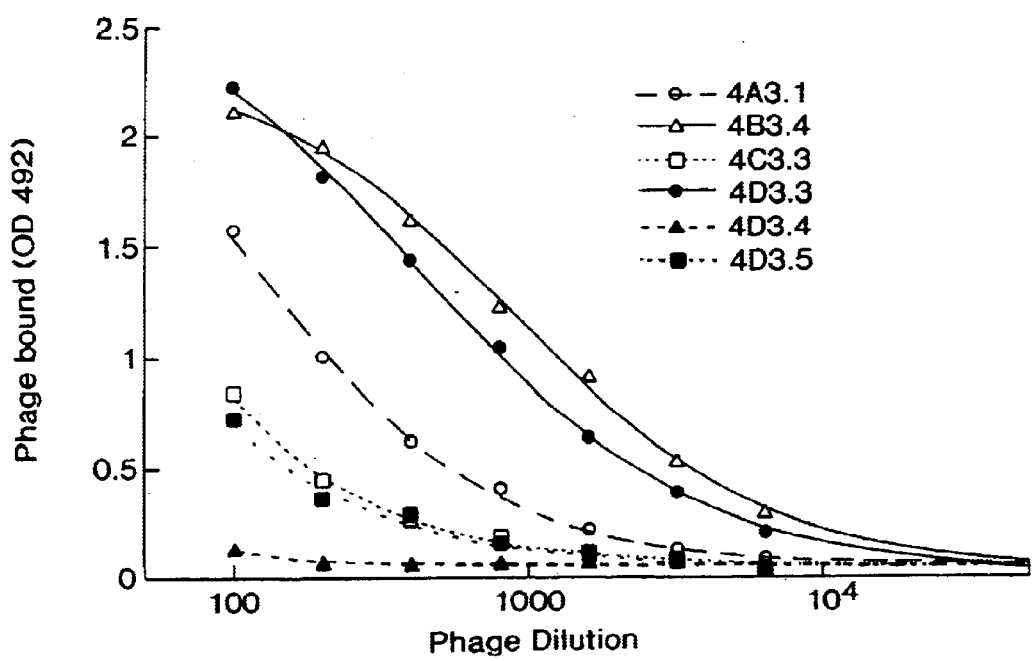
Figure 27:
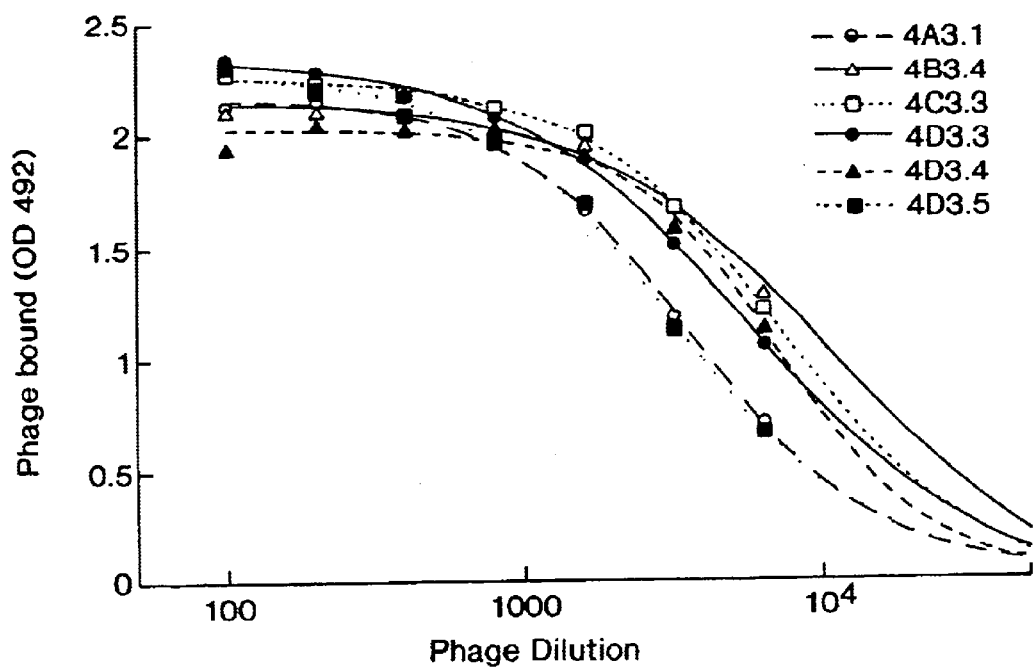
Figure 28:
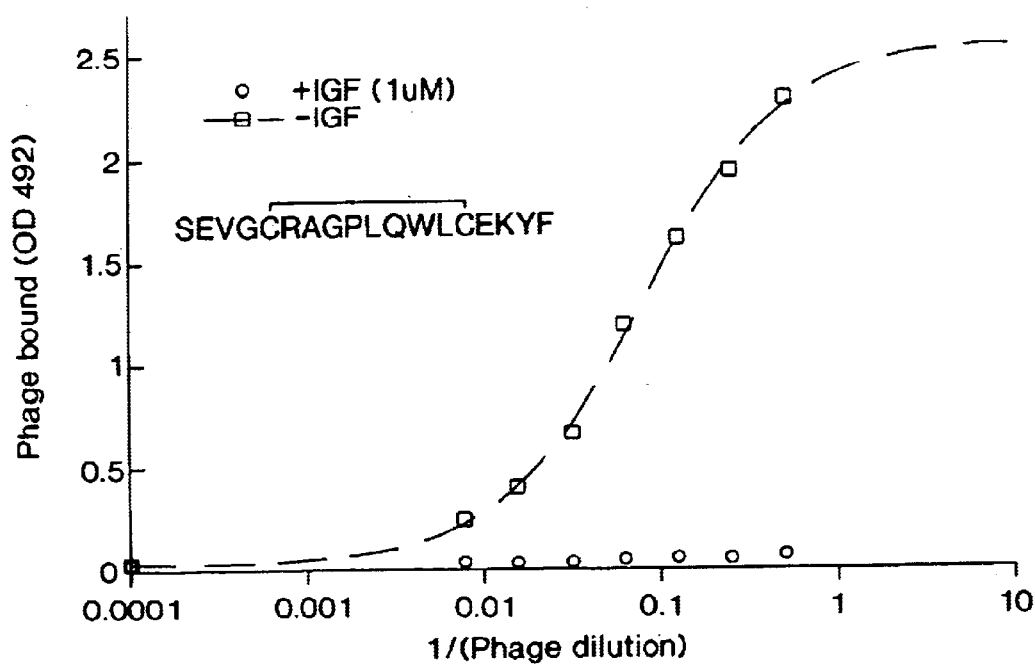
Figure 29:
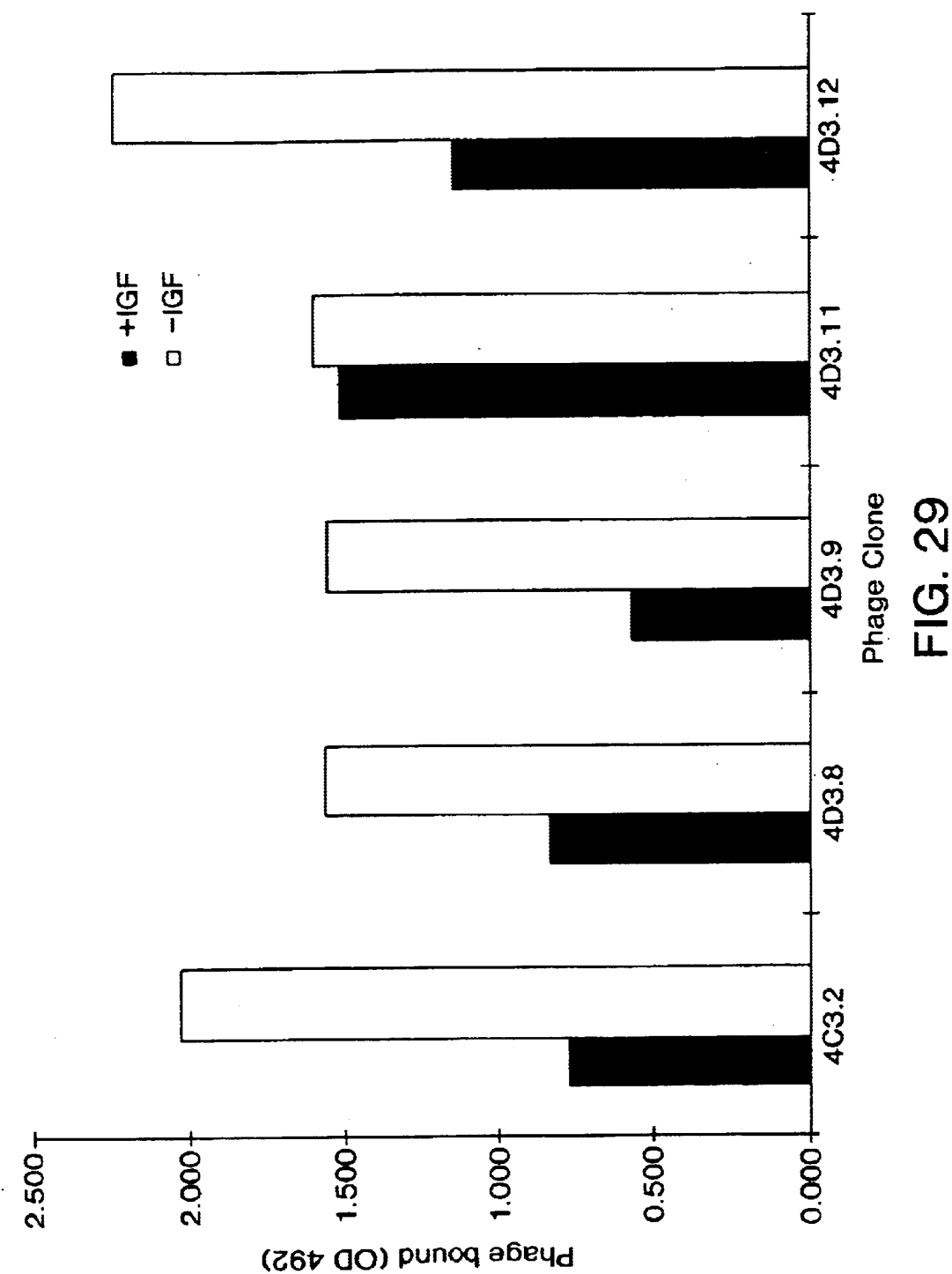
Figure 30:
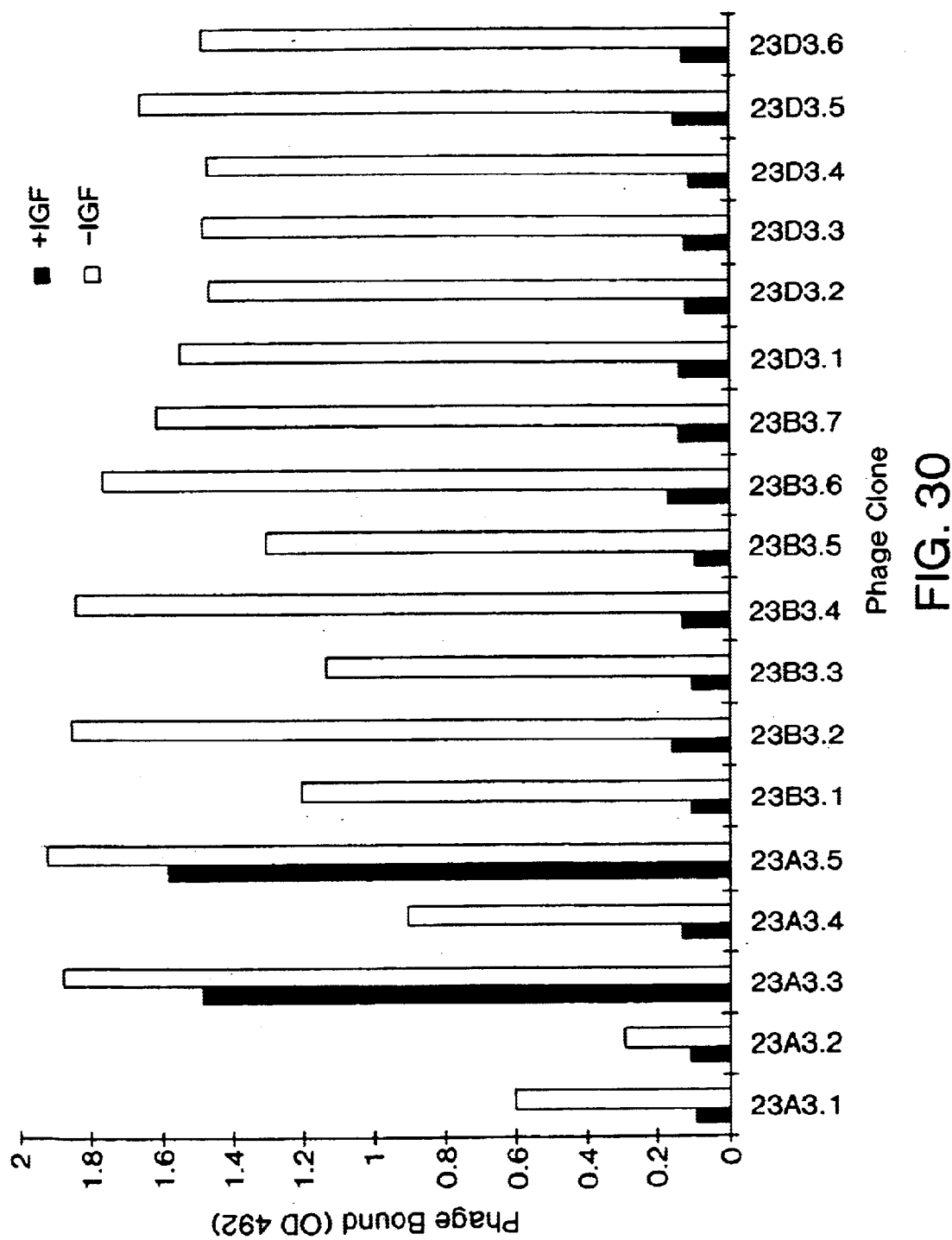
Figure 31:
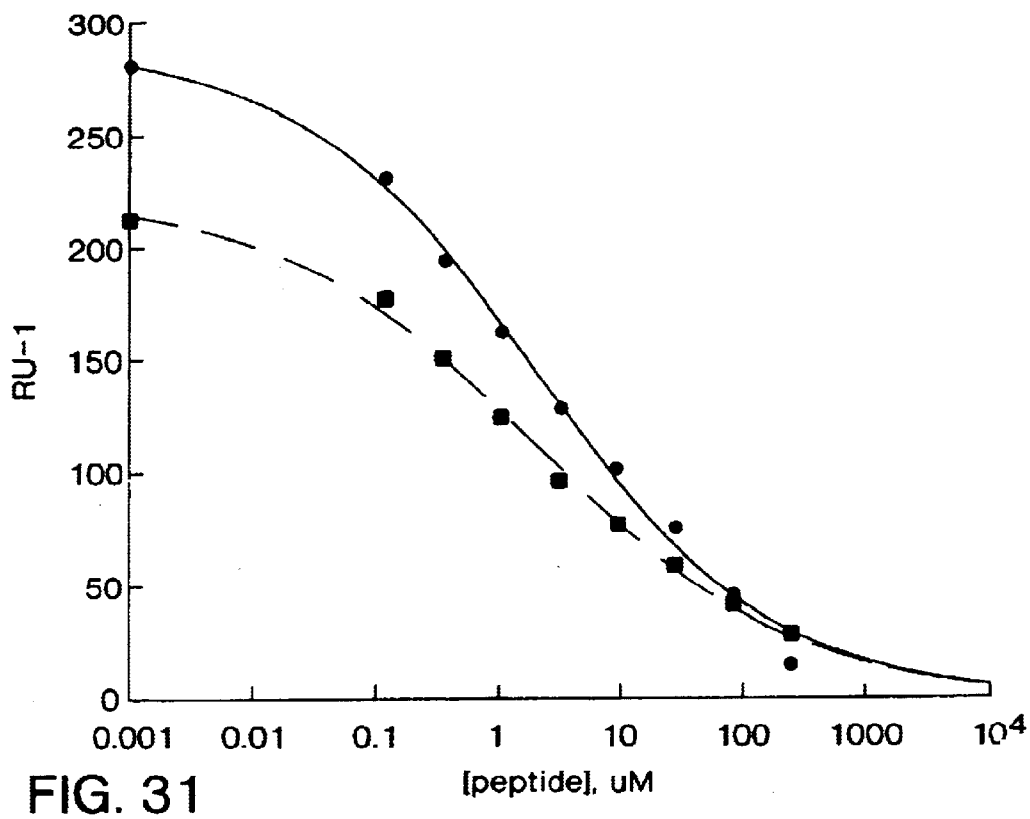
Figure 32:
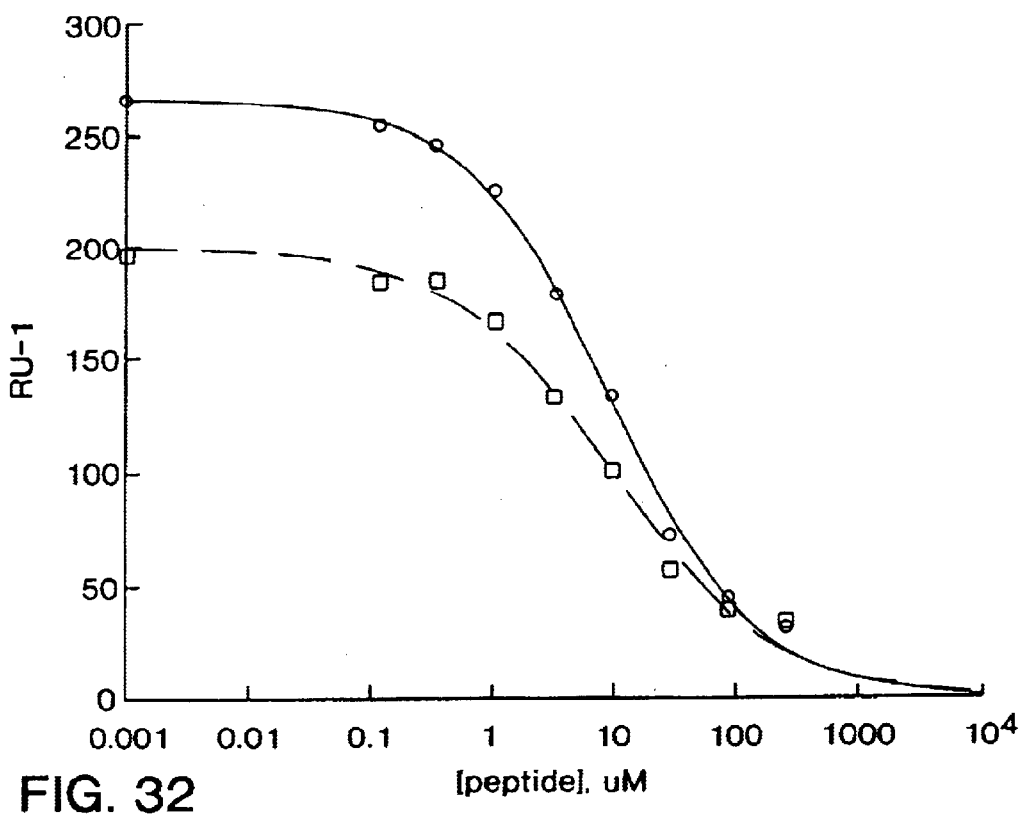
Figure 33:
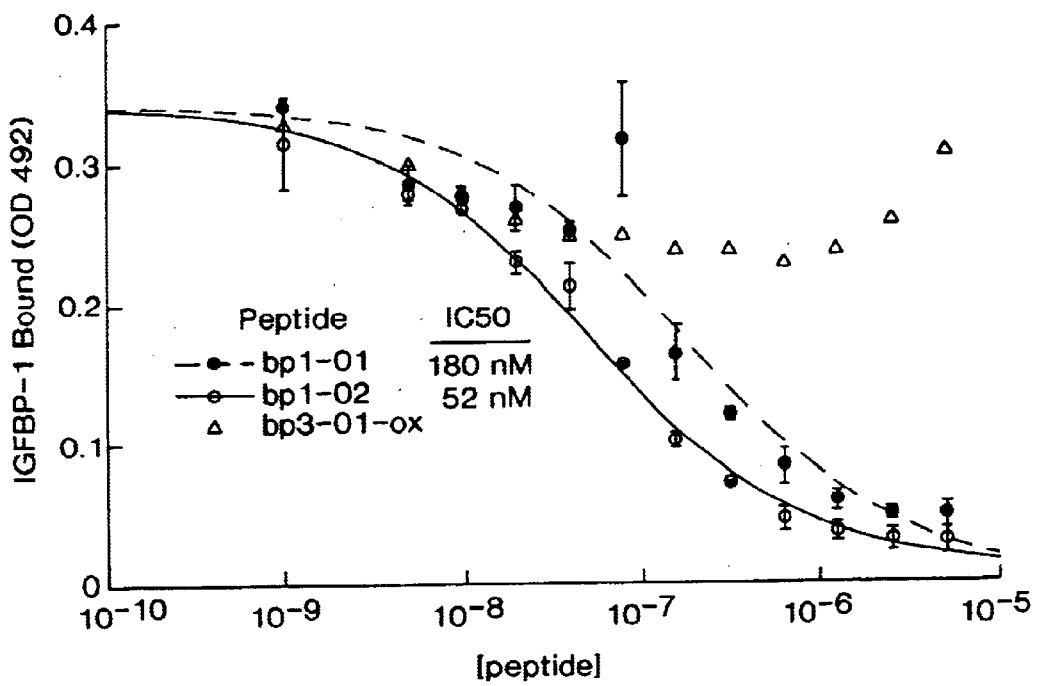
Figure 34:
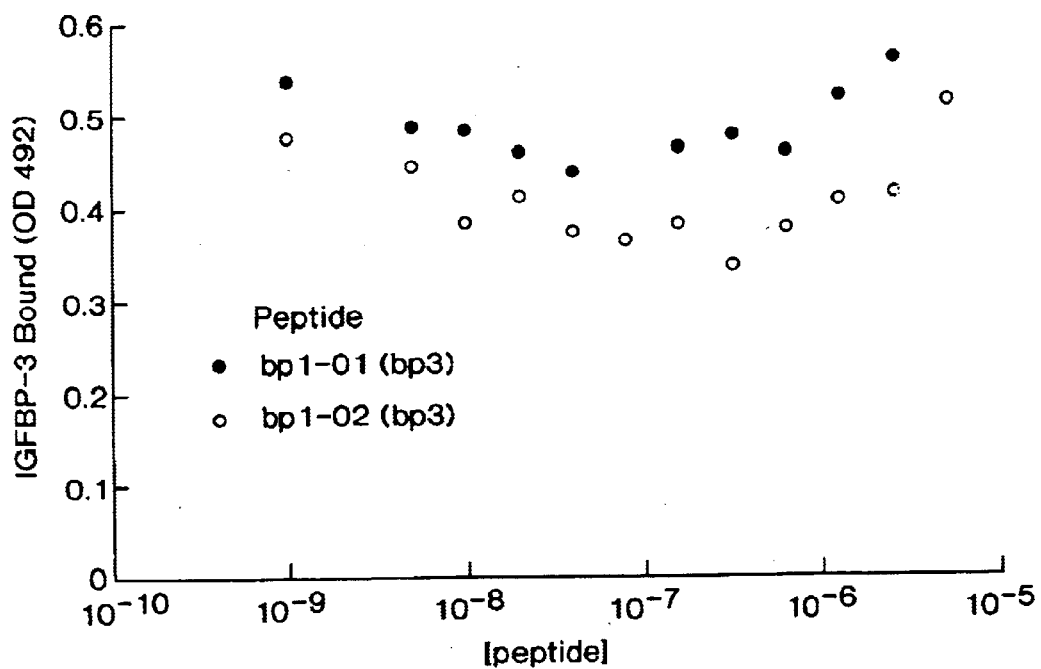
Figure 35:
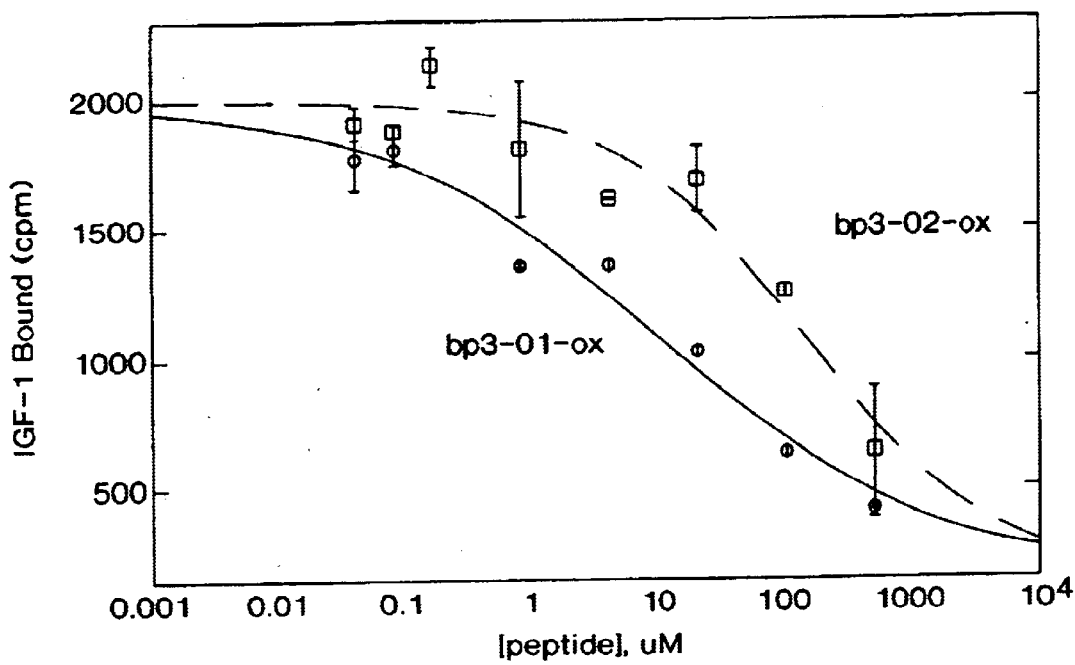
Figure 36:
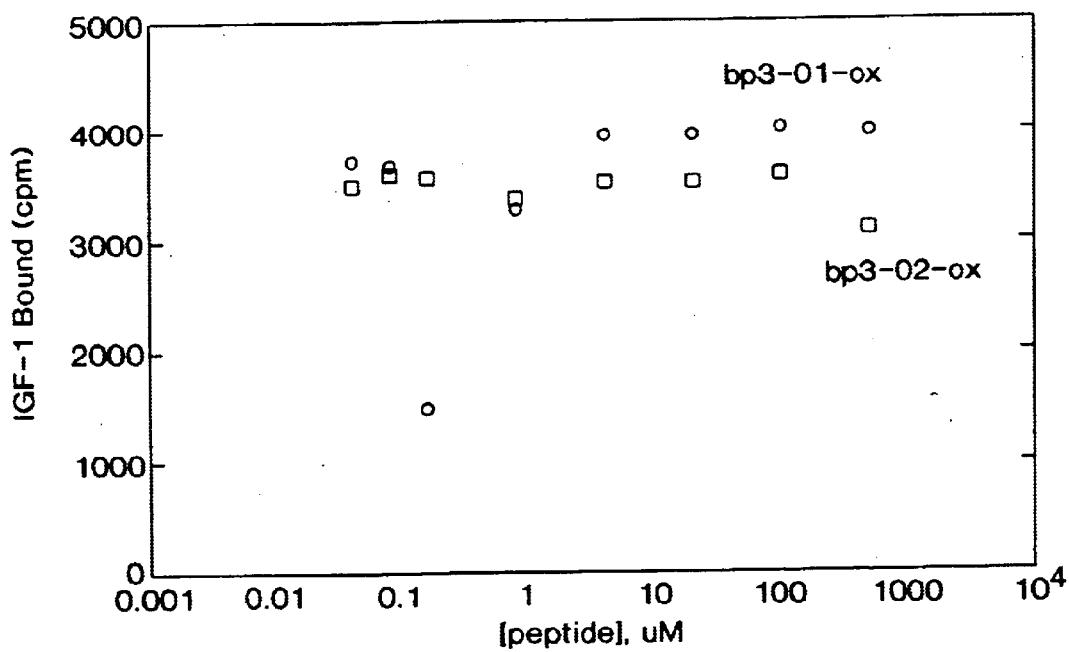
Figure 37A:
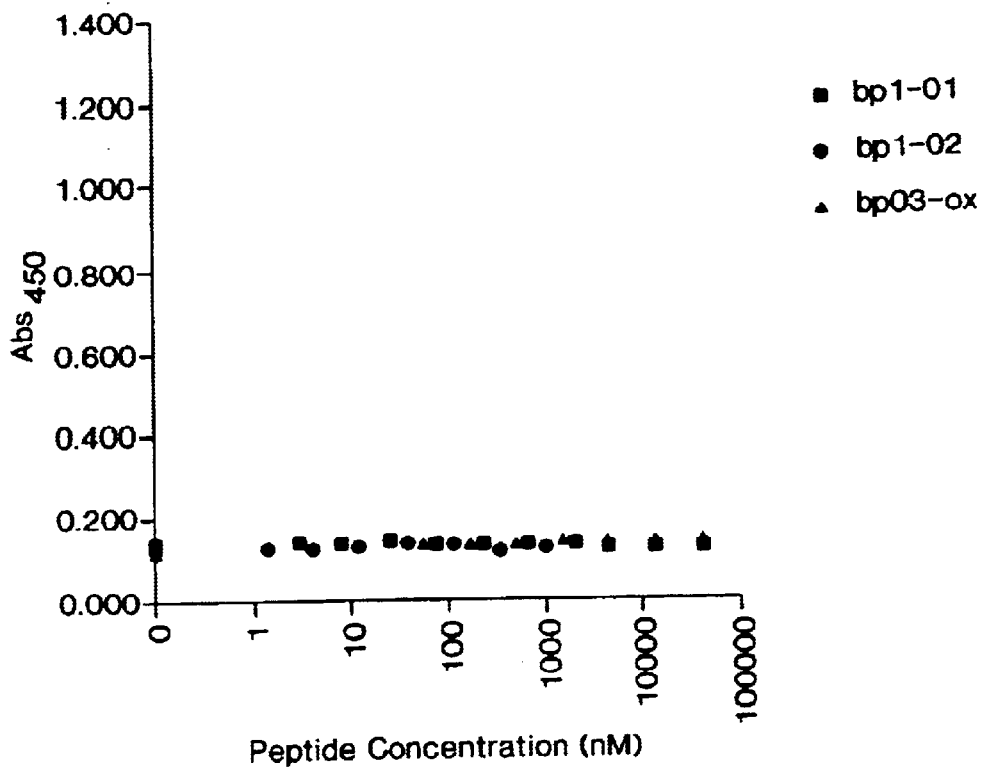
Figure 37B:
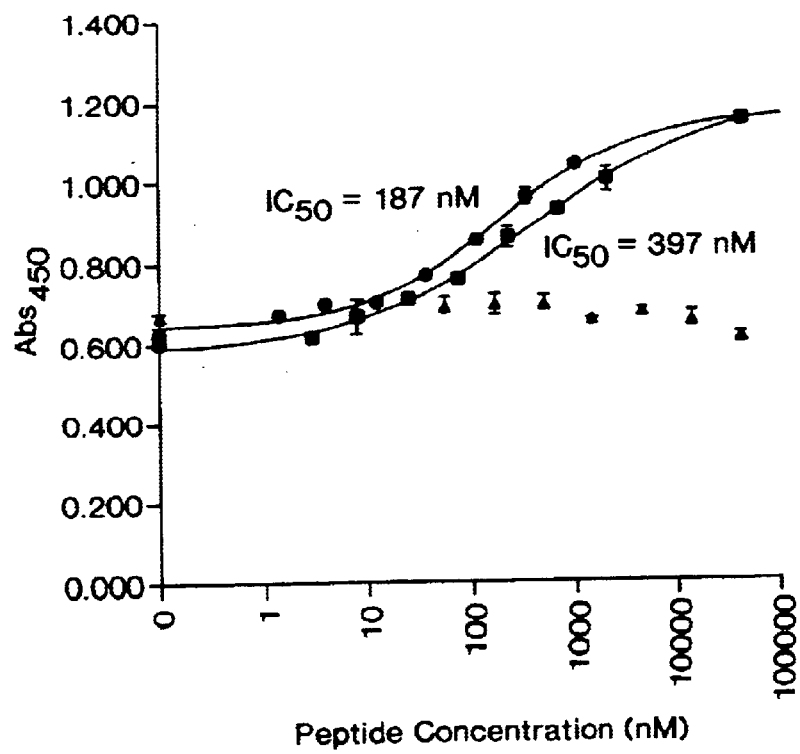
Figure 37C:
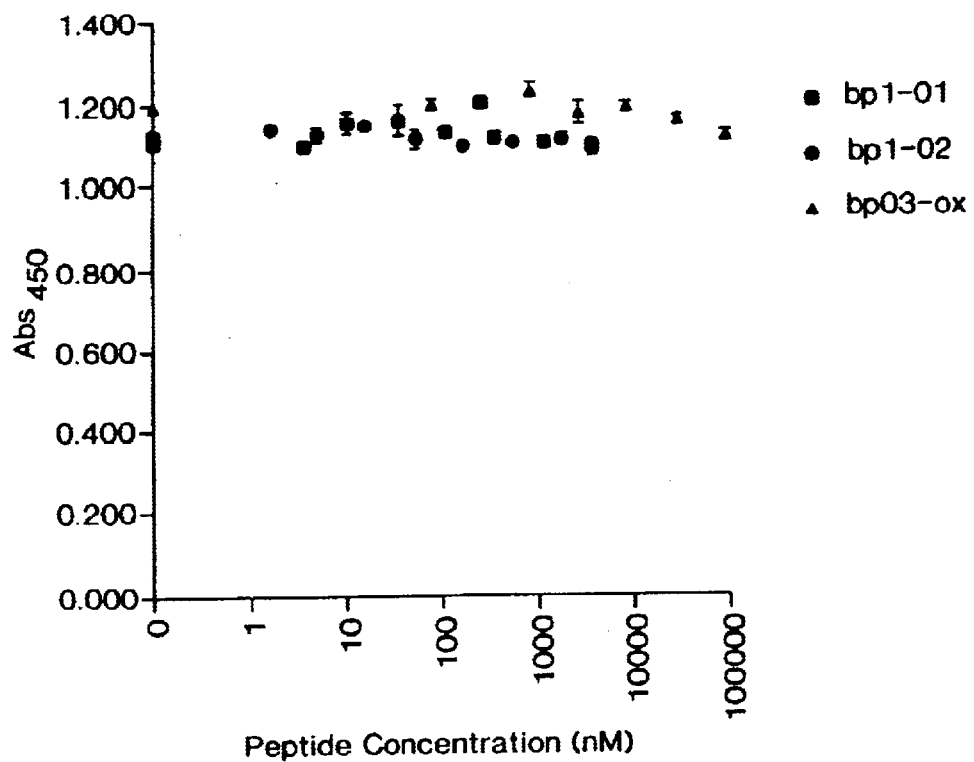
Figure 37D:
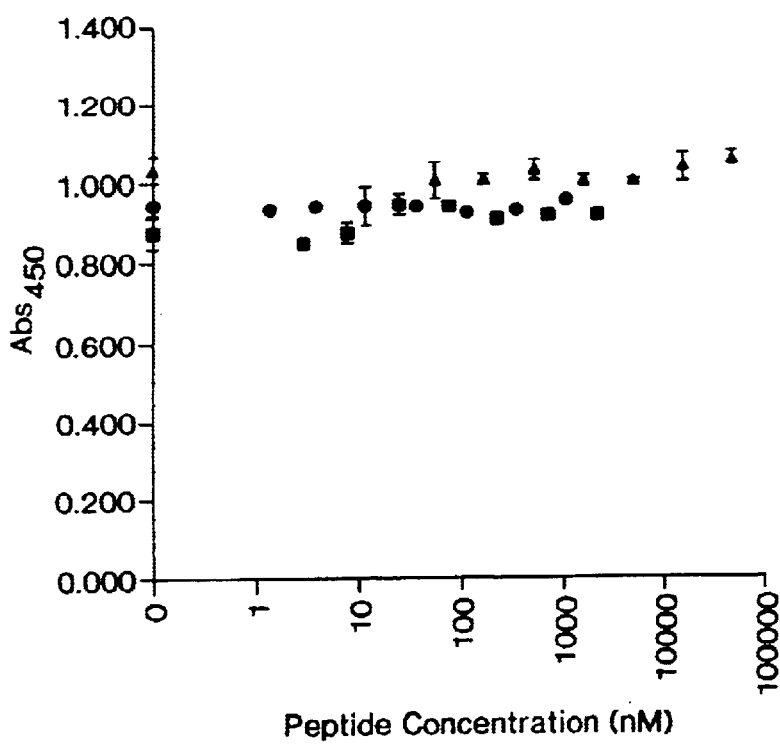
Figure 38:
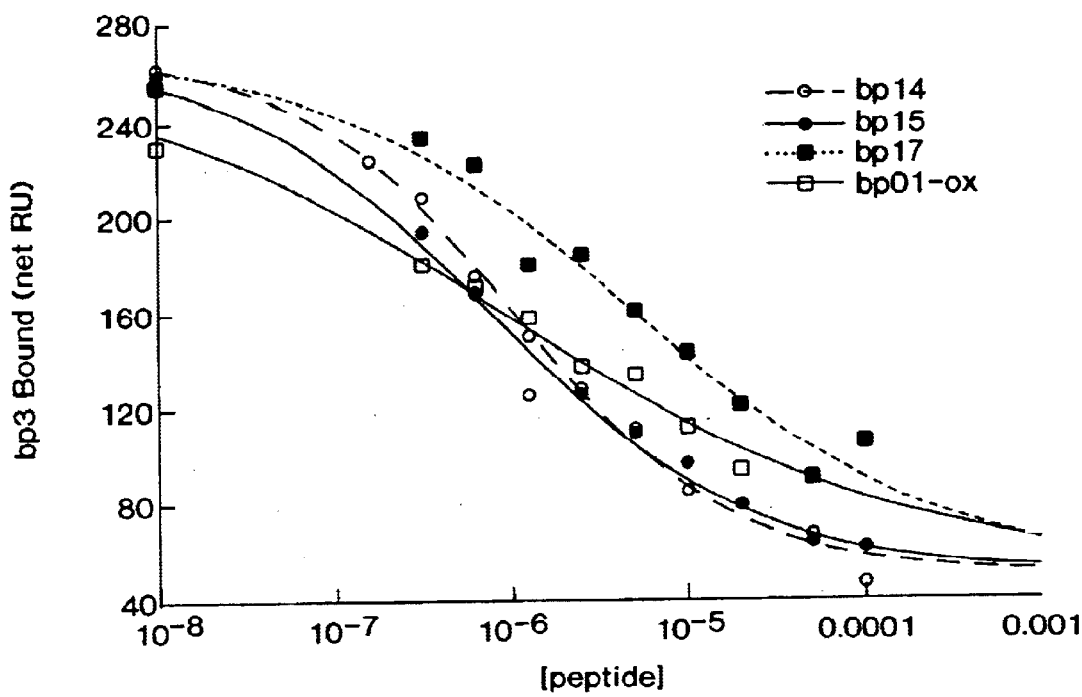
Figure 39:
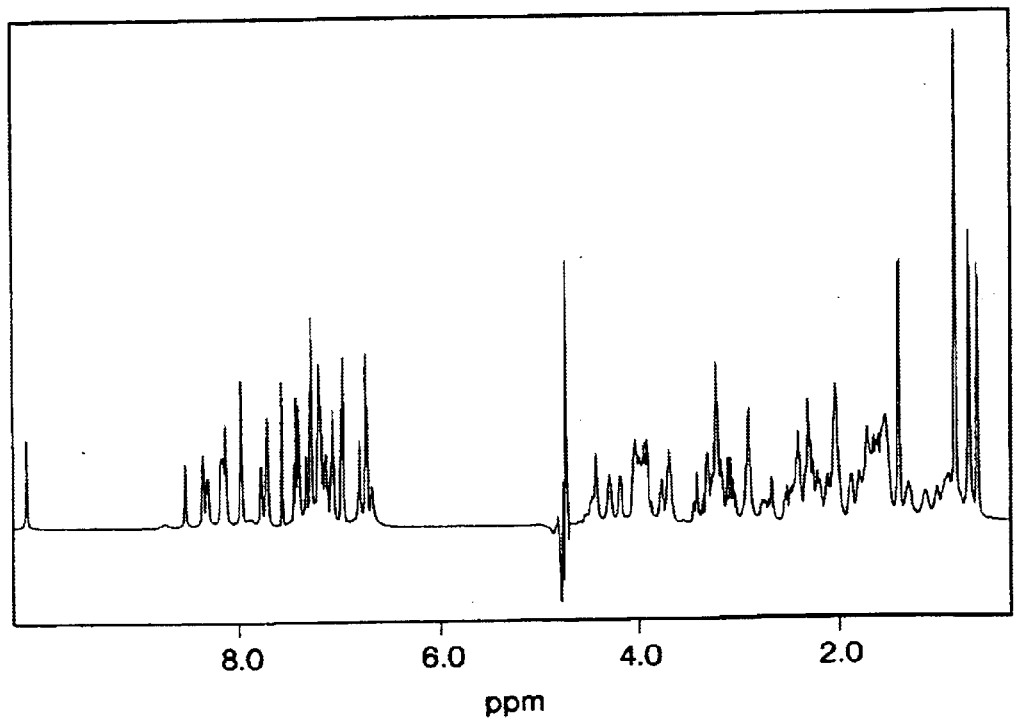
Figure 40A:
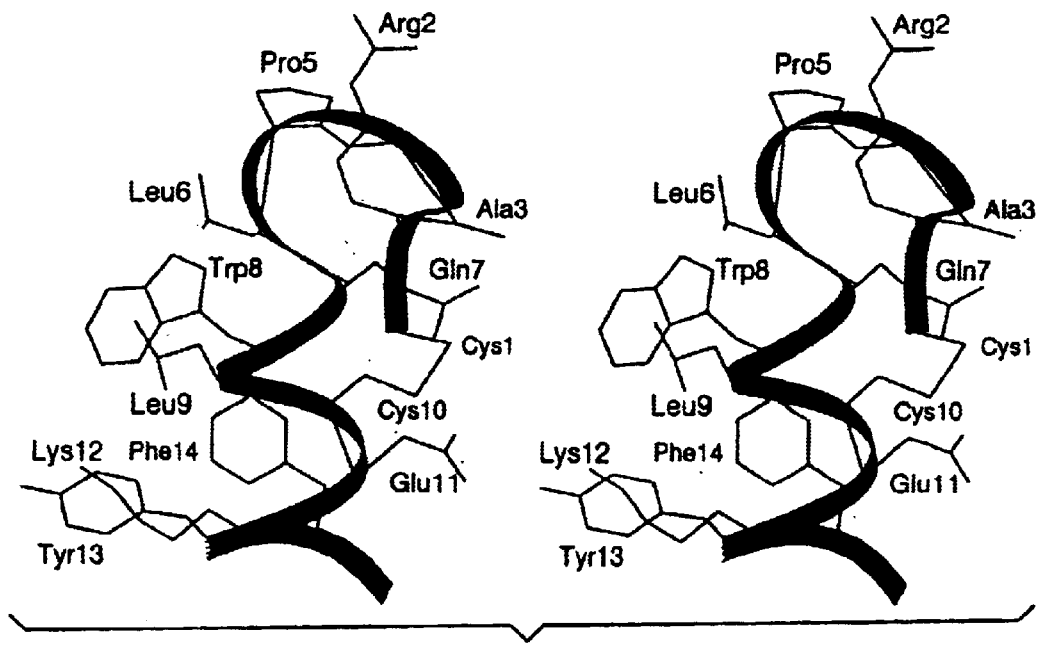
Figure 40B:
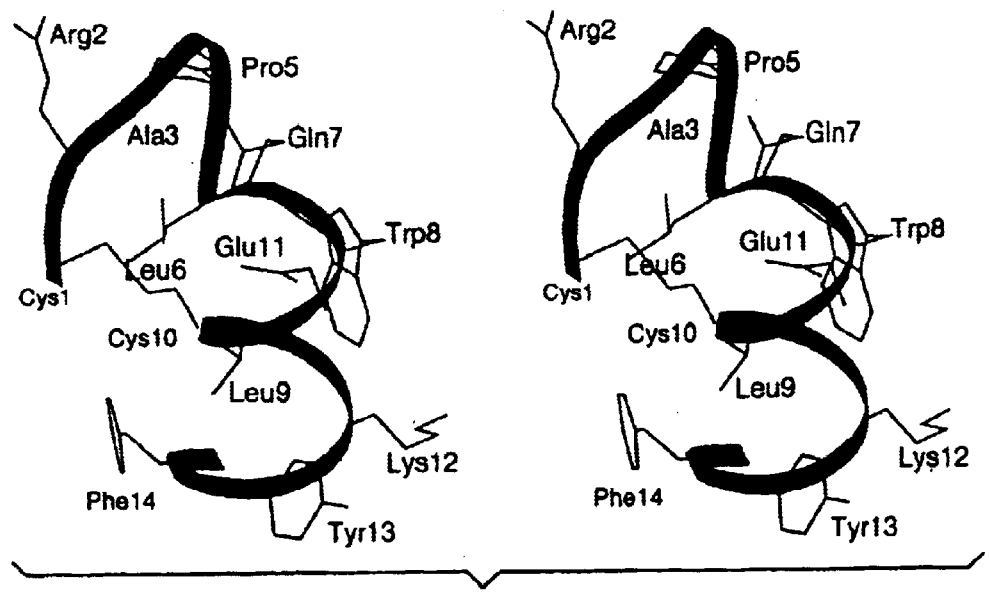
Figure 41:
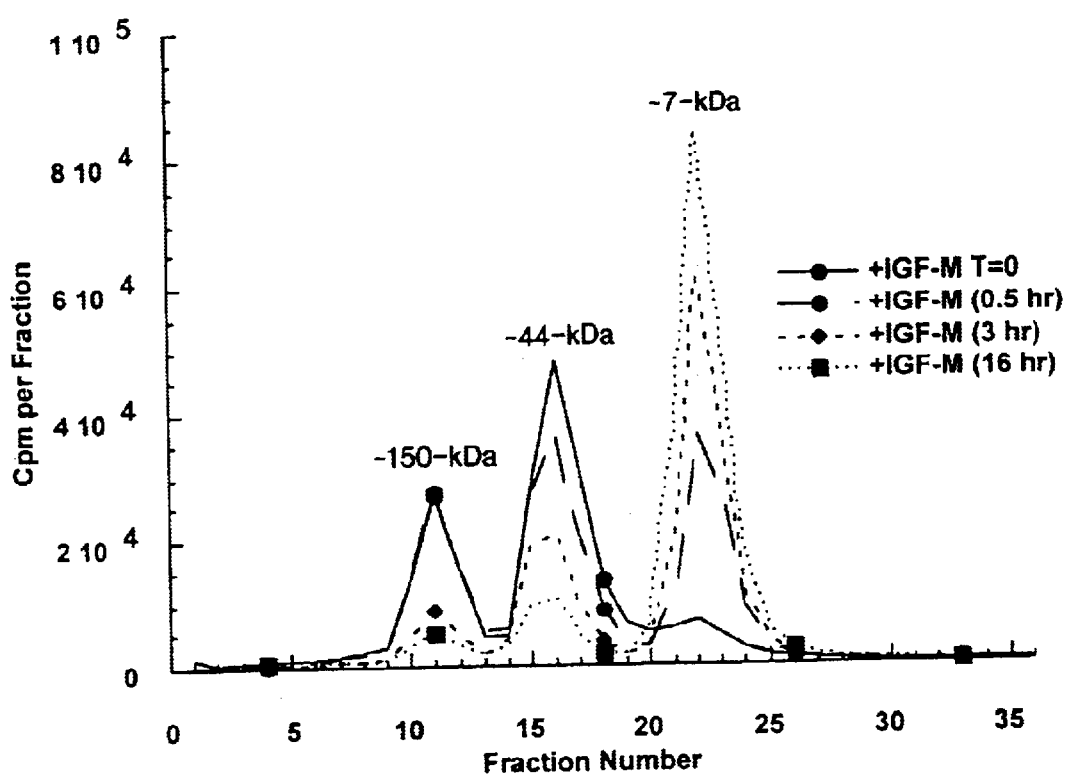
Figure 42:
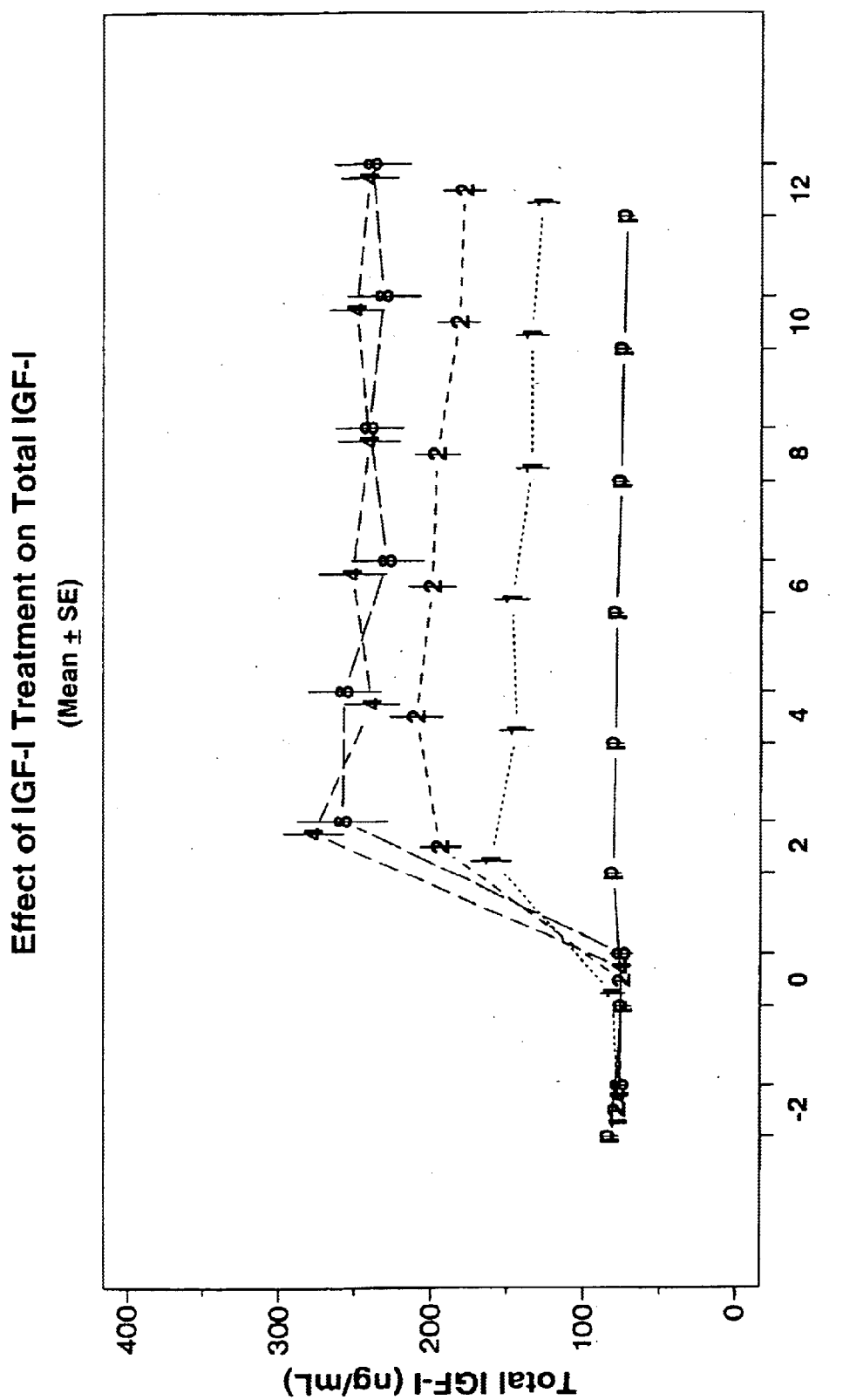
Figure 43:
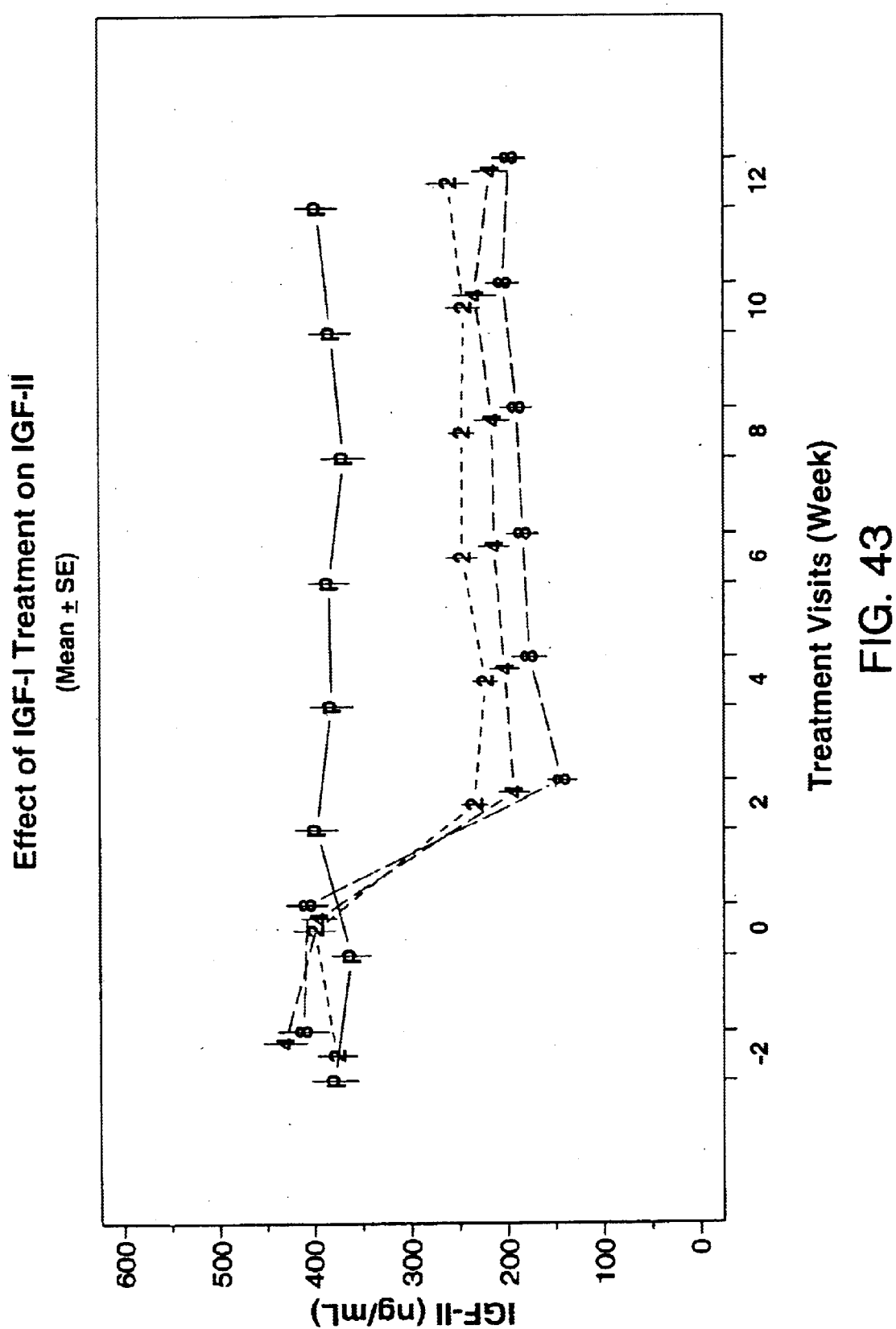

The peptide bp1-625 fraction was lyophilized and resuspended in 100 mM HEPES buffer, pH 7.2. Inhibition experiments were carried out in a BIAcorem assay as previously described, except that limiting amounts (9–10 nM IGFBP-1) were used to make the assay sensitive with respect to affinities in the $10^{-8}$ M range. These assays showed that the bp1-625 peptide blocked IGFBP-1 binding to immobilized IGF-1 and was similar in activity to bp1-25, having about 20-fold improved potency over bp1-01 (FIG. 4).

It may be predicted that bp1-625 will block IGF-I binding to IGFBP-1 and produce IGF-like activity on cells, with similar potency to bp1-21A, bp1-25, or bp1-40. It would also be expected that a peptide comprising the sequence:

GlyGlnGlnSerCysAlaAlaGlyPro-LeuGlnTrpLeuCysGluHisTyrPheSerThrTyr (SEQ ID NO:28) would act similarly to bp1-625.

The bp1-625-Z fusion is useful for producing IGFBP-binding peptides from *E. coli*, and the Z part of the fusion can be advantageously attached to other peptides herein than just bp1-625.

The present invention has of necessity been discussed herein by reference to certain specific methods and materials. It is to be understood that the discussion of these specific methods and materials in no way constitutes any limitation on the scope of the present invention, which extends to any and all alternative materials and methods suitable for accomplishing the objectives of the present invention.

What is claimed is:

1. A constrained helical peptide comprising a sequence of nine amino acid residues having a first terminal residue and a second terminal residue, wherein said residues flank an internal sequence of seven amino acids and have side-chains covalently bonded to each other to form a locking moiety and thereby constrain the peptide, wherein said peptide inhibits the binding of IGF-I to IGFBP-1, and wherein the internal sequence is Xaa(7)LeuAlaXaa(10)Xaa(11)Xaa(12)Xaa(13) (SEQ ID NO:31), wherein Xaa(7), Xaa(11), Xaa(12), and Xaa(13) are independently Nal(1), Lys, His, Phe, Trp, Tyr, Pro, Gln, or Met, and Xaa(10) is any amino acid.

2. The peptide of claim 1 wherein the first and second terminal residues are independently Asp or Glu residues.

3. The peptide of claim 2 wherein the first and second terminal residues are Glu residues.

4. The peptide of claim 1 wherein Xaa(7) is Trp.

5. The peptide of claim 1 wherein Xaa(10) is Glu.

6. The peptide of claim 1 wherein Xaa(12) is Tyr.

7. The peptide of claim 1 wherein Xaa(13) is Phe.

* * * * *

SEQUENCE LISTING

```
<160> NUMBER OF SEQ ID NOS:   50

<210> SEQ ID NO 1
<211> LENGTH: 18
<212> TYPE: PRT
<213> ORGANISM: Artificial sequence
<220> FEATURE:
<223> OTHER INFORMATION: Sequence is synthesized
<221> NAME/KEY: Xaa
<222> LOCATION: 1-4, 6-7, 9, 11-12, 15-18
<223> OTHER INFORMATION: Unknown amino acid

<400> SEQUENCE: 1

Xaa Xaa Xaa Xaa Cys Xaa Xaa Gly Xaa Leu Xaa Xaa Leu Cys Xaa
  1               5                  10                  15

Xaa Xaa Xaa

<210> SEQ ID NO 2
<211> LENGTH: 18
<212> TYPE: PRT
<213> ORGANISM: Artificial sequence
<220> FEATURE:
<223> OTHER INFORMATION: Sequence is synthesized

<400> SEQUENCE: 2

Glu Ala Arg Val Cys Arg Ala Gly Pro Leu Gln Trp Leu Cys Glu
  1               5                  10                  15

Lys Tyr Phe

<210> SEQ ID NO 3
<211> LENGTH: 14
<212> TYPE: PRT
<213> ORGANISM: Artificial sequence
<220> FEATURE:
<223> OTHER INFORMATION: Sequence is synthesized
```

```
<221> NAME/KEY: Xaa
<222> LOCATION: 2-3, 5, 7, 11-14
<223> OTHER INFORMATION: Unknown amino acid

<400> SEQUENCE: 3

Cys Xaa Xaa Gly Xaa Leu Xaa Trp Leu Cys Xaa Xaa Xaa Xaa
 1               5                  10

<210> SEQ ID NO 4
<211> LENGTH: 14
<212> TYPE: PRT
<213> ORGANISM: Artificial sequence
<220> FEATURE:
<223> OTHER INFORMATION: Sequence is synthesized

<400> SEQUENCE: 4

Cys Arg Ala Gly Ala Leu Gln Trp Leu Cys Glu Lys Tyr Phe
 1               5                  10

<210> SEQ ID NO 5
<211> LENGTH: 14
<212> TYPE: PRT
<213> ORGANISM: Artificial sequence
<220> FEATURE:
<223> OTHER INFORMATION: Sequence is synthesized

<400> SEQUENCE: 5

Cys Arg Ala Gly Arg Leu Gln Trp Leu Cys Glu Lys Tyr Phe
 1               5                  10

<210> SEQ ID NO 6
<211> LENGTH: 14
<212> TYPE: PRT
<213> ORGANISM: Artificial sequence
<220> FEATURE:
<223> OTHER INFORMATION: Sequence is synthesized

<400> SEQUENCE: 6

Cys Arg Ala Gly Asn Leu Gln Trp Leu Cys Glu Lys Tyr Phe
 1               5                  10

<210> SEQ ID NO 7
<211> LENGTH: 14
<212> TYPE: PRT
<213> ORGANISM: Artificial sequence
<220> FEATURE:
<223> OTHER INFORMATION: Sequence is synthesized
<221> NAME/KEY: Xaa
<222> LOCATION: 6
<223> OTHER INFORMATION: Xaa represents Nle

<400> SEQUENCE: 7

Cys Arg Ala Gly Pro Xaa Gln Trp Leu Cys Glu Lys Tyr Phe
 1               5                  10

<210> SEQ ID NO 8
<211> LENGTH: 14
<212> TYPE: PRT
<213> ORGANISM: Artificial sequence
<220> FEATURE:
<223> OTHER INFORMATION: Sequence is synthesized
<221> NAME/KEY: Xaa
<222> LOCATION: 9
<223> OTHER INFORMATION: Xaa represents Nle

<400> SEQUENCE: 8

Cys Arg Ala Gly Pro Leu Gln Trp Xaa Cys Glu Lys Tyr Phe
 1               5                  10
```

<210> SEQ ID NO 9
<211> LENGTH: 14
<212> TYPE: PRT
<213> ORGANISM: Artificial sequence
<220> FEATURE:
<223> OTHER INFORMATION: Sequence is synthesized

<400> SEQUENCE: 9

Cys Arg Ala Gly Pro Leu Gln Arg Leu Cys Glu Lys Tyr Phe
 1               5                  10

<210> SEQ ID NO 10
<211> LENGTH: 14
<212> TYPE: PRT
<213> ORGANISM: Artificial sequence
<220> FEATURE:
<223> OTHER INFORMATION: Sequence is synthesized
<221> NAME/KEY: Xaa
<222> LOCATION: 8
<223> OTHER INFORMATION: Xaa represents Nal(1)

<400> SEQUENCE: 10

Cys Arg Ala Gly Pro Leu Gln Xaa Leu Cys Glu Lys Tyr Phe
 1               5                  10

<210> SEQ ID NO 11
<211> LENGTH: 14
<212> TYPE: PRT
<213> ORGANISM: Artificial sequence
<220> FEATURE:
<223> OTHER INFORMATION: Sequence is synthesized

<400> SEQUENCE: 11

Cys Arg Ala Gly Pro Leu Gln His Leu Cys Glu Lys Tyr Phe
 1               5                  10

<210> SEQ ID NO 12
<211> LENGTH: 21
<212> TYPE: PRT
<213> ORGANISM: Artificial sequence
<220> FEATURE:
<223> OTHER INFORMATION: Sequence is synthesized
<221> NAME/KEY: Xaa
<222> LOCATION: 1-4, 16, 19
<223> OTHER INFORMATION: Unknown amino acid

<400> SEQUENCE: 12

Xaa Xaa Xaa Xaa Cys Arg Ala Gly Pro Leu Gln Trp Leu Cys Glu
 1               5                  10                  15

Xaa Tyr Phe Xaa Thr Tyr
                20

<210> SEQ ID NO 13
<211> LENGTH: 21
<212> TYPE: PRT
<213> ORGANISM: Artificial sequence
<220> FEATURE:
<223> OTHER INFORMATION: Sequence is synthesized

<400> SEQUENCE: 13

Ser Glu Val Gly Cys Arg Ala Gly Pro Leu Gln Trp Leu Cys Glu
 1               5                  10                  15

Lys Tyr Phe Ser Thr Tyr
                20

```
<210> SEQ ID NO 14
<211> LENGTH: 21
<212> TYPE: PRT
<213> ORGANISM: Artificial sequence
<220> FEATURE:
<223> OTHER INFORMATION: Sequence is synthesized

<400> SEQUENCE: 14

Ser Glu Val Gly Cys Arg Ala Gly Pro Leu Gln Trp Leu Cys Glu
 1               5                  10                  15

Lys Tyr Phe Ala Thr Tyr
                20

<210> SEQ ID NO 15
<211> LENGTH: 21
<212> TYPE: PRT
<213> ORGANISM: Artificial sequence
<220> FEATURE:
<223> OTHER INFORMATION: Sequence is synthesized

<400> SEQUENCE: 15

Ser Glu Val Gly Cys Arg Ala Gly Pro Leu Gln Trp Leu Cys Glu
 1               5                  10                  15

Lys Tyr Phe Gln Thr Tyr
                20

<210> SEQ ID NO 16
<211> LENGTH: 22
<212> TYPE: PRT
<213> ORGANISM: Artificial sequence
<220> FEATURE:
<223> OTHER INFORMATION: Sequence is synthesized

<400> SEQUENCE: 16

Ser Glu Val Gly Cys Arg Ala Gly Pro Leu Gln Trp Leu Cys Glu
 1               5                  10                  15

Lys Tyr Phe Gln Thr Tyr Thr
                20

<210> SEQ ID NO 17
<211> LENGTH: 21
<212> TYPE: PRT
<213> ORGANISM: Artificial sequence
<220> FEATURE:
<223> OTHER INFORMATION: Sequence is synthesized

<400> SEQUENCE: 17

Ser Glu Val Gly Cys Arg Ala Gly Pro Leu Gln Trp Leu Cys Glu
 1               5                  10                  15

Lys Tyr Phe Asp Thr Tyr
                20

<210> SEQ ID NO 18
<211> LENGTH: 21
<212> TYPE: PRT
<213> ORGANISM: Artificial sequence
<220> FEATURE:
<223> OTHER INFORMATION: Sequence is synthesized

<400> SEQUENCE: 18

Ser Glu Val Gly Cys Arg Ala Gly Pro Leu Gln Trp Leu Cys Glu
 1               5                  10                  15

Lys Tyr Phe Glu Thr Tyr
                20
```

-continued

<210> SEQ ID NO 19
<211> LENGTH: 21
<212> TYPE: PRT
<213> ORGANISM: Artificial sequence
<220> FEATURE:
<223> OTHER INFORMATION: Sequence is synthesized

<400> SEQUENCE: 19

```
Ser Glu Val Gly Cys Arg Ala Gly Pro Leu Gln Trp Leu Cys Glu
  1               5                  10                  15

Lys Tyr Phe Lys Thr Tyr
                 20
```

<210> SEQ ID NO 20
<211> LENGTH: 21
<212> TYPE: PRT
<213> ORGANISM: Artificial sequence
<220> FEATURE:
<223> OTHER INFORMATION: Sequence is synthesized

<400> SEQUENCE: 20

```
Glu Ala Arg Val Cys Arg Ala Gly Pro Leu Gln Trp Leu Cys Glu
  1               5                  10                  15

Lys Tyr Phe Ser Thr Tyr
                 20
```

<210> SEQ ID NO 21
<211> LENGTH: 21
<212> TYPE: PRT
<213> ORGANISM: Artificial sequence
<220> FEATURE:
<223> OTHER INFORMATION: Sequence is synthesized

<400> SEQUENCE: 21

```
Gly Gln Gln Ser Cys Arg Ala Gly Pro Leu Gln Trp Leu Cys Glu
  1               5                  10                  15

Lys Tyr Phe Ser Thr Tyr
                 20
```

<210> SEQ ID NO 22
<211> LENGTH: 21
<212> TYPE: PRT
<213> ORGANISM: Artificial sequence
<220> FEATURE:
<223> OTHER INFORMATION: Sequence is synthesized

<400> SEQUENCE: 22

```
Ala Ser Ser Met Cys Arg Ala Gly Pro Leu Gln Trp Leu Cys Glu
  1               5                  10                  15

Lys Tyr Phe Ser Thr Tyr
                 20
```

<210> SEQ ID NO 23
<211> LENGTH: 21
<212> TYPE: PRT
<213> ORGANISM: Artificial sequence
<220> FEATURE:
<223> OTHER INFORMATION: Sequence is synthesized

<400> SEQUENCE: 23

```
Gln Gly Pro Asp Cys Arg Ala Gly Pro Leu Gln Trp Leu Cys Glu
  1               5                  10                  15

Lys Tyr Phe Ser Thr Tyr
                 20
```

<210> SEQ ID NO 24
<211> LENGTH: 21
<212> TYPE: PRT
<213> ORGANISM: Artificial sequence
<220> FEATURE:
<223> OTHER INFORMATION: Sequence is synthesized

<400> SEQUENCE: 24

Gln Ala Ser Glu Cys Arg Ala Gly Pro Leu Gln Trp Leu Cys Glu
 1               5                  10                  15

Lys Tyr Phe Ser Thr Tyr
                20

<210> SEQ ID NO 25
<211> LENGTH: 21
<212> TYPE: PRT
<213> ORGANISM: Artificial sequence
<220> FEATURE:
<223> OTHER INFORMATION: Sequence is synthesized

<400> SEQUENCE: 25

Ala Glu Thr Leu Cys Arg Ala Gly Pro Leu Gln Trp Leu Cys Glu
 1               5                  10                  15

Lys Tyr Phe Ser Thr Tyr
                20

<210> SEQ ID NO 26
<211> LENGTH: 21
<212> TYPE: PRT
<213> ORGANISM: Artificial sequence
<220> FEATURE:
<223> OTHER INFORMATION: Sequence is synthesized

<400> SEQUENCE: 26

Asn Ser Leu Leu Cys Arg Ala Gly Pro Leu Gln Trp Leu Cys Glu
 1               5                  10                  15

Lys Tyr Phe Ser Thr Tyr
                20

<210> SEQ ID NO 27
<211> LENGTH: 21
<212> TYPE: PRT
<213> ORGANISM: Artificial sequence
<220> FEATURE:
<223> OTHER INFORMATION: Sequence is synthesized

<400> SEQUENCE: 27

Ala Gln Trp Val Cys Arg Ala Gly Pro Leu Gln Trp Leu Cys Glu
 1               5                  10                  15

Lys Tyr Phe Ser Thr Tyr
                20

<210> SEQ ID NO 28
<211> LENGTH: 21
<212> TYPE: PRT
<213> ORGANISM: Artificial sequence
<220> FEATURE:
<223> OTHER INFORMATION: Sequence is synthesized

<400> SEQUENCE: 28

Gly Gln Gln Ser Cys Ala Ala Gly Pro Leu Gln Trp Leu Cys Glu
 1               5                  10                  15

His Tyr Phe Ser Thr Tyr

20

<210> SEQ ID NO 29
<211> LENGTH: 23
<212> TYPE: PRT
<213> ORGANISM: Artificial sequence
<220> FEATURE:
<223> OTHER INFORMATION: Sequence is synthesized

<400> SEQUENCE: 29

Gly Gln Gln Ser Cys Ala Ala Gly Pro Leu Gln Trp Leu Cys Glu
 1               5                  10                  15

His Tyr Phe Ser Thr Tyr Gly Arg
                20

<210> SEQ ID NO 30
<211> LENGTH: 74
<212> TYPE: PRT
<213> ORGANISM: Artificial sequence
<220> FEATURE:
<223> OTHER INFORMATION: Sequence is synthesized

<400> SEQUENCE: 30

Gly Gly Gly Ser Gly Gly Ala Gln His Asp Glu Ala Val Asp Asn
 1               5                  10                  15

Lys Phe Asn Lys Glu Gln Gln Asn Ala Phe Tyr Glu Ile Leu His
                20                  25                  30

Leu Pro Asn Leu Asn Glu Glu Gln Arg Asn Ala Phe Ile Gln Ser
                35                  40                  45

Leu Lys Asp Asp Pro Ser Gln Ser Ala Asn Leu Leu Ala Glu Ala
                50                  55                  60

Lys Lys Leu Asn Asp Ala Gln Ala Pro Asn Val Asp Met Asn
                65                  70

<210> SEQ ID NO 31
<211> LENGTH: 7
<212> TYPE: PRT
<213> ORGANISM: Artificial sequence
<220> FEATURE:
<223> OTHER INFORMATION: Sequence is synthesized
<221> NAME/KEY: Xaa
<222> LOCATION: 1, 4-7
<223> OTHER INFORMATION: Unknown amino acid

<400> SEQUENCE: 31

Xaa Leu Ala Xaa Xaa Xaa Xaa
 1               5

<210> SEQ ID NO 32
<211> LENGTH: 19
<212> TYPE: PRT
<213> ORGANISM: Artificial sequence
<220> FEATURE:
<223> OTHER INFORMATION: Sequence is synthesized
<221> NAME/KEY: Xaa
<222> LOCATION: 1-7, 11, 14-17, 19
<223> OTHER INFORMATION: Unknown amino acid

<400> SEQUENCE: 32

Xaa Xaa Xaa Xaa Xaa Xaa Xaa Pro Leu Glu Xaa Leu Ala Xaa Xaa
 1               5                  10                  15

Xaa Xaa Glu Xaa

<210> SEQ ID NO 33

```
<211> LENGTH: 15
<212> TYPE: PRT
<213> ORGANISM: Artificial sequence
<220> FEATURE:
<223> OTHER INFORMATION: Sequence is synthesized
<221> NAME/KEY: Xaa
<222> LOCATION: 1-3, 7, 10-13
<223> OTHER INFORMATION: Unknown amino acid

<400> SEQUENCE: 33

Xaa Xaa Xaa Pro Leu Glu Xaa Leu Ala Xaa Xaa Xaa Xaa Glu Gly
  1               5                  10                  15

<210> SEQ ID NO 34
<211> LENGTH: 14
<212> TYPE: PRT
<213> ORGANISM: Artificial sequence
<220> FEATURE:
<223> OTHER INFORMATION: Sequence is synthesized

<400> SEQUENCE: 34

Arg Ala Gly Pro Leu Glu Trp Leu Ala Glu Lys Tyr Glu Gly
  1               5                  10

<210> SEQ ID NO 35
<211> LENGTH: 12
<212> TYPE: PRT
<213> ORGANISM: Artificial sequence
<220> FEATURE:
<223> OTHER INFORMATION: Sequence is synthesized

<400> SEQUENCE: 35

Arg Pro Leu Glu Trp Leu Ala Glu Lys Tyr Phe Glu
  1               5                  10

<210> SEQ ID NO 36
<211> LENGTH: 14
<212> TYPE: PRT
<213> ORGANISM: Artificial sequence
<220> FEATURE:
<223> OTHER INFORMATION: Sequence is synthesized

<400> SEQUENCE: 36

Arg Ala Gly Pro Leu Glu Trp Leu Ala Glu Lys Tyr Phe Glu
  1               5                  10

<210> SEQ ID NO 37
<211> LENGTH: 14
<212> TYPE: PRT
<213> ORGANISM: Artificial sequence
<220> FEATURE:
<223> OTHER INFORMATION: Sequence is synthesized

<400> SEQUENCE: 37

Cys Arg Ala Gly Pro Leu Gln Trp Leu Cys Glu Lys Tyr Phe
  1               5                  10

<210> SEQ ID NO 38
<211> LENGTH: 14
<212> TYPE: PRT
<213> ORGANISM: Artificial sequence
<220> FEATURE:
<223> OTHER INFORMATION: Sequence is synthesized

<400> SEQUENCE: 38

Cys Arg Ala Ala Pro Leu Gln Trp Leu Cys Glu Lys Tyr Phe
  1               5                  10
```

<210> SEQ ID NO 39
<211> LENGTH: 14
<212> TYPE: PRT
<213> ORGANISM: Artificial sequence
<220> FEATURE:
<223> OTHER INFORMATION: Sequence is synthesized

<400> SEQUENCE: 39

Cys Arg Ala Gly Pro Arg Gln Trp Leu Cys Glu Lys Tyr Phe
 1               5                  10

<210> SEQ ID NO 40
<211> LENGTH: 14
<212> TYPE: PRT
<213> ORGANISM: Artificial sequence
<220> FEATURE:
<223> OTHER INFORMATION: Sequence is synthesized

<400> SEQUENCE: 40

Cys Arg Ala Gly Pro Leu Gln Trp Arg Cys Glu Lys Tyr Phe
 1               5                  10

<210> SEQ ID NO 41
<211> LENGTH: 15
<212> TYPE: PRT
<213> ORGANISM: Artificial sequence
<220> FEATURE:
<223> OTHER INFORMATION: Sequence is synthesized

<400> SEQUENCE: 41

Cys Arg Ala Gly Pro Leu Gln Trp Leu Cys Glu Lys Tyr Phe Gly
 1               5                  10                  15

<210> SEQ ID NO 42
<211> LENGTH: 15
<212> TYPE: PRT
<213> ORGANISM: Artificial sequence
<220> FEATURE:
<223> OTHER INFORMATION: Sequence is synthesized

<400> SEQUENCE: 42

Cys Arg Ala Gly Pro Leu Gln Glu Leu Cys Glu Lys Tyr Ala Glu
 1               5                  10                  15

<210> SEQ ID NO 43
<211> LENGTH: 10
<212> TYPE: PRT
<213> ORGANISM: Artificial sequence
<220> FEATURE:
<223> OTHER INFORMATION: Sequence is synthesized

<400> SEQUENCE: 43

Leu Glu Trp Leu Ala Glu Lys Tyr Glu Gly
 1               5                  10

<210> SEQ ID NO 44
<211> LENGTH: 11
<212> TYPE: PRT
<213> ORGANISM: Artificial sequence
<220> FEATURE:
<223> OTHER INFORMATION: Sequence is synthesized

<400> SEQUENCE: 44

Pro Leu Glu Trp Leu Ala Glu Lys Tyr Glu Gly
 1               5                  10

```
<210> SEQ ID NO 45
<211> LENGTH: 10
<212> TYPE: PRT
<213> ORGANISM: Artificial sequence
<220> FEATURE:
<223> OTHER INFORMATION: Sequence is synthesized

<400> SEQUENCE: 45

Leu Glu Trp Leu Ala Glu Lys Tyr Phe Glu
  1               5                  10

<210> SEQ ID NO 46
<211> LENGTH: 4
<212> TYPE: PRT
<213> ORGANISM: Artificial sequence
<220> FEATURE:
<223> OTHER INFORMATION: Sequence is synthesized

<400> SEQUENCE: 46

Gly Gln Gln Ser
  1

<210> SEQ ID NO 47
<211> LENGTH: 4
<212> TYPE: PRT
<213> ORGANISM: Artificial sequence
<220> FEATURE:
<223> OTHER INFORMATION: Sequence is synthesized

<400> SEQUENCE: 47

Ser Glu Val Gly
  1

<210> SEQ ID NO 48
<211> LENGTH: 4
<212> TYPE: PRT
<213> ORGANISM: Artificial sequence
<220> FEATURE:
<223> OTHER INFORMATION: Sequence is synthesized

<400> SEQUENCE: 48

Ser Glu Met Val
  1

<210> SEQ ID NO 49
<211> LENGTH: 4
<212> TYPE: PRT
<213> ORGANISM: Artificial sequence
<220> FEATURE:
<223> OTHER INFORMATION: Sequence is synthesized

<400> SEQUENCE: 49

Glu Ala Arg Val
  1

<210> SEQ ID NO 50
<211> LENGTH: 19
<212> TYPE: PRT
<213> ORGANISM: Artificial sequence
<220> FEATURE:
<223> OTHER INFORMATION: Sequence is synthesized

<400> SEQUENCE: 50

Ser Glu Val Gly Cys Arg Ala Gly Pro Leu Gln Trp Leu Cys Glu
  1               5                  10                  15

Lys Tyr Phe Gly
```